US007250290B1

(12) United States Patent
Thomae et al.

(10) Patent No.: US 7,250,290 B1

(45) Date of Patent: Jul. 31, 2007

(54) ARSENIC METHYLTRANSFERASE SEQUENCE VARIANTS

(75) Inventors: Bianca A. Thomae, Bay Village, OH (US); Eric D. Wieben, Rochester, MN (US); Richard M. Weinshilboum, Rochester, MN (US); Thomas C. Wood, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 406 days.

(21) Appl. No.: 10/824,828

(22) Filed: Apr. 15, 2004

Related U.S. Application Data

(60) Provisional application No. 60/463,114, filed on Apr. 15, 2003.

(51) Int. Cl.
*C12N 9/10* (2006.01)
*C12N 15/00* (2006.01)
*C07H 21/04* (2006.01)

(52) U.S. Cl. ................. 435/320.1; 536/23.2; 536/24.3; 435/193

(58) Field of Classification Search ................ 435/193, 435/320.1; 536/23.2, 24.3
See application file for complete search history.

(56) References Cited

U.S. PATENT DOCUMENTS

| | | | |
|---|---|---|---|
| 5,451,683 | A | 9/1995 | Barrett et al. |
| 5,733,729 | A | 3/1998 | Lipshutz et al. |
| 5,770,722 | A | 6/1998 | Lockhart et al. |

FOREIGN PATENT DOCUMENTS

| | | |
|---|---|---|
| WO | WO 98/20019 | 5/1998 |
| WO | WO 99/57318 | 11/1999 |

OTHER PUBLICATIONS

Rodriguez I. R. et al., Structural analysis of the human hydroxyindole-O-methyltransferase gene. Presence of two distinct promoters, J. Biol.Chem. 1994, 269 , 31969-77, abstract.*
Wood T. C. et al. Arsenic Methyltransferase (AS3MT) Pharmacogenetics, J. Biol. Chem. 2006, 281, 7364-7373.*
Bradford, "A Rapid and Sensitive Method for the Quantitation of Microgram Quantities of Protein Utilizing the Principle of Protein-Dye Binding," *Anal. Biochem.*, 1976, 72:248-254.
Caine et al., "Recombinant Human Phenylethanolamine *N*-Methyltransferase: Overproduction in *Escherichia coli*, Purification, and Characterization," *Protein Expr. Purif.*, 1996, 8(2):160-166.
Chadwick et al., "Heterozygote and Mutation Detection by Direct Automated Fluorescent DNA Sequencing Using a Mutant *Taq* DNA Polymerase," *BioTechniques*, 1996, 20:676-683.
Cibelli et al., "Cloned Transgenic Calves Produced from Nonquiescent Fetal Fibroblasts," *Science*, 1998, 280:1256-1258.
Cleland, "Computer Programmes For Processing Enzyme Kinetic Data," *Nature*, 1963, 198:463-365.
Cole et al., "The EBV-Hybridoma Technique and its Application to Human Lung Cancer," *Monoclonal Antibodies and Cancer Therapy*, 1985, Alan R. Liss, Inc., pp. 77-96.
Cote et al., "Generation of human momoclonal anitbodies reactive with cellular antigens," *Proc. Natl. Acad. Sci. USA*, 1983, 80:2026-2030.
Excoffier and Slatkin, "Maximum-Likelihood Estimation of Molecular Haplotype Frequencies in a Diploid Population," *Mol. Biol. Evol.*, 1995, 12(5):921-927.
Gordon et al., "*Consed*: A Graphical Tool for Sequence Finishing," *Genome Res.*, 1998, 8:195-202.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in *BRCA1* using high density oligonucleotide arrays and two-colour fluorescence analysis," *Nat. Genet.*, 1996, 14:441-447.
Halushka et al., "Patterns of single-nucleotide polymorphisms in candidate genes for blood-pressure homeostasis," *Nat. Genet.*, 1999, 22:239-247.
Hartl and Clark, "Chromosomes and Heredity," *Principles of Population Genetics*, 3rd Edition, 1997, Sinauer Associates, Inc., Sunderland, MA, Chapter 3, pp. 96-106.
Hedrick, "An Introduction to Gametic Disequilibrium," *Genetics of Populations*, 2nd Edition, 2000, Jones and Bartlett, Sudbury, MA, pp. 396-405.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorgan. Med. Chem.*, 1996, 4(1):5-23.
Köhler and Milstein, "Continuous cultures of fused cells secreting antibody of predefined specificity," *Nature*, 1975, 256(5512):495-497.
Kozbor and Roder, "The production of monoclonal antibodies from human lymphocytes," *Immunology Today*, 1983, 4:72-79.
Lewis, "PCR's Competitors Are Alive and Well and Moving Rapidly Towards Commercialization," *Genetic Engineering News*, 1992, 12(9):1.
Lin et al., "A Novel *S*-Adenosyl-L-methionine:Arsenic(III) Methyltransferase from Rat Liver Cytosol.," *J. Biol. Chem.*, 2002, 277(13):10795-10803.
Long et al., "An E-M Algorithm and Testing Strategy for Multiple-Locus Haplotypes," *Am. J. Hum. Genet.*, 1995, 56:799-810.
Myakishev et al., "High-Throughput SNP Genotyping by Allele-Specific PCR with Universal Energy-Transfer-Labeled Primers," *Genome Res.*, 2001, 11:163-169.
Nickerson et al. "PolyPhred: automating the detection and genotyping of single nucleotide substitutions using fluorescence-based resequencing," *Nucl. Acids Res.*, 1997, 25(14):2745-2751.

(Continued)

*Primary Examiner*—Rebecca E. Prouty
*Assistant Examiner*—Malgorzata A. Walicka
(74) *Attorney, Agent, or Firm*—Fish & Richardson P.C.

(57) ABSTRACT

Isolated ASMT nucleic acid molecules that include a nucleotide sequence variant and nucleotides flanking the sequence variant are described, as well as ASMT allozymes. Methods for determining if a mammal is at risk for toxicity from acute or chronic arsenic exposure also are described.

9 Claims, 53 Drawing Sheets

OTHER PUBLICATIONS

Prince et al., "Robust and Accurate Single Nucleotide Polymorphism Genotyping by Dynamic Allele-Specific Hybridization (DASH): Design Critera and Assay Validation," *Genome Res.*, 2001, 11(1):152-162.

Schafer and Hawkins, "DNA variation and the future of human genetics," *Nat. Biotechnol.*, 1998, 16:33-39.

Shastry, "Gene disruption in mice: Models of development and disease," *Mol. Cell. Biochem.*, 1998, 181:163-179.

Stoneking et al., "Polulation Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense Nucleic Acid Drug Dev.*, 1997, 7(3):187-195.

Terwilliger and Ott, "Linkage Disequilibrium between Alleles at Marker Loci," *Handbook of Human Genetic Linkage*, 1994, The Johns Hopkins University Press, Baltimore, pp. 188-193.

Underhill et al., "Detection of Numerous Y Chromosome Biallelic Polymorphisms of Denaturing High-Performance Liquid Chromatography," *Genome Res.*, 1997, 7:996-1005.

Wakayama et al., "Full-term development of mice from enucleated oocytes injected with cumulus cell nuclei," *Nature*, 1998, 394(6691):369-374.

Weiss, "Hot Prospect for New Gene Amplifier," *Science*, 1991, 254:1292-1293.

Wilkinson, "Statistical Estimations in Enzyme Kinetics," *Biochem. J.*, 1961, 80:324-332.

Wilmut et al., "Viable offspring derived from fetal and adult mammalian cells,"0 *Nature*, 1997, 385(6619):810-813.

Wong et al., "Human GM-CSF: Molecular Cloning of the Complementary DNA and Purification of the Natural and Recombinant Proteins," *Science*, 1985, 228:810-815.

Zakharyan et al., "Enzymatic Methylation of Arsenic Compounds: Assay, Partial Purification, and Properties of Arsenite Methyltransferase and Monomethylarsonic Acid Methyltransferase of Rabbit Liver," *Chem. Res. Toxicol.*, 1995, 8:1029-1038.

Chin, "On the preparation and utilization of isolated and purified oligonucleotides," University of North Carolina, Mar. 9, 2002 (on CD due to large volume of pages).

* cited by examiner

Figure 1 – page 1

```
     aagggtaggggagaaaatttctatgtatgttagtttttatcttaaaaaattagctttt
   1 ---------+---------+---------+---------+---------+---------+ 60
     ttcccatcccctcttttaaagatacatacaatcaaaaaatagaatttttttaatcgaaaa

     gtgaggctgggcgtggtggctcacgcctgtaatcccagcactttgggaggccgaggcggg
  61 ---------+---------+---------+---------+---------+---------+ 120
     cactccgacccgcaccaccgagtgcggacattagggtcgtgaaaccctccggctccgccc

     cagatcacgaggtctggagattgagaccgtcctggctaacacagtgaaaccccgtctcta
 121 ---------+---------+---------+---------+---------+---------+ 180
     gtctagtgctccagacctctaactctggcaggaccgattgtgtcactttggggcagagat

     ctaaaaatacaaaaaattagctgggcgtggtggcgggcgcctgtagtcccagctattcgg
 181 ---------+---------+---------+---------+---------+---------+ 240
     gatttttatgttttttaatcgacccgcaccaccgcccgcggacatcagggtcgataagcc

     gaggtgaggcagtagaatggcatgaacccgggaggcggagcttgcagtgagctgagatcc
 241 ---------+---------+---------+---------+---------+---------+ 300
     ctccactccgtcatcttaccgtacttgggccctccgcctcgaacgtcactcgactctagg

     tgccactgcactccagcctgggtgacagagcgagactctgtctcaaaaaaataaaaaagc
 301 ---------+---------+---------+---------+---------+---------+ 360
     acggtgacgtgaggtcggacccactgtctcgctctgagacagagtttttttatttttttcg

     ttttgccaatatttaaaatatgacttgatgtgagagtcttaatttcttctacgcagtata
 361 ---------+---------+---------+---------+---------+---------+ 420
     aaaacggttataaattttatactgaactacactctcagaattaaagaagatgcgtcatat

     cagatatatagcattcctgtcatttagcaggggtgatagtaaaacaaaaaaacaaaaaac
 421 ---------+---------+---------+---------+---------+---------+ 480
     gtctatatatcgtaaggacagtaaatcgtccccactatcattttgtttttttgttttttg

     cccacaaaacctgtggtgaggcactgaccaatcagaatgattgatggtcacagtctggtc
 481 ---------+---------+---------+---------+---------+---------+ 540
     gggtgttttggacaccactccgtgactggttagtcttactaactaccagtgtcagaccag

     caaaattagcccccacaccagacaccatggaggaaaagtgagagtaactcaatttaagtt
 541 ---------+---------+---------+---------+---------+---------+ 600
     gttttaatcgggggtgtggtctgtggtacctccttttcactctcattgagttaaattcaa

     gacagtggtttgttttattgcagtttatctgtgtgtgaataggtagatttaaggattgtt
 601 ---------+---------+---------+---------+---------+---------+ 660
     ctgtcaccaaacaaaataacgtcaaatagacacacacttatccatctaaattcctaacaa

     ggccaggtgtggtggctcacacctggaatcccagcacttttaggaggcagaggcaggcgg
 661 ---------+---------+---------+---------+---------+---------+ 720
     ccggtccacaccaccgagtgtggaccttagggtcgtgaaaatcctccgtctccgtccgcc

     atcacttgagatcaggagttcgagacagcctggccaacatggtgaaaccctgtctctact
 721 ---------+---------+---------+---------+---------+---------+ 780
     tagtgaactctagtcctcaagctctgtcggaccggttgtaccactttgggacagagatga
```

Figure 1 – page 2

```
     aaaaatacaaattagccaggcatggtagtgcatgcctgtaattccagctacttgggaggc
 781 ---------+---------+---------+---------+---------+---------+ 840
     tttttatgtttaatcggtccgtaccatcacgtacggacattaaggtcgatgaaccctccg

     tgaggcaggagaatcgcttgaaccggggaggcagaggttgcagtgagccgagattgcgcc
 841 ---------+---------+---------+---------+---------+---------+ 900
     actccgtcctcttagcgaacttggcccctccgtctccaacgtcactcggctctaacgcgg

     attgcgctccagcttgggcaacaagagcgaaactctgtctcaaaaaaaaaaaaaaaaaaa
 901 ---------+---------+---------+---------+---------+---------+ 960
     taacgcgaggtcgaacccgttgttctcgctttgagacagagttttttttttttttttttt

     aaggattgtcaaatgattcttgtaagtaaaccataaattaaagataacaaaacaagcaca
 961 ---------+---------+---------+---------+---------+---------+ 1020
     ttcctaacagtttactaagaacattcatttggtatttaatttctattgttttgttcgtgt

     agagaaaaatgatacagccctttccttgacctctcactaatctgcccttttaagataaag
1021 ---------+---------+---------+---------+---------+---------+ 1080
     tctctttttactatgtcgggaaaggaactggagagtgattagacgggaaaattctatttc

     atatcattttaactatgagaaggtaactgcttttctaaaggagctcattttatgaagata
1081 ---------+---------+---------+---------+---------+---------+ 1140
     tatagtaaaattgatactcttccattgacgaaaagatttcctcgagtaaaatacttctat

     atattttgaaaactaatatttaggagtgttttcaccattctatgattgcccaaaaactaa
1141 ---------+---------+---------+---------+---------+---------+ 1200
     tataaaacttttgattataaatcctcacaaaagtggtaagatactaacgggtttttgatt

     gtgatacttataaaaacactaagttttatacatatactagttggaaatattccaagctgt
1201 ---------+---------+---------+---------+---------+---------+ 1260
     cactatgaatatttttgtgattcaaaatatgtatatgatcaacctttataaggttcgaca

     agaaatattccaacaaggattatttccatggggttaatttgttaaaaatataaaagacac
1261 ---------+---------+---------+---------+---------+---------+ 1320
     tctttataaggttgttcctaataaaggtaccccaattaaacaatttttatattttctgtg

     cacctttctattaatttgtaacaactaattgacatcagagaagatgaaaatttactagct
1321 ---------+---------+---------+---------+---------+---------+ 1380
     gtggaaagataattaaacattgttgattaactgtagtctcttctactttaaatgatcga

     ggatatcaaccagattttgtattattggcaactgagattgaaaaatgaatgaaagagtc
1381 ---------+---------+---------+---------+---------+---------+ 1440
     cctatagttggtctaaaacataataaccgttgactctaactttttacttactttctcag

     tacttcatccatttagatatcctttcacttggatctccctgtttccttactgtcctaatg
1441 ---------+---------+---------+---------+---------+---------+ 1500
     atgaagtaggtaaatctataggaaagtgaacctagagggacaaaggaatgacaggattac

     aatagaaatgatcgttacaagctgggcatggtggcttgcacctgtagtcccagctactgg
1501 ---------+---------+---------+---------+---------+---------+ 1560
     ttatctttactagcaatgttcgacccgtaccaccgaacgtggacatcagggtcgatgacc
```

Figure 1 – page 3

```
     ggaggctgaggagggaggatggcttgaggccagagttgaaggatccagagatgattgcgc
1561 ---------+---------+---------+---------+---------+---------+ 1620
     cctccgactcctccctcctaccgaactccggtctcaacttcctaggtctctactaacgcg

     agtgacgctaagcttgggccacagagttgagaccctgtctctaaaatttttttttaatt
1621 ---------+---------+---------+---------+---------+---------+ 1680
     tcactgcgattcgaacccggtgtctcaactctgggacagagattttaaaaaaaaattaa

     taaattataaaagagaaatgcttgttacaaccacaaagggaaacaagatatacacatat
1681 ---------+---------+---------+---------+---------+---------+ 1740
     atttaatattttctctttacgaacaatgttggtgtttccctttgttctatatgtgtata

     aattgtggaagtaaaaataaataatttaaaaatacttttgggtgctcgcttcggcagcac
1741 ---------+---------+---------+---------+---------+---------+ 1800
     ttaacaccttcatttttatttattaaatttttatgaaaacccacgagcgaagccgtcgtg

     atatagttggaatgatagagaagatttgcatggcccctgcgcaagatgacatacaaattc
1801 ---------+---------+---------+---------+---------+---------+ 1860
     tatatcaaccttactatctcttctaaacgtaccggggacgcgttctactgtatgtttaag

     gtgaagtgttccatatttaaaaaaacaaaaaatacttttgggcctggcactgtggctcat
1861 ---------+---------+---------+---------+---------+---------+ 1920
     cacttcacaaggtataaatttttttgttttttatgaaaacccggaccgtgacaccgagta

     gcctgtaatccaaacactttgggaggctgaggcgggcggattgcttgaacccaggagttg
1921 ---------+---------+---------+---------+---------+---------+ 1980
     cggacattaggtttgtgaaaccctccgactccgcccgcctaacgaacttgggtcctcaac

     gagaccagcctggacaacatggtgaaatcccgtctctataaaaaaatacaaaaattaacc
1981 ---------+---------+---------+---------+---------+---------+ 2040
     ctctggtcggacctgttgtaccactttagggcagagatatttttttatgtttttaattgg

     aggtgtggtggtgcacgcctgtaatccaaggtacttgggaggctgaggcgggaggatcgc
2041 ---------+---------+---------+---------+---------+---------+ 2100
     tccacaccaccacgtgcggacattaggttccatgaaccctccgactccgccctcctagcg

     ttgagccaggaggttgggcctgggtaacagagaccgtctcaaaaaaatttaaaaattaaa
2101 ---------+---------+---------+---------+---------+---------+ 2160
     aactcggtcctccaacccggacccattgtctctggcagagtttttttaaatttttaattt

     aaaaaaactttctgcaagatgaagtgacaatacctggaaaatacatgtgacttgaccaaa
2161 ---------+---------+---------+---------+---------+---------+ 2220
     tttttttgaaagacgttctacttcactgttatggaccttttatgtacactgaactggttt
                                                           (-676)
     aattactataggtgaaaataaatttagcaaagttgctttcctaaatacaacccaaaatag
2221 ---------+---------+---------+---------+---------+---------+ 2280
     ttaatgatatccacttttatttaaatcgtttcaacgaaaggatttatgttgggttttatc

     actgggaacagctacatactgttaatggttccctctatgtgacattctagaaaaggcaga
2281 ---------+---------+---------+---------+---------+---------+ 2340
     tgacccttgtcgatgtatgacaattaccaagggagatacactgtaagatcttttccgtct
```

Figure 1 – page 4

```
     actatagggagggaaaacatctgtggttgcccaggagctaggggtgggaagagggaattt
2341 ---------+---------+---------+---------+---------+---------+ 2400
     tgatatccctccctttgtagacaccaacgggtcctcgatccccacccttctcccttaaa
                  (-542)
     actacaaagaggcacgaagaaacttgtgggccagagctatttggtctccgttttggtga
2401 ---------+---------+---------+---------+---------+---------+ 2460
     tgatgtttctccgtgcttctttgaacacccggtctcgataaaccagaggcaaaaccact
                      (-477)
     tgtatatacgtttgccagagttcacagaactgcacactgaagaaagatggatttcacgga
2461 ---------+---------+---------+---------+---------+---------+ 2520
     acatatatgcaaacggtctcaagtgtcttgacgtgtgacttctttctacctaaagtgcct
                  (-420)
     atgtgaattatatctcaacaaacttgacttcaaaaaacagatcgagaaaagatgattcta
2521 ---------+---------+---------+---------+---------+---------+ 2580
     tacacttaatatagagttgtttgaactgaagttttttgtctagctcttttctactaagat
                                                (-339)
     ttcccaaaaagggggagggggggaagatcattatataggtgagtgttcatttaaatcagag
2581 ---------+---------+---------+---------+---------+---------+ 2640
     aagggtttttccccctcccccccttctagtaatatatccactcacaagtaaatttagtctc

     tacgagatttatccgtgaaaatcgcagtggagcgaacaagggggatgctgataccgacct
2641 ---------+---------+---------+---------+---------+---------+ 2700
     atgctctaaataggcactttagcgtcacctcgcttgttcccccctacgactatggctgga

     cctggttggaaagcctgtagagcagcgcggatgacagtggaacagcgggtcaggcggtgg
2701 ---------+---------+---------+---------+---------+---------+ 2760
     ggaccaacctttcggacatctcgtcgcgcctactgtcaccttgtcgcccagtccgccacc

     gcgcctgagcgaggggctagagcgggatgggcgggcggagcaagcctgccagcctgggcg
2761 ---------+---------+---------+---------+---------+---------+ 2820
     cgcggactcgctccccgatctcgccctacccgcccgcctcgttcggacggtcggacccgc
                    (-116) (-114)                                      Exon 1
     gggcctcggcacaggagctggctgcgggagcccgccgtcctgagtcgcaggccgaggaga
2821 ---------+---------+---------+---------+---------+---------+ 2880
     cccggagccgtgtcctcgaccgacgccctcgggcggcaggactcagcgtccggctcctct

     cagtgagtgcgcgccctgagtcgcaggccgaggagacagtgagtgcgcgccctgagtcgc
2881 ---------+---------+---------+---------+---------+---------+ 2940
     gtcactcacgcgcgggactcagcgtccggctcctctgtcactcacgcgcgggactcagcg

     aggccgaggagacagtgagtgcgcgccctgggcgccccgccccagcccccagccccttcc
2941 ---------+---------+---------+---------+---------+---------+ 3000
     tccggctcctctgtcactcacgcgcgggacccgcggggcggggtcgggggtcggggaagg

     ctgggcccccgcaaggcgggaacgcgagcgcctcccccgagctgtgtctcgagacctttg
3001 ---------+---------+---------+---------+---------+---------+ 3060
     gacccgggggcgttccgcccttgcgctcgcggagggggctcgacacagagctctggaaac

     tcctcccctcacccctcggcccgctgcctgccctttactggcccccctccctcatgcccgt
3061 ---------+---------+---------+---------+---------+---------+ 3120
     aggaggggagtggggagccgggcgacggacgggaaatgaccgggggagggagtacgggca
```

Figure 1 – page 5

```
                                                                   Exon 2
     ccctcagcaccctctcctttcaactaactttcccgctcccgacagtggctgcacttcgtg
3121 ---------+---------+---------+---------+---------+---------+ 3180
     gggagtcgtgggagaggaaagttgattgaaagggcgagggctgtcaccgacgtgaagcac

                                                 M  A  A  L  R  D -

     acgctgagatacagaaggacgtgcaggtgagagctgtagggcctggaatggcccaagtgg
3181 ---------+---------+---------+---------+---------+---------+ 3240
     tgcgactctatgtcttcctgcacgtccactctcgacatcccggaccttaccgggttcacc

       A  E  I  Q  K  D  V  Q

     agcctaggctaatggaagtctggcctggcccgcaccctgtcccccgggactcctggagtc
3241 ---------+---------+---------+---------+---------+---------+ 3300
     tcggatccgattaccttcagaccggaccgggcgtgggacagggggccctgaggacctcag

     ggggtagggcagggtctaggcttcgacctttccagggaactgaggtcggccaagtggagg
3301 ---------+---------+---------+---------+---------+---------+ 3360
     ccccatcccgtcccagatccgaagctggaaaggtcccttgactccagccggttcacctcc
           I2(-75)                 I2(-47) C-INSERTION
     tggaggtggtgacggagccctcgcgctgcagtcacagctcttctccctctctacccctca
3361 ---------+---------+---------+---------+---------+---------+ 3420
     acctccaccactgcctcgggagcgcgacgtcagtgtcgagaagagggagagatggggagt
               I2(-10)                                      Exon 3
     ctccactgtgggacgctgggtcagacctactacgggcaggtgctgaagagatcggcagac
3421 ---------+---------+---------+---------+---------+---------+ 3480
     gaggtgacaccctgcgacccagtctggatgatgcccgtccacgacttctctagccgtctg

                           T  Y  Y  G  Q  V  L  K  R  S  A  D  -

     ctccagaccaacggctgtgtcaccacagccaggccggtccccaagcacatccgggaagcc
3481 ---------+---------+---------+---------+---------+---------+ 3540
     gaggtctggttgccgacacagtggtgtcggtccggccaggggttcgtgtaggcccttcgg

     L  Q  T  N  G  C  V  T  T  A  R  P  V  P  K  H  I  R  E  A  -

     ttgcaaaatgtacacgaagaagtagccctaaggtagagtgccctgtgctgtccccaggaa
3541 ---------+---------+---------+---------+---------+---------+ 3600
     aacgttttacatgtgcttcttcatcgggattccatctcacgggacacgacaggggtcctt

     L  Q  N  V  H  E  E  V  A  L  R

     gaccccaaacagcagttttcccaaaagataatgatgcaggtcactagggaattaacccgt
3601 ---------+---------+---------+---------+---------+---------+ 3660
     ctggggtttgtcgtcaaaagggttttctattactacgtccagtgatcccttaattgggca

     agccaccaacccatcagcttgccttgtctattgtaaaaatcctaaatctcagcacccatc
3661 ---------+---------+---------+---------+---------+---------+ 3720
     tcggtggttgggtagtcgaacggaacagataacatttttaggatttagagtcgtgggtag
```

Figure 1 – page 6

```
     atcttactgctctaagaacctccgatgagtctgggcgcgccagtgagcctgtagtcccaa
3721 ---------+---------+---------+---------+---------+---------+ 3780
     tagaatgacgagattcttggaggctactcagacccgcgcggtcactcggacatcagggtt

     gtgcttgggaggctgaggcagaggatcgcgtgagcccagaagttacaggctgtagtgtgc
3781 ---------+---------+---------+---------+---------+---------+ 3840
     cacgaaccctccgactccgtctcctagcgcactcgggtcttcaatgtccgacatcacacg

     gatccgggatgtgaatagccactgcactccagcttggtcaacatagccagatgcatctct
3841 ---------+---------+---------+---------+---------+---------+ 3900
     ctaggccctacacttatcggtgacgtgaggtcgaaccagttgtatcggtctacgtagaga

     aaaataaatgcgtactttaaaaaaattgcctaaaaaaagaacctccagcgtgaacactc
3901 ---------+---------+---------+---------+---------+---------+ 3960
     ttttatttacgcatgaaatttttttaacggatttttttcttggaggtcgcacttgtgag

     tgtagtccctacccatgctcacagaatacagtcacactcactggatctgccattcaagat
3961 ---------+---------+---------+---------+---------+---------+ 4020
     acatcagggatgggtacgagtgtcttatgtcagtgtgagtgacctagacggtaagttcta

     atgcgcagttcagcacccactaatcaaccttggcccttttgacccttcccttcctcactc
4021 ---------+---------+---------+---------+---------+---------+ 4080
     tacgcgtcaagtcgtgggtgattagttggaaccgggaaaactgggaagggaaggagtgag

     catcagcactgcctgcccagccggcagtcaccaatttggaaggtcttcccttttcttttt
4081 ---------+---------+---------+---------+---------+---------+ 4140
     gtagtcgtgacggacgggtcggccgtcagtggttaaaccttccagaagggaaaagaaaaa

     ccttcccaaccctgcgcatccagcaccacgctgctgtcccacctactgcatggagccttc
4141 ---------+---------+---------+---------+---------+---------+ 4200
     ggaagggttgggacgcgtaggtcgtggtgcgacgacagggtggatgacgtacctcggaag

     tctaatccttgagcggcctcttccccaaactgccacagcactctgtcactcggtctgtcc
4201 ---------+---------+---------+---------+---------+---------+ 4260
     agattaggaactcgccggagaaggggtttgacggtgtcgtgagacagtgagccagacagg

     gtaaatcacgggaagtgttttctgtgcacgatgttttatctcgcctctcaaatacaccta
4261 ---------+---------+---------+---------+---------+---------+ 4320
     catttagtgcccttcacaaaagacacgtgctacaaaatagagcggagagtttatgtggat

     cgcggcggggagcggtggctcacgtccgtcatcccagaacttgggaggccaaggcaggta
4321 ---------+---------+---------+---------+---------+---------+ 4380
     gcgccgcccctcgccaccgagtgcaggcagtagggtcttgaaccctccggttccgtccat

     gatcacttgaggtcagaagttcaagaccgacctggtcaacatagtgaaaccctgtctcta
4381 ---------+---------+---------+---------+---------+---------+ 4440
     ctagtgaactccagtcttcaagttctggctggaccagttgtatcactttgggacagagat

     ctgaaaatacaaaaattagctgggtgtagtggggcacgcctgtagtcccagctacttggg
4441 ---------+---------+---------+---------+---------+---------+ 4500
     gacttttatgtttttaatcgacccacatcaccccgtgcggacatcagggtcgatgaaccc
```

Figure 1 – page 7

```
      aggctgagggaggagaatcacttgaacgtggaaggcggaggtcgcagtgagcggagattg
4501 ---------+---------+---------+---------+---------+---------+ 4560
      tccgactccctcctcttagtgaacttgcaccttccgcctccagcgtcactcgcctctaac

      tgccactgcactccagcctgggcaacagagaaaaactcagtcaaaacaaaacaaaacaaa
4561 ---------+---------+---------+---------+---------+---------+ 4620
      acggtgacgtgaggtcggacccgttgtctctttttgagtcagttttgttttgttttgttt

      aaaaaggccgggggtggtggcttatgtctgtaatcccagcactttgggaggccgaggcgg
4621 ---------+---------+---------+---------+---------+---------+ 4680
      tttttccggcccccaccaccgaatacagacattagggtcgtgaaaccctccggctccgcc

      gaggatcacgaggccaggagatcgagaccatcctggctatcatggtgaaaccccgtctct
4681 ---------+---------+---------+---------+---------+---------+ 4740
      ctcctagtgctccggtcctctagctctggtaggaccgatagtaccactttggggcagaga

      actaaaaatacaaaaatattatccgggtgtggcggcacgcgcctgtagttccggctgctg
4741 ---------+---------+---------+---------+---------+---------+ 4800
      tgatttttatgtttttataataggcccacaccgccgtgcgcggacatcaaggccgacgac

      gggaggctgaggcaggagaacggcgtgaacccgggaggcggagcttgcagtgagctgagt
4801 ---------+---------+---------+---------+---------+---------+ 4860
      ccctccgactccgtcctcttgccgcacttgggccctccgcctcgaacgtcactcgactca

      tcgagccactgcactccagcctgggtgacagggcaagactccgtctcaaaaaaaaaaaaa
4861 ---------+---------+---------+---------+---------+---------+ 4920
      agctcggtgacgtgaggtcggacccactgtcccgttctgaggcagagttttttttttttt

      aaaaaaaaaaaaaaaaaaattagccaggagtggtggcaggcgctcgtagtcctagctact
4921 ---------+---------+---------+---------+---------+---------+ 4980
      tttttttttttttttttttaatcggtcctcaccaccgtccgcgagcatcaggatcgatga

      cgggaggctgaggtaggagaatggtgtcaacccgggaggcggagcttgcggtgagctgag
4981 ---------+---------+---------+---------+---------+---------+ 5040
      gccctccgactccatcctcttaccacagttgggccctccgcctcgaacgccactcgactc

      atcgcgccactgcactccagcctgggcgacagagcgagactccgtctcaaacaaaacaaa
5041 ---------+---------+---------+---------+---------+---------+ 5100
      tagcgcggtgacgtgaggtcggacccgctgtctcgctctgaggcagagtttgttttgttt

      acaaaacaaaacaaaacaaatcaaaacaaaaaacgcctatgggacagaaaccttacattt
5101 ---------+---------+---------+---------+---------+---------+ 5160
      tgttttgttttgttttgtttagttttgttttttgcggataccctgtctttggaatgtaaa

      tttcctcaataactagcgcagtcctgggcctgaattagaagctcagctaatgattaaatg
5161 ---------+---------+---------+---------+---------+---------+ 5220
      aaaggagttattgatcgcgtcaggacccggacttaatcttcgagtcgattactaatttac

      tatttattcaacacattattttattttatttatttatttttgagacggagtctcactctg
5221 ---------+---------+---------+---------+---------+---------+ 5280
      ataaataagttgtgtaataaaataaaataaataaataaaaactctgcctcagagtgagac
```

Figure 1 – page 8

```
     tcccttaggctggagtgcagtggcgccatctctgctcactgcaacctctgcctcctgggt
5281 ---------+---------+---------+---------+---------+---------+ 5340
     agggaatccgacctcacgtcaccgcggtagagacgagtgacgttggagacggaggaccca

     tcaagccattctcctgcctcagcctcccgaggagctgggattacaggtacctgctaccgt
5341 ---------+---------+---------+---------+---------+---------+ 5400
     agttcggtaagaggacggagtcggagggctcctcgaccctaatgtccatggacgatggca

     gcccagctgatttttggtattttagtagagacagggtttcactatgttggccaggctg
5401 ---------+---------+---------+---------+---------+---------+ 5460
     cgggtcgactaaaaaccataaaatcatctctgtcccaaagtgatacaaccggtccgac

     gtctccaactccttgcctcaagcgatccgcctgccttgacctcccaaagtgctgtgatta
5461 ---------+---------+---------+---------+---------+---------+ 5520
     cagaggttgaggaacggagttcgctaggcggacggaactggagggtttcacgacactaat

     taggcgtgagccaccgcgcccagcctgaacacattatttagatggcttatgaagtctta
5521 ---------+---------+---------+---------+---------+---------+ 5580
     atccgcactcggtggcgcgggtcggacttgtgtaataaaatctaccgaatacttcagaat

     gtgcctagcacatgcccaacaatactgtggtaaagcagatacagtcccagccttcatggg
5581 ---------+---------+---------+---------+---------+---------+ 5640
     cacggatcgtgtacgggttgttatgacaccatttcgtctatgtcagggtcggaagtaccc

     tgtccagttcagtggagactaaacatcagaagtatgagtgaatgatgcaagaaagaagga
5641 ---------+---------+---------+---------+---------+---------+ 5700
     acaggtcaagtcacctctgatttgtagtcttcatactcacttactacgttctttcttcct

     aggaaggaaggaacggagggagggagggaggagggaagtatgtataagatttagtggttt
5701 ---------+---------+---------+---------+---------+---------+ 5760
     tccttccttccttgcctccctccctccctcctcccttcatacatattctaaatcaccaaa
                                     I3(-18)                          Exon 4
     catgtcttacagtctccagggaaaaaatatgtgttttccatttcccagatattatggctg
5761 ---------+---------+---------+---------+---------+---------+ 5820
     gtacagaatgtcagaggtcccttttttatacacaaaaggtaaagggtctataataccgac

                                                         Y  Y  G  C  -

     tggtctggtgatccctgagcatctagaaaactgctggattttggatctgggtagtggaag
5821 ---------+---------+---------+---------+---------+---------+ 5880
     accagaccactagggactcgtagatcttttgacgacctaaaacctagacccatcaccttc

      G  L  V  I  P  E  H  L  E  N  C  W  I  L  D  L  G  S  G  S  -

     tggcagagattgctatgtacttagccagctggttggtgaaaaaggacacgtgactggaat
5881 ---------+---------+---------+---------+---------+---------+ 5940
     accgtctctaacgatacatgaatcggtcgaccaaccactttttcctgtgcactgacctta

      G  R  D  C  Y  V  L  S  Q  L  V  G  E  K  G  H  V  T  G  I  -
```

Figure 1 – page 9

```
     agacatgaccaaaggccaggtgaggcatgatttggaagacaaggagaaaaagattctcaa
5941 ---------+---------+---------+---------+---------+---------+ 6000
     tctgtactggtttccggtccactccgtactaaaccttctgttcctctttttctaagagtt

      D  M  T  K  G  Q

     aagcattatttgaaaaataaagttgttttcttcgtggctcttcaaggataatttaagaaa
6001 ---------+---------+---------+---------+---------+---------+ 6060
     ttcgtaataaactttttatttcaacaaaagaagcaccgagaagttcctattaaattcttt

     gcttctagttagcaatgctcatttgtgccactagtgcttcctgtcttggaaactgataac
6061 ---------+---------+---------+---------+---------+---------+ 6120
     cgaagatcaatcgttacgagtaaacacggtgatcacgaaggacagaacctttgactattg
                                                       I4(217)
     ttgaacaattaggggttcttctgggcgaacacaagagtcggaggtttgctctgatatgaa
6121 ---------+---------+---------+---------+---------+---------+ 6180
     aacttgttaatccccaagaagacccgcttgtgttctcagcctccaaacgagactatactt

     tatcgtgacgatagagtggactttgatctttcccttcttgctgccatctatcctgaaaga
6181 ---------+---------+---------+---------+---------+---------+ 6240
     atagcactgctatctcacctgaaactagaaagggaagaacgacggtagataggactttct

     ttttgttattgaatgaggagtttattcaagccaaactgcacgggcagcagggagtttatg
6241 ---------+---------+---------+---------+---------+---------+ 6300
     aaaacaataacttactcctcaaataagttcggtttgacgtgcccgtcgtccctcaaatac
                             I4(365)
     tcccaggttgtagtatatcctacgtgtccacaggaatcttgtatgtttatccaaaataat
6301 ---------+---------+---------+---------+---------+---------+ 6360
     agggtccaacatcatataggatgcacaggtgtccttagaacatacaaataggttttatta
                 I4(414)
     ctaggggaagtatattctgttagtgataggaaattttaggaaaaagttgtgtattttttt
6361 ---------+---------+---------+---------+---------+---------+ 6420
     gatccccttcatataagacaatcactatcctttaaaatcctttttcaacacataaaaaa
         I4(467)                                                      Exon 5
     tcaaatgttatcaaaactatatttttcttactttaggtggaagtggctgaaaagtatct
6421 ---------+---------+---------+---------+---------+---------+ 6480
     agttttacaatagttttgatataaaaagaatgaaatccaccttcaccgacttttcataga

                                        V  E  V  A  E  K  Y  L  -

     tgactatcacatggaaaaatatggcttccaggcatctaatgtgacttttattcatggcta
6481 ---------+---------+---------+---------+---------+---------+ 6540
     actgatagtgtacctttttataccgaaggtccgtagattacactgaaaataagtaccgat

      D  Y  H  M  E  K  Y  G  F  Q  A  S  N  V  T  F  I  H  G  Y  -

     cattgagaagttgggagaggctggaatcaagaatgagagccatgatattgttgtgtaggt
6541 ---------+---------+---------+---------+---------+---------+ 6600
     gtaactcttcaaccctctccgaccttagttcttactctcggtactataacaacacatcca

      I  E  K  L  G  E  A  G  I  K  N  E  S  H  D  I  V  V
```

Figure 1 – page 10

```
     ctatattcttactgttatgactatagcccatttctttattattattattattattg
6601 ---------+---------+---------+---------+---------+---------+ 6660
     gatataagaatgacaatactgatatcgggtaaaagaaataataataataataataac

     agatggactctcgctctgtcacccaggccagagtgcagtggcccaatgtcagctcacgat
6661 ---------+---------+---------+---------+---------+---------+ 6720
     tctacctgagagcgagacagtgggtccggtctcacgtcaccgggttacagtcgagtgcta

     aacctctgcctcccgggttcaactgattctcttgcctcagcctctcaagtagctgggatt
6721 ---------+---------+---------+---------+---------+---------+ 6780
     ttggagacggagggcccaagttgactaagagaacggagtcggagagttcatcgaccctaa

     ataggcacacgctaccacatccagctaatttttaaatcttctttagtagagacagggt
6781 ---------+---------+---------+---------+---------+---------+ 6840
     tatccgtgtgcgatggtgtaggtcgattaaaaatttagaagaaatcatctctgtccca

     ttcaccatgttggccaggctggtctcaaactcctgatctcaggtgatccacccgcttcca
6841 ---------+---------+---------+---------+---------+---------+ 6900
     aagtggtacaaccggtccgaccagagtttgaggactagagtccactaggtgggcgaaggt

     cctcccaaagtgctgggattacaggtgtgaggcactgtgctcagccctcatttcctttg
6901 ---------+---------+---------+---------+---------+---------+ 6960
     ggagggtttcacgaccctaatgtccacactccgtgacacgagtcgggagtaaaggaaaac

     aacacagagatgtcactattactgtttgctgaattgactctcatttagggtgttaaacta
6961 ---------+---------+---------+---------+---------+---------+ 7020
     ttgtgtctctacagtgataatgacaaacgacttaactgagagtaaatcccacaatttgat

     aacttagcatggcttactaatgggagagagctggtttgagctgctggagctcaccagcag
7021 ---------+---------+---------+---------+---------+---------+ 7080
     ttgaatcgtaccgaatgattaccctctctcgaccaaactcgacgacctcgagtggtcgtc

     cagaacacaccagaccaagagggaacttacttgaaacttaaccacaaaccaatgaaccca
7081 ---------+---------+---------+---------+---------+---------+ 7140
     gtcttgtgtggtctggttctcccttgaatgaactttgaattggtgtttggttacttgggt

     aaagaccagcaggaccactaagtttgctcctacaatacatgctgacctgtatctttcata
7141 ---------+---------+---------+---------+---------+---------+ 7200
     tttctggtcgtcctggtgattcaaacgaggatgttatgtacgactggacatagaaagtat

     atattttcatggtaaattataggattctatttcctttttccctcaagttgttattgtca
7201 ---------+---------+---------+---------+---------+---------+ 7260
     tataaaagtaccatttaatatcctaagataaaggaaaaagggagttcaacaataacagt

     aatcatgcccaagtgacagctgcctttgaggaacatagcctgtttacgtgaagcataaga
7261 ---------+---------+---------+---------+---------+---------+ 7320
     ttagtacgggttcactgtcgacggaaactccttgtatcggacaaatgcacttcgtattct

     aatgccttgtgccggccaggtgcggtggctcacgcctataatcccagcattttgggaggc
7321 ---------+---------+---------+---------+---------+---------+ 7380
     ttacggaacacggccggtccacgccaccgagtgcggatattagggtcgtaaaaccctccg
```

Figure 1 – page 11

```
     cgaggcaggtggatcacgaggtcaggaattccagaccagcttgaacaacatggcgaaacc
7381 ---------+---------+---------+---------+---------+---------+ 7440
     gctccgtccacctagtgctccagtccttaaggtctggtcgaacttgttgtaccgctttgg

     ccgtctctactaaaaatacaaaaattagctgggtgtggtggcacatgcctgtaatcccag
7441 ---------+---------+---------+---------+---------+---------+ 7500
     ggcagagatgatttttatgtttttaatcgacccacaccaccgtgtacggacattagggtc

     ctatttaggaggctgaggcaggagaatcacttgaacccgggaggcggaggttgcaatgag
7501 ---------+---------+---------+---------+---------+---------+ 7560
     gataaatcctccgactccgtcctcttagtgaacttgggccctccgcctccaacgttactc

     ccgagattgcgccattgtactccagcctgggcaacaggagtgaaacatcctctcgggaaa
7561 ---------+---------+---------+---------+---------+---------+ 7620
     ggctctaacgcggtaacatgaggtcggacccgttgtcctcactttgtaggagagcccttt

     aaaaaaaaaagaaagaaatgccttgtgcagtaggcatctggtctgaggtttcatcttgtt
7621 ---------+---------+---------+---------+---------+---------+ 7680
     ttttttttttctttctttacggaacacgtcatccgtagaccagactccaaagtagaacaa

     acatggtgaacatcaggacagaaacaagtaagaatcatgcctgatgttattttctgcaca
7681 ---------+---------+---------+---------+---------+---------+ 7740
     tgtaccacttgtagtcctgtctttgttcattcttagtacggactacaataaaagacgtgt

     ttcaaacttgctaacaatttattgagattttaagcactctgtctctgatcttggggaaaa
7741 ---------+---------+---------+---------+---------+---------+ 7800
     aagtttgaacgattgttaaataactctaaaattcgtgagacagagactagaacccctttt

     gcttagttgaaggcattagaaagagaggagggaggcggtaagaatggggtagctttgaca
7801 ---------+---------+---------+---------+---------+---------+ 7860
     cgaatcaacttccgtaatctttctctcctccctccgccattcttaccccatcgaaactgt

     gaacggtgggaaccacctttagggtctgaaaggatttgcagatctctgagtgttgtgaag
7861 ---------+---------+---------+---------+---------+---------+ 7920
     cttgccacccttggtggaaatcccagactttcctaaacgtctagagactcacaacacttc
                                                                 Exon 6
     atttgctcgacatttcatctgttctcttttagatcaaactgtgttattaaccttgtgcct
7921 ---------+---------+---------+---------+---------+---------+ 7980
     taaacgagctgtaaagtagacaagagaaaatctagtttgacacaataattggaacacgga

                                     S  N  C  V  I  N  L  V  P  -
                                  517
     gataaacaacaagtgcttcaggaggcatatcgggtgctgaaggtgaggaggagagtgaga
7981 ---------+---------+---------+---------+---------+---------+ 8040
     ctatttgttgttcacgaagtcctccgtatagcccacgacttccactcctcctctcactct

     D  K  Q  Q  V  L  Q  E  A  Y  R  V  L  K
                                     I6(56)
     taaattatctttgaacatcagtaagagctgatgggttaagtcttgtttgttcccccttga
8041 ---------+---------+---------+---------+---------+---------+ 8100
     atttaatagaaacttgtagtcattctcgactacccaattcagaacaaacaagggggaact
```

Figure 1 – page 12

```
     actaagagctcaaactctcttaatttatccattaaatgaataaggggtggcaaaaggggg
8101 ---------+---------+---------+---------+---------+---------+ 8160
     tgattctcgagtttgagagaattaaataggtaatttacttattccccaccgtttccccc

     aaggggcaggaataccccggatatggattactttccctcttaggttgcaaaaggtagtaa
8161 ---------+---------+---------+---------+---------+---------+ 8220
     ttccccgtccttatggggcctatacctaatgaaagggagaatccaacgttttccatcatt

     atccgaggtgacagttgtcactgaatgtgttaaggtatttgctttcttgactgtctctcc
8221 ---------+---------+---------+---------+---------+---------+ 8280
     taggctccactgtcaacagtgacttacacaattccataaacgaaagaactgacagagagg

     tatttgctgctgtacatgatcctagaagagcatctgtggagctataggaatctttgcact
8281 ---------+---------+---------+---------+---------+---------+ 8340
     ataaacgacgacatgtactaggatcttctcgtagacacctcgatatccttagaaacgtga

     gactactaatgattgctttgaatatactctcttctagcatgtacagtgtttctcagggct
8341 ---------+---------+---------+---------+---------+---------+ 8400
     ctgatgattactaacgaaacttatatgagagaagatcgtacatgtcacaaagagtcccga

     tctgatttcttatctgtcatgatttcagatctttgggaagttacagaagatggaactttt
8401 ---------+---------+---------+---------+---------+---------+ 8460
     agactaaagaatagacagtactaaagtctagaaacccttcaatgtcttctaccttgaaaa

     acattaactacttgctaaaaggaaagcttgcaggagctccacagccttcattgtatcatg
8461 ---------+---------+---------+---------+---------+---------+ 8520
     tgtaattgatgaacgattttcctttcgaacgtcctcgaggtgtcggaagtaacatagtac

     agatgtgtatcttcatgatagtagatgaaatattcagccaggtgcggtagctcacacctg
8521 ---------+---------+---------+---------+---------+---------+ 8580
     tctacacatagaagtactatcatctactttataagtcggtccacgccatcgagtgtggac

     taatcccagtgctgtgggaggccgaggcgggcagatcacctgaggtcaggagtttgagac
8581 ---------+---------+---------+---------+---------+---------+ 8640
     attagggtcacgacaccctccggctccgcccgtctagtggactccagtcctcaaactctg

     cagcttggccaacatggagaaactctgtctctactaaaaatacaaaaattagctgggtgt
8641 ---------+---------+---------+---------+---------+---------+ 8700
     gtcgaaccggttgtacctctttgagacagagatgatttttatgtttttaatcgacccaca

     ggtggtgcgtgcctgtaatcccagctcctcgggaggctgaggtaggagaatagcttgaac
8701 ---------+---------+---------+---------+---------+---------+ 8760
     ccaccacgcacggacattagggtcgaggagccctccgactccatcctcttatcgaacttg

     ccagaagtcagaggttgcagtgagccaggatcgtgccactgcactccagcctgggagaca
8761 ---------+---------+---------+---------+---------+---------+ 8820
     ggtcttcagtctccaacgtcactcggtcctagcacggtgacgtgaggtcggaccctctgt

     gagcgagactccatctcaaaaaaaaaaaaaaaaaaaaaagattctagctgggtgggtggt
8821 ---------+---------+---------+---------+---------+---------+ 8880
     ctcgctctgaggtagagttttttttttttttttttttttctaagatcgacccacccacca
```

Figure 1 – page 13

```
      acatgcctgtactcccagctacttggatgctgaggcaagaggattgcttgagctctggag
8881  ---------+---------+---------+---------+---------+---------+ 8940
      tgtacggacatgagggtcgatgaacctacgactccgttctcctaacgaactcgagacctc

      tttgtgtgcagcttgggcaatatagtgtgatcactgcctctaaaaaatgttttttttt
8941  ---------+---------+---------+---------+---------+---------+ 9000
      aaacacacgtcgaacccgttatatcacactagtgacggagatttttttacaaaaaaaaaa

      tgagatggagtctcactctgctgtccaggctgtagtgcagtggcaggatttcatctcact
9001  ---------+---------+---------+---------+---------+---------+ 9060
      actctacctcagagtgagacgacaggtccgacatcacgtcaccgtcctaaagtagagtga

      gcaacctccgcctcctgggttcaaacaattcttttgcctcagcctccctagtagctggga
9061  ---------+---------+---------+---------+---------+---------+ 9120
      cgttggaggcggaggacccaagtttgttaagaaaacggagtcggagggatcatcgaccct

      ctacaggcgtgtgccaccatgcccagctaattttgtacttttagtagagacaagatttc
9121  ---------+---------+---------+---------+---------+---------+ 9180
      gatgtccgcacacggtggtacgggtcgattaaaacatgaaaatcatctctgttctaaag

      accatattggtcaggctgatcttgaactcctgatctcatgatctgcctcagcctcccaaa
9181  ---------+---------+---------+---------+---------+---------+ 9240
      tggtataaccagtccgactagaacttgaggactagagtactagacggagtcggagggttt

      gtgctgggattacaggcatgagccgctgtgcctggccaaaatttttttttaaattgacaa
9241  ---------+---------+---------+---------+---------+---------+ 9300
      cacgaccctaatgtccgtactcggcgacacggaccggttttaaaaaaaaaatttaactgtt

      cagattttgagattttggtttacaaagctgtcatagaactcaaatacaaatatctata
9301  ---------+---------+---------+---------+---------+---------+ 9360
      gtctaaaaactctaaaaccaaatgtttcgacagtatcttgagtttatgtttatagatat

      tagaaatgatttaatgatttagtgatgtctttgttagtatgtcattttacacgccagttc
9361  ---------+---------+---------+---------+---------+---------+ 9420
      atctttactaaattactaaatcactacagaaacaatcatacagtaaaatgtgcggtcaag

      actatctccaccaaaaatgtacttataaaaggtagaaacactattatagaatctagatct
9421  ---------+---------+---------+---------+---------+---------+ 9480
      tgatagaggtggtttttacatgaatattttccatctttgtgataatatcttagatctaga

      ccaggtttccaggttttgaaattagctaaataaaatgttaagttcctgatcactcattt
9481  ---------+---------+---------+---------+---------+---------+ 9540
      ggtccaaaggtccaaaaactttaatcgatttattttacaattcaaggactagtgagtaaa

      gccttacattttaaggataatattttaaagataaaatgtgttgttataaaagtaaataac
9541  ---------+---------+---------+---------+---------+---------+ 9600
      cggaatgtaaaattcctattataaaatttctattttacacaacaatattttcatttattg

      aacattacaaaaagttatatttttaatagaaatggggtcttgctgtcacccaggctgga
9601  ---------+---------+---------+---------+---------+---------+ 9660
      ttgtaatgtttttcaatataaaaaattatctttaccccagaacgacagtgggtccgacct
```

Figure 1 – page 14

```
      atgcagtgtcactatctgtacccctctaactcctgagttagaggggtccagatagtgaca
9661  ---------+---------+---------+---------+---------+---------+ 9720
      tacgtcacagtgatagacatggggagattgaggactcaatctccccaggtctatcactgt

      ctcactgtaccctctaactcctgggctcaaacaatcctcttgagtagctaggactccagg
9721  ---------+---------+---------+---------+---------+---------+ 9780
      gagtgacatgggagattgaggacccgagtttgttaggagaactcatcgatcctgaggtcc

      cacatgccaccatgcccagctagtttttaaatttctatatgggagagagggtcttgctgt
9781  ---------+---------+---------+---------+---------+---------+ 9840
      gtgtacggtggtacgggtcgatcaaaaatttaaagatatacctctctcccagaacgaca

      gttgccaaggctagtctcaaactgctctcctccagcaagcctcccacttcggcctcctga
9841  ---------+---------+---------+---------+---------+---------+ 9900
      caacggttccgatcagagtttgacgagaggaggtcgttcggagggtgaagccggaggact

      gtcattgggattagaggcctgagccatcatacctggcaaagttatactattcttaagaga
9901  ---------+---------+---------+---------+---------+---------+ 9960
      cagtaaccctaatctccggactcggtagtatggaccgtttcaatatgataagaattctct

      taaaagattatgaatactgatgatatcctctgttctacaatgacctggggctgcttttgg
9961  ---------+---------+---------+---------+---------+---------+ 10020
      attttctaatacttatgactactataggagacaagatgttactggaccccgacgaaaacc

      ttcagattggctaaaaatttaaatgtaagtaacctgaaaatctttatttaggagacagac
10021 ---------+---------+---------+---------+---------+---------+ 10080
      aagtctaaccgatttttaaatttacattcattggacttttagaaataaatcctctgtctg

      actcttagaatgtgattttattacctgttggataagccactgggaggaaaaaaaaccttg
10081 ---------+---------+---------+---------+---------+---------+ 10140
      tgagaatcttacactaaaataatggacaacctattcggtgaccctcctttttttttggaac

      gcacttgactattgattgtaactaaagaggcagctgctatttgttcacaaagggtcagct
10141 ---------+---------+---------+---------+---------+---------+ 10200
      cgtgaactgataactaacattgatttctccgtcgacgataaacaagtgtttcccagtcga
                                                         I6(-56)
      taaacattgctattgattttaaatttgattttgttcccctattcctttctttgttatggt
10201 ---------+---------+---------+---------+---------+---------+ 10260
      atttgtaacgataactaaaaatttaaactaaaacaaggggataaggaaagaaacaataca
                                                              Exon 7
      ggggtcaatgtaatcattaatcatcttgtttggactaatatgcctctgtttcagcatggt
10261 ---------+---------+---------+---------+---------+---------+ 10320
      ccccagttacattagtaattagtagaacaaacctgattatacggagacaaagtcgtacca

                                                         H  G   -

      ggggagttatatttcagtgacgtctatacgagccttgaactgccagaagaaatcaggaca
10321 ---------+---------+---------+---------+---------+---------+ 10380
      cccctcaatataaagtcactgcagatatgctcggaacttgacggtcttctttagtcctgt

      G  E  L  Y  F  S  D  V  Y  T  S  L  E  L  P  E  E  I  R  T  -
```

Figure 1 – page 15

```
      cacaaagttttatggggtaggtgatttgtttagtttagtattaaggcagatggttgtac
10381 ---------+---------+---------+---------+---------+---------+ 10440
      gtgtttcaaaataccccatccactaaaacaaatcaaatcataattccgtctaccaacatg

      H  K  V  L  W

      atgtgcagaactcctttctgctaatagccaggatgaggctatatgagatcacatggggtt
10441 ---------+---------+---------+---------+---------+---------+ 10500
      tacacgtcttgaggaaagacgattatcggtcctactccgatatactctagtgtaccccaa

      aggccatgaggccaaggttccattcttcctctgccattcaaaagtgatagggctttggat
10501 ---------+---------+---------+---------+---------+---------+ 10560
      tccggtactccggttccaaggtaagaaggagacggtaagttttcactatcccgaaaccta

      agtttaattcatctctttgagttatcgttttccaaattgtaaaatgtaaataataataca
10561 ---------+---------+---------+---------+---------+---------+ 10620
      tcaaattaagtagagaaactcaatagcaaaaggtttaacattttacatttattattatgt

      atctgccttatagggctgttatgaagattaaatgggataaagaatgggaaaaatactttg
10621 ---------+---------+---------+---------+---------+---------+ 10680
      tagacggaatatcccgacaatacttctaatttaccctatttcttacccttttttatgaaac

      aaaactctagtgtggaaatgaggacaattgttcccaagctggtgtcctcttagtcccctt
10681 ---------+---------+---------+---------+---------+---------+ 10740
      ttttgagatcacacctttactcctgttaacaagggttcgaccacaggagaatcaggggaa

      atgttctcatcattattgtgttctttattcctttattatcattttaatagtctggaagtt
10741 ---------+---------+---------+---------+---------+---------+ 10800
      tacaagagtagtaataacacaagaaataaggaaataatagtaaaattatcagaccttcaa

      gagataaatgcatgcttttcatcagtctatgaaatcaaaagttcttattcttaaaataat
10801 ---------+---------+---------+---------+---------+---------+ 10860
      ctctatttacgtacgaaaagtagtcagatactttagttttcaagaataagaattttatta

      attaactttattcttactatgtaataataaataggtaccgttaacaagttggaaagtgcc
10861 ---------+---------+---------+---------+---------+---------+ 10920
      taattgaaataagaatgatacattattatttatccatggcaattgttcaacctttcacgg

      aaaaaaaaaaaaaaaaagaaaaaattactaagctggacacagtggcacacacctgtaac
10921 ---------+---------+---------+---------+---------+---------+ 10980
      ttttttttttttttttcttttttaatgattcgacctgtgtcaccgtgtgtggacattg

      cccagatatttgggaggctgagtcaggaggattgcttgagcctaggagttcaggtacagc
10981 ---------+---------+---------+---------+---------+---------+ 11040
      gggtctataaaccctccgactcagtcctcctaacgaactcggatcctcaagtccatgtcg

      ctgggtgtcatagtaaaaccctatctcttaaaaaaattacttataatcatataacccagt
11041 ---------+---------+---------+---------+---------+---------+ 11100
      gacccacagtatcattttgggatagagaatttttttaatgaatattagtatattgggtca

      gataacttcttttttttttttttttttttttgagatggagtctcgctctgtcacccaggc
11101 ---------+---------+---------+---------+---------+---------+ 11160
      ctattgaagaaaaaaaaaaaaaaaaaaaaactctacctcagagcgagacagtgggtccg
```

Figure 1 – page 16

```
      tagagtgcagtggcgcaatcttggctcactgcaacctccacttcccgggttcaagtgatt
11161 ---------+---------+---------+---------+---------+---------+ 11220
      atctcacgtcaccgcgttagaaccgagtgacgttggaggtgaagggcccaagttcactaa

      ctcctgcctcagcctcccaagtagctgggattacaggtgcatgccaccatgcccagctaa
11221 ---------+---------+---------+---------+---------+---------+ 11280
      gaggacggagtcggagggttcatcgaccctaatgtccacgtacggtggtacgggtcgatt

      tttttgtatttttagtagagatggggtttcactgtgttggccaggctggtctccaacacc
11281 ---------+---------+---------+---------+---------+---------+ 11340
      aaaaacataaaaatcatctctaccccaaagtgacacaaccggtccgaccagaggttgtgg

      tgacctcatgatctgcccacctcggcctcccaaagtgctgggattacaggcatgagccac
11341 ---------+---------+---------+---------+---------+---------+ 11400
      actggagtactagacgggtggagccggagggtttcacgaccctaatgtccgtactcggtg

      cgcgctcggcctatgatttatttttatactactttattcacataacagtgcttttcaga
11401 ---------+---------+---------+---------+---------+---------+ 11460
      gcgcgagccggatactaaataaaaatatgatgaaataagtgtattgtcacgaaaagtct

      atgtggcgtactgcatacatgaatattatgcttgcagctgagtagaaccaatccaccagt
11461 ---------+---------+---------+---------+---------+---------+ 11520
      tacaccgcatgacgtatgtacttataatacgaacgtcgactcatcttggttaggtggtca

      gagtgtcctgaagaatggttcctagagaccatcagctagcacacccagtcttaaccatgg
11521 ---------+---------+---------+---------+---------+---------+ 11580
      ctcacaggacttcttaccaaggatctctggtagtcgatcgtgtgggtcagaattggtacc

      ctttctagaccttggagggatgctcaagttagcttctactgctaggatctatgttttaac
11581 ---------+---------+---------+---------+---------+---------+ 11640
      gaaagatctggaacctccctacgagttcaatcgaagatgacgatcctagatacaaaattg

      taataccatgtcctaattaattatatagaagaatagttcccttaatactgtattaagtgt
11641 ---------+---------+---------+---------+---------+---------+ 11700
      attatggtacaggattaattaatatatcttcttatcaagggaattatgacataattcaca
                                                                    Exon 8
      tggctggtctgtggtttttttgttgttgtttgtttttttaggtgagtgtctgggtggtgctt
11701 ---------+---------+---------+---------+---------+---------+ 11760
      accgaccagacaccaaaaaacaacaacaaacaaaaaatccactcacagacccaccacgaa

                                               G  E  C  L  G  G  A  L -

      tatactggaaggaacttgctgtccttgctcaaaaaattgggttctgccctccacgtttgg
11761 ---------+---------+---------+---------+---------+---------+ 11820
      atatgaccttccttgaacgacaggaacgagtttttaacccaagacgggaggtgcaaacc

        Y  W  K  E  L  A  V  L  A  Q  K  I  G  F  C  P  P  R  L  V -
```

Figure 1 – page 17

```
        tcactgccaatctcattacaattcaaaacaaggaactggaaagagttatcggtaagatat
  11821 ---------+---------+---------+---------+---------+---------+ 11880
        agtgacggttagagtaatgttaagttttgttccttgacctttctcaatagccattctata

          T  A  N  L  I  T  I  Q  N  K  E  L  E  R  V  I  G

        gacagacagcagggactattataactacagcttgaatgattgaaatgtggtgattagtaa
  11881 ---------+---------+---------+---------+---------+---------+ 11940
        ctgtctgtcgtccctgataatattgatgtcgaacttactaactttacaccactaatcatt

        gtaacttctgaaggagtctcattgagggatactttctgttatctggaaatagctatcttg
  11941 ---------+---------+---------+---------+---------+---------+ 12000
        cattgaagacttcctcagagtaactccctatgaaagacaatagacctttatcgatagaac
                              I8(154)
        cctcctgtacaatggtaacccccaaaaatttgatatttaataaagcactttgaagtca
  12001 ---------+---------+---------+---------+---------+---------+ 12060
        ggaggacatgttaccattgggggtttttaaaactataaattatttcgtgaaacttcagt
                              I8(213)
        ttcagtaaatagagtgaagtgctcagaaagataactgatgacatgcaaggaagaaaatca
  12061 ---------+---------+---------+---------+---------+---------+ 12120
        aagtcatttatctcacttcacgagtctttctattgactactgtacgttccttcttttagt

        tctttataacgtgtttgctccttgtctgctgagcaaggcaacaactgggggagtgctgga
  12121 ---------+---------+---------+---------+---------+---------+ 12180
        agaaatattgcacaaacgaggaacagacgactcgttccgttgttgaccccctcacgacct
                                                                      Exon 9
        gatgaaccgtgaataaattctattttaggtgactgtcgttttgtttctgcaacatttcg
  12181 ---------+---------+---------+---------+---------+---------+ 12240
        ctacttggcacttatttaagataaaaatccactgacagcaaaacaaagacgttgtaaagc

                                          D  C  R  F  V  S  A  T  F  R  -

        cctcttcaaacactctaagacaggaccaaccaagagatgccaagttatttacaatggagg
  12241 ---------+---------+---------+---------+---------+---------+ 12300
        ggagaagtttgtgagattctgtcctggttggttctctacggttcaataaatgttacctcc

         L  F  K  H  S  K  T  G  P  T  K  R  C  Q  V  I  Y  N  G  G  -
                                  860
        aattacaggacatgaaaaagaactaatgtttgatgccaattttacatttaaggtaaataa
  12301 ---------+---------+---------+---------+---------+---------+ 12360
        ttaatgtcctgtactttttcttgattacaaactacggttaaaatgtaaattccatttatt

         I  T  G  H  E  K  E  L  M  F  D  A  N  F  T  F  K

        aacaatttccatgacttctggtattctttctgctcttgcccttgctccagctatcttttc
  12361 ---------+---------+---------+---------+---------+---------+ 12420
        ttgttaaaggtactgaagaccataagaaagacgagaacgggaacgaggtcgatagaaaag

        ttgactttgcattgcctcccatttttctggtgttggtttgtttgtgtgtgtgtttaaatg
  12421 ---------+---------+---------+---------+---------+---------+ 12480
        aactgaaacgtaacggagggtaaaaagaccacaaccaaacaaacacacacacaaatttac
```

Figure 1 – page 18

```
      tatgtgtgtgtttcaagtggagtaaaaaagcattttttccccaatacttatttatttatt
12481 ---------+---------+---------+---------+---------+---------+ 12540
      atacacacacaaagttcacctcattttttcgtaaaaaaggggttatgaataaataaataa

      gacagggtctcgctctgtcacccaggctggagtgcagtagcacaatcatagttcactgca
12541 ---------+---------+---------+---------+---------+---------+ 12600
      ctgtcccagagcgagacagtgggtccgacctcacgtcatcgtgttagtatcaagtgacgt

      gcctgacctcctgggctcaagcgatcctcccacctcaggcttctgagtagctaggactac
12601 ---------+---------+---------+---------+---------+---------+ 12660
      cggactggaggacccgagttcgctaggagggtggagtccgaagactcatcgatcctgatg

      agactcatcaccacacctggctaatatttgtattttttgtagagatggggttttgccatg
12661 ---------+---------+---------+---------+---------+---------+ 12720
      tctgagtagtggtgtggaccgattataaacataaaaaacatctctaccccaaaacggtac

      ttgcccagactggtcttgaactcctgggctcaagtgatgtgcccacctcagcctcccaaa
12721 ---------+---------+---------+---------+---------+---------+ 12780
      aacgggtctgaccagaacttgaggacccgagttcactacacgggtggagtcggagggttt

      gtgctgggattacaggcgtgaaccaccgtgcccagccctcaatatttattataaaaatgt
12781 ---------+---------+---------+---------+---------+---------+ 12840
      cacgaccctaatgtccgcacttggtggcacgggtcgggagttataaataatatttttaca

      ttttggccaggtgcggtggctcacacctgtaatcctagcactttgggaggctgaggcagg
12841 ---------+---------+---------+---------+---------+---------+ 12900
      aaaaccggtccacgccaccgagtgtggacattaggatcgtgaaaccctccgactccgtcc

      cagattacctgaggtcaggagttcgagaccagcctgacgaacatggcgaaaacccatctc
12901 ---------+---------+---------+---------+---------+---------+ 12960
      gtctaatggactccagtcctcaagctctggtcggactgcttgtaccgcttttgggtagag

      tactaataaaaatacaaaaattagccgggcgtggtggtgggtgcctgtaatcccaactac
12961 ---------+---------+---------+---------+---------+---------+ 13020
      atgattatttttatgtttttaatcggcccgcaccaccacccacggacattagggttgatg

      tctggaggctgaggcaggagaattgcatgaacccgggaggtggaggttgaggtgagctga
13021 ---------+---------+---------+---------+---------+---------+ 13080
      agacctccgactccgtcctcttaacgtacttgggccctccacctccaactccactcgact

      gatcatgccattgcactccagcctgggcaacagagtgagactccatctcaaaaaaaaaa
13081 ---------+---------+---------+---------+---------+---------+ 13140
      ctagtacggtaacgtgaggtcggacccgttgtctcactctgaggtagagtttttttttt

      aaaaaaaagaagtttttgaatacagaaaagttaatagtacaatgaatacccacataggca
13141 ---------+---------+---------+---------+---------+---------+ 13200
      ttttttttcttcaaaaacttatgtcttttcaattatcatgttacttatgggtgtatccgt

      ttacctatatttcagcaattgagaacatttttccatgtttgtgtgtttatatgtgtatat
13201 ---------+---------+---------+---------+---------+---------+ 13260
      aatggatataaagtcgttaactcttgtaaaaaggtacaaacacacaaatatacacatata
```

Figure 1 – page 19

```
      atatatatatatttatttgctgagccattgaaaataagttgcagatattatgacatttta
13261 ---------+---------+---------+---------+---------+---------+ 13320
      tatatatatataaataaacgactcggtaacttttattcaacgtctataatactgtaaaat

      cccttaaatatttcagcatgcgtcccataggaatgtaatatccctctgcataatcacaat
13321 ---------+---------+---------+---------+---------+---------+ 13380
      gggaatttataaagtcgtacgcagggtatccttacattatagggagacgtattagtgtta

      accattacacacctaagaaaacttttacaagaagcctcattcagacattggattaatag
13381 ---------+---------+---------+---------+---------+---------+ 13440
      tggtaatgtgtggattcttttgaaaatgttcttcggagtaagtctgtaacctaattatc

      ggctatagagaagtaggatggaaaagagtaggagtatgtacaatagtatttcaattgttt
13441 ---------+---------+---------+---------+---------+---------+ 13500
      ccgatatctcttcatcctaccttttctcatcctcatacatgttatcataaagttaacaaa

      aattgtgtcaaggaattaagaaattttaatgttggatgatggcactaattggcattttta
13501 ---------+---------+---------+---------+---------+---------+ 13560
      ttaacacagttccttaattctttaaaattacaacctactaccgtgattaaccgtaaaaat

      ctgccctgtgcatagtaagatttgttttctcaaaatggaaaagttcaggctttggaatca
13561 ---------+---------+---------+---------+---------+---------+ 13620
      gacgggacacgtatcattctaaacaaaagagttttaccttttcaagtccgaaaccttagt

      gatacctgggttcaaattctggctctattattattgtttttatttttttttctgaatgt
13621 ---------+---------+---------+---------+---------+---------+ 13680
      ctatggacccaagtttaagaccgagataataataacaaaaataaaaaaaaagacttaca

      cactagacaaacttttattgaagcataaattgtggtacagaaatacattttaactgattt
13681 ---------+---------+---------+---------+---------+---------+ 13740
      gtgatctgtttgaaaataacttcgtatttaacaccatgtctttatgtaaaattgactaaa

      aagtccaacaccagtgaaaggagagattatggcaccaaaactttccctttcctatcatac
13741 ---------+---------+---------+---------+---------+---------+ 13800
      ttcaggttgtggtcactttcctctctaataccgtggttttgaaagggaaaggatagtatg

      catgatttagattatgatgcaatctacatttctcttttctaggctttgtcccatacaaat
13801 ---------+---------+---------+---------+---------+---------+ 13860
      gtactaaatctaatactacgttagatgtaaagagaaaagatccgaaacagggtatgttta

      ttgggcagtttttcaacattagaatttcaacattagaattcttaattctattaggaaaaa
13861 ---------+---------+---------+---------+---------+---------+ 13920
      aacccgtcaaaaagttgtaatcttaaagttgtaatcttaagaattaagataatccttttt

      aagcaacaaaaaaaccagacctcaagtcaacaaatctattggatattgtttatgaacgaa
13921 ---------+---------+---------+---------+---------+---------+ 13980
      ttcgttgtttttttggtctggagttcagttgtttagataacctataacaaatacttgctt

      gtccacgttaagcattggtcctcaaaacagagctcctcaaaatattaggtgctgtgctca
13981 ---------+---------+---------+---------+---------+---------+ 14040
      caggtgcaattcgtaaccaggagttttgtctcgaggagttttataatccacgacacgagt
```

Figure 1 – page 20

```
      ttacagaatcaaactgatcacactgattgaaacttcctcaatgaaattttcaatcaaca
14041 ---------+---------+---------+---------+---------+---------+ 14100
      aatgtcttagtttgactagtgtgactaactttgaaggagttactttaaaagttagttgt

      acatgcttcaaataaaagtcaaacagtgttccaaccacttgacttcaaaccaagtagatt
14101 ---------+---------+---------+---------+---------+---------+ 14160
      tgtacgaagtttattttcagtttgtcacaaggttggtgaactgaagtttggttcatctaa

      ttaggtttagaaacactaaaaaaaggtgtttcatttataaatacagaaggaacaaaaaca
14161 ---------+---------+---------+---------+---------+---------+ 14220
      aatccaaatctttgtgatttttttccacaaagtaaatatttatgtcttccttgtttttgt

      tcactgcatcaatccagaaattatcaaaatatttagaggacaagaaatataaaatttagt
14221 ---------+---------+---------+---------+---------+---------+ 14280
      agtgacgtagttaggtctttaatagttttataaatctcctgttctttatattttaaatca

      caactttgctgctttctcagttccttaaaatcccagagtatctgcaaatatagctaaaaa
14281 ---------+---------+---------+---------+---------+---------+ 14340
      gttgaaacgacgaaagagtcaaggaattttagggtctcatagacgtttatatcgattttt

      gtaccaactcttgaaagcctatattactagtcatttcccattgagtattttggaatttta
14341 ---------+---------+---------+---------+---------+---------+ 14400
      catggttgagaactttcggatataatgatcagtaaagggtaactcataaaaccttaaaat

      tttatgttctacttatttattcatgtattctgctttatgatgtttatctgaataatctgg
14401 ---------+---------+---------+---------+---------+---------+ 14460
      aaatacaagatgaataaataagtacataagacgaaatactacaaatagacttattagacc

      acaaattctcattctgggcagtcattcgtttcatcctatgaatgccatggtgagggaaac
14461 ---------+---------+---------+---------+---------+---------+ 14520
      tgtttaagagtaagacccgtcagtaagcaaagtaggatacttacggtaccactccctttg

      agtgtagttagaggaacagatgaagtcagaacactcacatgcatcacggtcacagaactt
14521 ---------+---------+---------+---------+---------+---------+ 14580
      tcacatcaatctccttgtctacttcagtcttgtgagtgtacgtagtgccagtgtcttgaa

      taagtcacaagacagaaaagaaatcgattctgctttggatcaaagtttatagaacactac
14581 ---------+---------+---------+---------+---------+---------+ 14640
      attcagtgttctgtcttttctttagctaagacgaaacctagtttcaaatatcttgtgatg

      ttaatggaaactagtggaaatggctgctaaaggaaaagttaaggtgaatgatccaagctg
14641 ---------+---------+---------+---------+---------+---------+ 14700
      aattacctttgatcacctttaccgacgatttccttttcaattccacttactaggttcgac

      acttgattactgaatccagaacaaaattatgctaaatctctctggtaattaactaaataa
14701 ---------+---------+---------+---------+---------+---------+ 14760
      tgaactaatgacttaggtcttgttttaatacgatttagagagaccattaattgatttatt

      aaatcattttatactattatttagtaagttagtaaaggcgtgctactcattagatgctaa
14761 ---------+---------+---------+---------+---------+---------+ 14820
      tttagtaaaatatgataataaatcattcaatcatttccgcacgatgagtaatctacgatt
```

Figure 1 – page 21

```
         tctcatttactgaggaacacagaattgtatatgttttctggctctattatttattacttg
14821 ---------+---------+---------+---------+---------+---------+ 14880
         agagtaaatgactccttgtgtcttaacatatacaaaagaccgagataataaataatgaac

         ggtaaacttgaacaagtcaccaaaattcgttgggttacagtttgttctactgtaaaagca
14881 ---------+---------+---------+---------+---------+---------+ 14940
         ccatttgaacttgttcagtggttttaagcaacccaatgtcaaacaagatgacattttcgt

         gggataataatacttactttgcagaattctataaggattagcaataatgtagcaaaaca
14941 ---------+---------+---------+---------+---------+---------+ 15000
         ccctattattatgaatgaaacgtcttaaagatattcctaatcgttattacatcgttttgt

         ctgggtacatactgcaagttcagtgaaaagaagatactgtcattatttgttccaaaagtg
15001 ---------+---------+---------+---------+---------+---------+ 15060
         gacccatgtatgacgttcaagtcacttttcttctatgacagtaataaacaaggttttcac

         gaagaacttactattaatatttcatttttctgatttatttatttatctattttagagaca
15061 ---------+---------+---------+---------+---------+---------+ 15120
         cttcttgaatgataattataaagtaaaaagactaaataaataaatagataaaatctctgt

         aagtctctctctgtcacccatgctggagtgtagtggcacagtcatagctcactgtaacct
15121 ---------+---------+---------+---------+---------+---------+ 15180
         ttcagagagagacagtgggtacgacctcacatcaccgtgtcagtatcgagtgacattgga

         caaactcctgggctcaagcgattctcccatctcagcctcccaagtagctgggactacagg
15181 ---------+---------+---------+---------+---------+---------+ 15240
         gtttgaggacccgagttcgctaagagggtagagtcggagggttcatcgaccctgatgtcc

         catgtgtcaccatgcctggctaatttttatttttatttttttgttggtgagacaggttt
15241 ---------+---------+---------+---------+---------+---------+ 15300
         gtacacagtggtacggaccgattaaaaataaaaataaaaaaacaaccactctgtccaaa

         tttttttttttctttttgagaccaagtctcgctctgtcactcaggctggagtgcagtgg
15301 ---------+---------+---------+---------+---------+---------+ 15360
         aaaaaaaaaaagaaaaaactctggttcagagcgagacagtgagtccgacctcacgtcacc

         cccgatctcggctcactgcaagctccacctcccgggttcacgccattctcctgccttagc
15361 ---------+---------+---------+---------+---------+---------+ 15420
         gggctagagccgagtgacgttcgaggtggagggcccaagtgcggtaagaggacggaatcg

         ctcccaagtagctgggactacaggtgcccgccaccacacccggctaatttttgtatttt
15421 ---------+---------+---------+---------+---------+---------+ 15480
         gagggttcatcgaccctgatgtccacgggcggtggtgtgggccgattaaaaacataaaa

         tagtagagttgggatttcaccgtgttagccaggatggtctcaatctcctggcctcgtgat
15481 ---------+---------+---------+---------+---------+---------+ 15540
         atcatctcaaccctaaagtggcacaatcggtcctaccagagttagaggaccggagcacta

         ccacccgcctcggcctcccaaagtgctgggattacaggcgtgagccaccactcccggcca
15541 ---------+---------+---------+---------+---------+---------+ 15600
         ggtgggcggagccggagggtttcacgaccctaatgtccgcactcggtggtgagggccggt
```

Figure 1 – page 22

```
      agacaggttcttatattgcccaggctggtcttgaactcctggcctcaagcaattctccca
15601 ---------+---------+---------+---------+---------+---------+ 15660
      tctgtccaagaatataacgggtccgaccagaacttgaggaccggagttcgttaagagggt

      cctcagcctcccaaagttgcaagcatgtgtcactgtgcctggcttcttctgatttttttg
15661 ---------+---------+---------+---------+---------+---------+ 15720
      ggagtcggagggtttcaacgttcgtacacagtgacacggaccgaagaagactaaaaaaac

      gtctaaatagcatctccagatttctttttttttttaatttaaaaatgtatttatttct
15721 ---------+---------+---------+---------+---------+---------+ 15780
      cagatttatcgtagaggtctaaagaaaaaaaaaaaattaaatttttacataaataaaga

      ttatttagacacagggtcttgctatgttgcccacactggggtacactggctattcacagg
15781 ---------+---------+---------+---------+---------+---------+ 15840
      aataaatctgtgtcccagaacgatacaacgggtgtgaccccatgtgaccgataagtgtcc

      tgtaagcatagcccactatagtcttgaactcctggcctcaagggatccttccacctcagc
15841 ---------+---------+---------+---------+---------+---------+ 15900
      acattcgtatcgggtgatatcagaacttgaggaccggagttccctaggaaggtggagtcg

      cttccaagtctgggactacatctggctaagcatcttcaaatttcttatttatttatttat
15901 ---------+---------+---------+---------+---------+---------+ 15960
      gaaggttcagaccctgatgtagaccgattcgtagaagtttaaagaataaataaataaata

      ttatttttgagatggagtcttgctctgttgcctaggctggagtgcagtgactcaatctca
15961 ---------+---------+---------+---------+---------+---------+ 16020
      aataaaaactctacctcagaacgagacaacggatccgacctcacgtcactgagttagagt

      gctcactgcaacctctgcctcctgggttcaagccgattctcctgccttagcctctcgagt
16021 ---------+---------+---------+---------+---------+---------+ 16080
      cgagtgacgttggagacggaggacccaagttcggctaagaggacggaatcggagagctca

      agcagggattacaggcgtgtgccaccacacccagctaattttttatattttttattagagac
16081 ---------+---------+---------+---------+---------+---------+ 16140
      tcgtccctaatgtccgcacacggtggtgtgggtcgattaaaaatataaaaataatctctg

      agggtttcaccatgttggccaggctggtctcgaactcctgacctcaggtaatctacccgc
16141 ---------+---------+---------+---------+---------+---------+ 16200
      tcccaaagtggtacaaccggtccgaccagagcttgaggactggagtccattagatgggcg

      ctcggcctcccaaagtgctgggattacaggcgtgagccactgtgcccggctgcatcttca
16201 ---------+---------+---------+---------+---------+---------+ 16260
      gagccggagggtttcacgaccctaatgtccgcactcggtgacacgggccgacgtagaagt

      aatttcttaaatactccttggtatagtggagcccttaatgcttttcactaatgcactgct
16261 ---------+---------+---------+---------+---------+---------+ 16320
      ttaaagaatttatgaggaaccatatcacctcgggaattacgaaaagtgattacgtgacga

      ccttgatgtgctgcctattccagtagatacacagaatcagagtggtaagggcctttgaaa
16321 ---------+---------+---------+---------+---------+---------+ 16380
      ggaactacacgacggataaggtcatctatgtgtcttagtctcaccattcccggaaacttt
```

Figure 1 – page 23

```
      ccattgatttgttctagtggctttcaaaaaccattttaatacaattattttttaagcaa
16381 ---------+---------+---------+---------+---------+---------+ 16440
      ggtaactaaacaagatcaccgaaagtttttggtaaaattatgttaataaaaaattcgtt

      aatgtttatatatatatatatatggtttttttttttgagatggagtcttgctctgtt
16441 ---------+---------+---------+---------+---------+---------+ 16500
      ttacaaaatatatatatatatataccaaaaaaaaaaaaactctacctcagaacgagacaa

      gcccaggctagagtgcagtggtgcaatctcggctcactgcaacctcagcctccctggttc
16501 ---------+---------+---------+---------+---------+---------+ 16560
      cgggtccgatctcacgtcaccacgttagagccgagtgacgttggagtcggagggaccaag

      aagtgattttcctgcctcagcctccccagtagcttggactacaggtgggtgccaacgcac
16561 ---------+---------+---------+---------+---------+---------+ 16620
      ttcactaaaaggacggagtcggaggggtcatcgaacctgatgtccacccacggttgcgtg

      ctggctaattttgcatttttagtagagacagggtttcaccatgttggccaggctggtct
16621 ---------+---------+---------+---------+---------+---------+ 16680
      gaccgattaaaaacgtaaaaatcatctctgtcccaaagtggtacaaccggtccgaccaga

      taaactcctgacctcaggtgatctgcccacctcggcctcccaaagtactaggattataga
16681 ---------+---------+---------+---------+---------+---------+ 16740
      atttgaggactggagtccactagacgggtggagccggagggtttcatgatcctaatatct

      tgtgagccactgtgcccagccagaaatgcactttaaaaaccaccagtccttgcctgggca
16741 ---------+---------+---------+---------+---------+---------+ 16800
      acactcggtgacacgggtcggtctttacgtgaaatttttggtggtcaggaacggacccgt

      tggtggctcacacctgtaatcccagcactttgggaggctgaggcgggtggattacctgag
16801 ---------+---------+---------+---------+---------+---------+ 16860
      accaccgagtgtggacattagggtcgtgaaaccctccgactccgcccacctaatggactc

      gtcaggagttcgagaccagcctgatcaacatgatgaaaccctgtctctactaaaaataca
16861 ---------+---------+---------+---------+---------+---------+ 16920
      cagtcctcaagctctggtcggactagttgtactactttgggacagagatgatttttatgt

      aaaattagccgggcgtggtggcgtgtgcctgttatcccagctactcgagaggctaaggca
16921 ---------+---------+---------+---------+---------+---------+ 16980
      ttttaatcggcccgcaccaccgcacacggacaatagggtcgatgagctctccgattccgt

      ggagaatcggcttgaacccaggaggcagaggttgcagtgagctgagattgagtcactgca
16981 ---------+---------+---------+---------+---------+---------+ 17040
      cctcttagccgaacttgggtcctccgtctccaacgtcactcgactctaactcagtgacgt

      ctccagcctgggcaacagagcaagacttcatctcaaaaacaaacaaacaaagaaaaaacc
17041 ---------+---------+---------+---------+---------+---------+ 17100
      gaggtcggacccgttgtctcgttctgaagtagagtttttgtttgtttgtttctttttttgg

      cccaatagtccaaagccctaatttccccccattatttattttttaatgggcaaatttt
17101 ---------+---------+---------+---------+---------+---------+ 17160
      gggttatcaggtttcgggattaaaggggggtaataaataaaaaaattacccgtttaaaa
```

Figure 1 – page 24

```
       aaaaattgtatatatatttatggtgtacaatgggatgttttgacatatgtatacattatg
17161 ---------+---------+---------+---------+---------+---------+ 17220
       tttttaacatatatataaataccacatgttaccctacaaaactgtatacatatgtaatac

       gaatgactaaatcaagataattaaaatgcattacctcacatactcaccatttatttgtga
17221 ---------+---------+---------+---------+---------+---------+ 17280
       cttactgatttagttctattaattttacgtaatggagtgtatgagtggtaaataaacact

       tgagatcaaagtctactcttttagcaatttttcttttttcttttcttttctttctttattt
17281 ---------+---------+---------+---------+---------+---------+ 17340
       actctagtttcagatgagaaaatcgttaaaagaaaaaagaaaagaaaagaaagaaataaa

       ctttttttttttttttgaggcagaatcttgctctgtcgcccaggctggagtgcagtggc
17341 ---------+---------+---------+---------+---------+---------+ 17400
       gaaaaaaaaaaaaaaaactccgtcttagaacgagacagcgggtccgacctcacgtcaccg

       acaatctcggctcactgcaacctccacctctcaggttcaagcgattatcctgcctcagcc
17401 ---------+---------+---------+---------+---------+---------+ 17460
       tgttagagccgagtgacgttggaggtggagagtccaagttcgctaataggacggagtcgg

       ttccaagtagctgggactataggtgtgtgctaccacacccagctaatttttgtatttttt
17461 ---------+---------+---------+---------+---------+---------+ 17520
       aaggttcatcgaccctgatatccacacacgatggtgtgggtcgattaaaaacataaaaa

       agtagagatggagtttcaccatgttggccaggctggtcttgaactcctgacctcaggtga
17521 ---------+---------+---------+---------+---------+---------+ 17580
       tcatctctacctcaaagtggtacaaccggtccgaccagaacttgaggactggagtccact

       tccccctgcttcagcctcccaaagtgctgggattacaggcgcgaggtgcccagccttta
17581 ---------+---------+---------+---------+---------+---------+ 17640
       agggggacgaagtcggagggtttcacgaccctaatgtccgcgctccacgggtcggaaaat

       gcaatttccaatacattgttattaactatagtcaccatgttgtataatagatctctttaa
17641 ---------+---------+---------+---------+---------+---------+ 17700
       cgttaaaggttatgtaacaataattgatatcagtggtacaacatattatctagagaaatt

       cttattcctgataactgaaattttgtatcctttaaccaacatctatcctgttccacccct
17701 ---------+---------+---------+---------+---------+---------+ 17760
       gaataaggactattgactttaaaacataggaaattggttgtagataggacaaggtgggga

       gccctcccacccctacccccagcccctggtaagagcctctactcttcacctctatgagt
17761 ---------+---------+---------+---------+---------+---------+ 17820
       cgggagggtgggggatgggggtcggggaccattctcggagatgagaagtggagatactca

       tcaacttttgaaattccacatataatctagcgaggttatgcagtatttgtttttcagtg
17821 ---------+---------+---------+---------+---------+---------+ 17880
       agttgaaaactttaaggtgtatattagatcgctccaatacgtcataaacaaaaagtcac

       cctgcagatatgacattttgggttcaacttttgtttgtttttgagatggaatctcact
17881 ---------+---------+---------+---------+---------+---------+ 17940
       ggacgtctatactgtaaaacccaagttgaaaacaaacaaaaactctaccttagagtga
```

Figure 1 – page 25

```
      cttgtcgcccaggctggagtgcagtggcgtgatcttggctcactgcaatctccgcctcct
17941 ---------+---------+---------+---------+---------+---------+ 18000
      gaacagcgggtccgacctcacgtcaccgcactagaaccgagtgacgttagaggcggagga

      gggttcaagccattctcctgtctcagcctcctgagtagcagggattacaggcgcctgcca
18001 ---------+---------+---------+---------+---------+---------+ 18060
      cccaagttcggtaagaggacagagtcggaggactcatcgtccctaatgtccgcggacggt

      ccgtgcccagctaattttgtatttttagtagagacggggtttcactatgttggccaggc
18061 ---------+---------+---------+---------+---------+---------+ 18120
      ggcacgggtcgattaaaacataaaaatcatctctgccccaaagtgatacaaccggtccg

      tggtctctaactcctgacctcagacgatctgcctgcattggcctccaaaactgctgggat
18121 ---------+---------+---------+---------+---------+---------+ 18180
      accagagattgaggactggagtctgctagacggacgtaaccggaggttttgacgacccta

      tacaggcatgagacactgcgaccggccaaacattttttaatgcataatagatgtacata
18181 ---------+---------+---------+---------+---------+---------+ 18240
      atgtccgtactctgtgacgctggccggtttgtaaaaaattacgtattatctacatgtat

      ctttcagggcacatctgataatttaatatattcatataatttgtacagatcaagtcaatg
18241 ---------+---------+---------+---------+---------+---------+ 18300
      gaaagtcccgtgtagactattaaattatataagtatattaaacatgtctagttcagttac

      taactggtatatccatcgccttaaacatttgtcttttctttattctaggaacccatttga
18301 ---------+---------+---------+---------+---------+---------+ 18360
      attgaccatataggtagcggaatttgtaaacagaaaagaaataagatccttgggtaaact

      attattcttttctagctattttgaaatatacaatagattattgtgaactatagtcaccct
18361 ---------+---------+---------+---------+---------+---------+ 18420
      taataagaaaagatcgataaaactttatatgttatctaataacacttgatatcagtggga

      actgatccatcgaacactaggtcttatttcttcttattaaactggattttgtactcatta
18421 ---------+---------+---------+---------+---------+---------+ 18480
      tgactaggtagcttgtgatccagaataaagaagaataatttgacctaaaacatgagtaat

      atcaagctctcttcatcctccccactctacctggcgtctggtaaccaccaatctactctc
18481 ---------+---------+---------+---------+---------+---------+ 18540
      tagttcgagagaagtaggaggggtgagatggaccgcagaccattggtggttagatgagag

      tattatcatgaggtccactttttagctcccacatatcagcgagaacatgtaatattcgt
18541 ---------+---------+---------+---------+---------+---------+ 18600
      ataatagtactccaggtgaaaaatcgagggtgtatagtcgctcttgtacattataagca

      ctttttgaggttggcttatttctcttaacataatgacctgcagttccatgcatgttgctg
18601 ---------+---------+---------+---------+---------+---------+ 18660
      gaaaaactccaaccgaataaagagaattgtattactggacgtcaaggtacgtacaacgac

      caggtgacaggatttccttcttttattttattttattttatttttttgagacagagtctt
18661 ---------+---------+---------+---------+---------+---------+ 18720
      gtccactgtcctaaaggaagaaaataaaataaaataaaataaaaaaactctgtctcagaa
```

Figure 1 – page 26

```
      actctgtctcccaggttggagtgcagtggcgtgatcttggctcactgaaacctccggctg
18721 ---------+---------+---------+---------+---------+---------+ 18780
      tgagacagagggtccaacctcacgtcaccgcactagaaccgagtgactttggaggccgac

      ccaggttcaagtaattctcctgcctcagcctcctgagtagctgggactacaggcgcgtgc
18781 ---------+---------+---------+---------+---------+---------+ 18840
      ggtccaagttcattaagaggacggagtcggaggactcatcgaccctgatgtccgcgcacg

      caccacacccaactaattttttttttttttttttttttttttttttttttttttttttttt
18841 ---------+---------+---------+---------+---------+---------+ 18900
      gtggtgtgggttgattaaaaaaaaaaaaaaaaaaaaaaaaaaaaaaaaaaaaaaaaaaaaa

      tttttttgagacggagtctcgctctgtcgcccaggctggagtgcagtggcgggatctcg
18901 ---------+---------+---------+---------+---------+---------+ 18960
      aaaaaaaactctgcctcagagcgagacagcgggtccgacctcacgtcaccgccctagagc

      gctcactgcaagctccgcctcccgggttcacgccattctcctgcctcagcctcccaagta
18961 ---------+---------+---------+---------+---------+---------+ 19020
      cgagtgacgttcgaggcggagggcccaagtgcggtaagaggacggagtcggagggttcat

      gctgggactacaggcgcccgccactacgcccggctaatttttgtatttttagtagagac
19021 ---------+---------+---------+---------+---------+---------+ 19080
      cgaccctgatgtccgcgggcggtgatgcgggccgattaaaaacataaaaatcatctctg

      ggggtttcaccgttttagccgggatggtctcgatctcctgacctcgtgatccgcccgcct
19081 ---------+---------+---------+---------+---------+---------+ 19140
      ccccaaagtggcaaaatcggccctaccagagctagaggactggagcactaggcgggcgga

      cggcctcccaaagtgctgggattacaggcgtgagccaccgcgcccggcccactaattttt
19141 ---------+---------+---------+---------+---------+---------+ 19200
      gccggagggtttcacgaccctaatgtccgcactcggtggcgcgggccgggtgattaaaaa

      gtatttttagtagagatggggtttcacatgttggcaaggctggtctcgaactcctgacct
19201 ---------+---------+---------+---------+---------+---------+ 19260
      cataaaaatcatctctaccccaaagtgtacaaccgttccgaccagagcttgaggactgga

      caggtgatccgcctgcctcggcctcccaaagtgctgggattacaggcttgggccaccgca
19261 ---------+---------+---------+---------+---------+---------+ 19320
      gtccactaggcggacggagccggagggtttcacgaccctaatgtccgaacccggtggcgt

      ccaggccaggatttccttctttttcaagtctgaatagtattccagtgtgtacatatacta
19321 ---------+---------+---------+---------+---------+---------+ 19380
      ggtccggtcctaaaggaagaaaaagttcagacttatcataaggtcacacatgtatatgat

      ctacgttttctttatccgttcatctgtttgagtcttctttttttcttagtttagctaaag
19381 ---------+---------+---------+---------+---------+---------+ 19440
      gatgcaaaagaaataggcaagtagacaaactcagaagaaaaaaagaatcaaatcgatttc

      atttattttatttttcaaaaactaatttttcatttgttgatcttctgtattttttta
19441 ---------+---------+---------+---------+---------+---------+ 19500
      taaataaaataaaaagtttttgattaaaaagtaaacaactagaagacataaaaaaat
```

Figure 1 – page 27

```
      gtctcaatttcatttatttctgctgtgatgttctttctttccttctactaattttgagtt
19501 ---------+---------+---------+---------+---------+---------+ 19560
      cagagttaaagtaaataaagacgacactacaagaaagaaaggaagatgattaaaactcaa

      tgatttgttcttgcttttatagttccctcatgggcattactaggttgtttatttgaagtc
19561 ---------+---------+---------+---------+---------+---------+ 19620
      actaaacaagaacgaaaatatcaagggagtacccgtaatgatccaacaaataaacttcag

      tgttccttctttccttcattccttccttcctccctccctccctccctcccttcttccttc
19621 ---------+---------+---------+---------+---------+---------+ 19680
      acaaggaagaaaggaagtaaggaaggaaggagggagggagggagggagggaagaaggaag

      cttccattctttcttttttttttgagagggaatctcgctctgttgcccaggttggagtgc
19681 ---------+---------+---------+---------+---------+---------+ 19740
      gaaggtaagaaagaaaaaaaaaactctcccttagagcgagacaacgggtccaacctcacg

      agtggcgcgatctcagctcactgcaacctccacctcccgggttcaagcaattctcctgtc
19741 ---------+---------+---------+---------+---------+---------+ 19800
      tcaccgcgctagagtcgagtgacgttggaggtggagggcccaagttcgttaagaggacag

      tcagcctcccaagtagctgggattacaggcatgcaccaccacgcctggctaatttttttg
19801 ---------+---------+---------+---------+---------+---------+ 19860
      agtcggagggttcatcgaccctaatgtccgtacgtggtggtgcggaccgattaaaaaaac

      tatttttagtagagacggggtttcaccatattggccaggctggtcttgaactcctgactc
19861 ---------+---------+---------+---------+---------+---------+ 19920
      ataaaaatcatctctgccccaaagtggtataaccggtccgaccagaacttgaggactgag

      tgcccgcctcagcctcccaaagttctgggattacaggtgttagccattgtgcccggccct
19921 ---------+---------+---------+---------+---------+---------+ 19980
      acgggcggagtcggagggtttcaagaccctaatgtccacaatcggtaacacgggccggga

      tctttcctttcttcttctttctttctcagggtctcactctgtcacctggactggagtgca
19981 ---------+---------+---------+---------+---------+---------+ 20040
      agaaaggaaagaagaagaaagaaagagtcccagagtgagacagtggacctgacctcacgt

      gtggtgcaatcatggctcacagcagctttgacctcctgggctcaggcaatcctcctaccc
20041 ---------+---------+---------+---------+---------+---------+ 20100
      caccacgttagtaccgagtgtcgtcgaaactggaggacccgagtccgttaggaggatggg

      cagcatcccaagtagctgggactaaggctaccatgcctggctgattttgtattttctgt
20101 ---------+---------+---------+---------+---------+---------+ 20160
      gtcgtagggttcatcgaccctgattccgatggtacggaccgactaaaacataaaagaca

      agagacaggctttcaccatgttgcccagtctgctcttgaactcctgggctcaagcaatcc
20161 ---------+---------+---------+---------+---------+---------+ 20220
      tctctgtccgaaagtggtacaacgggtcagacgagaacttgaggacccgagttcgttagg

      acctgccttggcctcccaaagtgctgagatcttatttgaaatctttcaactttttgata
20221 ---------+---------+---------+---------+---------+---------+ 20280
      tggacggaaccggagggtttcacgactctagaataaactttagaaagttgaaaaaactat
```

Figure 1 – page 28

```
       taggcattacttgaaatctttctactttttgatataggcatttattgctataaactttc
20281 ---------+---------+---------+---------+---------+---------+ 20340
       atccgtaatgaactttagaaagatgaaaaactatatccgtaaataacgatatttgaaag

       ctcttagtgctgcttctgctgtatcccatagattttgcatgttgtatttccattttcat
20341 ---------+---------+---------+---------+---------+---------+ 20400
       gagaatcacgacgaagacgacatagggtatctaaaacgtacaacataaaggtaaaagta

       ctgtttcaagatattttaaatttttctcctaatttcttcatggacccattggctattcag
20401 ---------+---------+---------+---------+---------+---------+ 20460
       gacaaagttctataaaatttaaaaagaggattaaagaagtacctgggtaaccgataagtc

       gagcatgttgtttaatttccatgtgtttgtgtattttccaaggttcttgttattgatttc
20461 ---------+---------+---------+---------+---------+---------+ 20520
       ctcgtacaacaaattaaaggtacacaaacacataaaaggttccaagaacaataactaaag

       taattttattccatagtggtgagaaagatacttgttatgatgtctacttttctgaatttg
20521 ---------+---------+---------+---------+---------+---------+ 20580
       attaaaataaggtatcaccactctttctatgaacaatactacagatgaaaagacttaaac

       ttaagacttgttttgtggcctaagatatagtctatgctggagaatgttccatgtgctatt
20581 ---------+---------+---------+---------+---------+---------+ 20640
       aattctgaacaaaacaccggattctatatcagatacgacctcttacaaggtacacgataa

       gagcagaatgtctattctgcagcagttgagtaaaatgctctgtgaatgtcagctaggcct
20641 ---------+---------+---------+---------+---------+---------+ 20700
       ctcgtcttacagataagacgtcgtcaactcattttacgagacacttacagtcgatccgga

       atttgagctagtatatagtttaatgtttctttattattttctgtctggatgatctgtttt
20701 ---------+---------+---------+---------+---------+---------+ 20760
       taaactcgatcatatatcaaattacaaagaaataataaaagacagacctactagacaaaa

       actgagagtgaggtgtggtgttagagtcccctactactattgcattacagtatatctctt
20761 ---------+---------+---------+---------+---------+---------+ 20820
       tgactctcactccacaccacaatctcaggggatgatgataacgtaatgtcatatagagaa

       cttttagatctattaatgtttgctttatatactttggagctccaatgttgagtgcaaaga
20821 ---------+---------+---------+---------+---------+---------+ 20880
       gaaaatctagataattacaaacgaaatatatgaaacctcgaggttacaactcacgtttct

       tacttatatcttcttgctgaattgacccctttatcattatatagtaaccttctttgcctc
20881 ---------+---------+---------+---------+---------+---------+ 20940
       atgaatatagaagaacgacttaactggggaaatagtaatatatcattggaagaaacggag

       tttgacagccttgattcacagtctgttttatctgatgtaagtatagctactcctgttctt
20941 ---------+---------+---------+---------+---------+---------+ 21000
       aaactgtcggaactaagtgtcagacaaaatagactacattcatatcgatgaggacaagaa

       ttttggtttccagttgcttggaatgtctttttccacccccttaacttccagtatttttat
21001 ---------+---------+---------+---------+---------+---------+ 21060
       aaaaccaaaggtcaacgaaccttacagaaaaaggtggggaattgaaggtcataaaaata
```

Figure 1 – page 29

```
      aagtaaagtaggtttcttgtaggcagcatataatttggtcccattttgtatccattcag
21061 ---------+---------+---------+---------+---------+---------+ 21120
      ttcatttcatccaaagaacatccgtcgtatattaaaccagggtaaaacataggtaagtc

      ccactctattccttttttttgggggggttcccaagttttattcaagaactcataccaaa
21121 ---------+---------+---------+---------+---------+---------+ 21180
      ggtgagataaggaaaaaaaacccccccaagggttcaaaataagttcttgagtatggttt

      tattccagataaataaattttatcttcaccttcctcctcttctttttccaggttaatct
21181 ---------+---------+---------+---------+---------+---------+ 21240
      ataaggtctatttatttaaaatagaagtggaaggaggagaagaaaaaggtccaattaga

      ggaattaacgtcattcataataactctttttgctgttagcaactacacacaacaaatcac
21241 ---------+---------+---------+---------+---------+---------+ 21300
      ccttaattgcagtaagtattattgagaaaaacgacaatcgttgatgtgtgttgtttagtg

      atagattattcttcaaatatttttggtgagatatttcaaatacctttggaaaaaggta
21301 ---------+---------+---------+---------+---------+---------+ 21360
      tatctaataagaagtttataaaaaccactctataaagtttatggaaaacctttttccat

      cctcagaagtcacagtgatcttgctgttgctcctttcgatggttataatgctccaccaag
21361 ---------+---------+---------+---------+---------+---------+ 21420
      ggagtcttcagtgtcactagaacgacaacgaggaaagctaccaatattacgaggtggttc

      attcccagcttttccattcactttaatcctctcttgcaaaaactgctcaaaattggcagc
21421 ---------+---------+---------+---------+---------+---------+ 21480
      taagggtcgaaaaggtaagtgaaattaggagagaacgtttttgacgagttttaaccgtcg

      atctatgattccattttctacaaggtgggtacagtcaagagtgaacatcataacctgctt
21481 ---------+---------+---------+---------+---------+---------+ 21540
      tagatactaaggtaaaagatgttccacccatgtcagttctcacttgtagtattggacgaa

      ctttttttgcctctctttgccacaagctttttcacagcactatgcctcttaattggagaa
21541 ---------+---------+---------+---------+---------+---------+ 21600
      gaaaaaaacggagagaaacggtgttcgaaaaagtgtcgtgatacggagaattaacctctt

      ttgagtccatttacatttagtgttattattgatacataaagacttaacatttttttaaat
21601 ---------+---------+---------+---------+---------+---------+ 21660
      aactcaggtaaatgtaaatcacaataataactatgtatttctgaattgtaaaaaaattta

      tgatacataattgatgtagctattttggggcgttcatgtgataatttaatacattcatat
21661 ---------+---------+---------+---------+---------+---------+ 21720
      actatgtattaactacatcgataaaaccccgcaagtacactattaaattatgtaagtata

      aatttgtaaagattaaattagtgtaattgggatacctatcaccttcaatatttgtctttt
21721 ---------+---------+---------+---------+---------+---------+ 21780
      ttaaacatttctaatttaatcacattaaccctatggatagtggaagttataaacagaaaa

      cttttcttttttttctgtgagatggagttttgctttttttgcccaggctggagtgcaat
21781 ---------+---------+---------+---------+---------+---------+ 21840
      gaaaagaaaaaaaagacactctacctcaaaacgaaaaaaacgggtccgacctcacgtta
```

Figure 1 – page 30

```
      ggcgcaatctcggctcactgcaacctccacctcccgggttcaagcaattctcctgcctca
21841 ---------+---------+---------+---------+---------+---------+ 21900
      ccgcgttagagccgagtgacgttggaggtggagggcccaagttcgttaagaggacggagt

      gcctcccgagtagctgggattacaggcatgcaccaccatgctcagctaattttgtatttt
21901 ---------+---------+---------+---------+---------+---------+ 21960
      cggagggctcatcgaccctaatgtccgtacgtggtggtacgagtcgattaaaacataaaa

      tagtagagacggggtttaccatgttggtcaggctggtctcgaactcctgacctcaggtg
21961 ---------+---------+---------+---------+---------+---------+ 22020
      atcatctctgccccaaaatggtacaaccagtccgaccagagcttgaggactggagtccac

      atccactcgccctggcctaccaaagtgctgggattataggcatgagccaccacacctggc
22021 ---------+---------+---------+---------+---------+---------+ 22080
      taggtgagcgggaccggatggtttcacgaccctaatatccgtactcggtggtgtggaccg

      cctgtcttttctttatgttggaaacattcaaattattctcttctagctattttgaaatat
22081 ---------+---------+---------+---------+---------+---------+ 22140
      ggacagaaaagaaatacaacctttgtaagtttaataagagaagatcgataaaactttata

      acaatatattattgtaaactagtcactttactgatatatcaaacactaggtcttatttct
22141 ---------+---------+---------+---------+---------+---------+ 22200
      tgttatataataacatttgatcagtgaaatgactatatagtttgtgatccagaataaaga

      ttcatcaaaccctatatatatatatatatatatatatatatattttttttttttttttg
22201 ---------+---------+---------+---------+---------+---------+ 22260
      aagtagtttgggatatatatatatatatatatatatatatataaaaaaaaaaaaaaaac

      agacggagtctcgctctgtctcgctctgtcgcccaggctagagtgcagtggcacaatctc
22261 ---------+---------+---------+---------+---------+---------+ 22320
      tctgcctcagagcgagacagagcgagacagcgggtccgatctcacgtcaccgtgttagag

      ggcccactgcaagctccgcctcccgggttcatgccattctcctgcctcagcgccccgagt
22321 ---------+---------+---------+---------+---------+---------+ 22380
      ccgggtgacgttcgaggcggagggcccaagtacggtaagaggacggagtcgcggggctca

      agctgggactacaggtgcctgccaccatgcccggctaatttttgtatttttagtagaga
22381 ---------+---------+---------+---------+---------+---------+ 22440
      tcgaccctgatgtccacggacggtggtacgggccgattaaaaacataaaaatcatctct

      cggggtttaccatgttagccaggatggtctcaatctcctgaccttgtgatccacccacc
22441 ---------+---------+---------+---------+---------+---------+ 22500
      gccccaaaatggtacaatcggtcctaccagagttagaggactggaacactaggtgggtgg

      tcggcctcccaaagtgctgggattacaggcttgagccaccgtgcccggccaaaccctata
22501 ---------+---------+---------+---------+---------+---------+ 22560
      agccggagggtttcacgaccctaatgtccgaactcggtggcacgggccggtttgggatat

      tttataaccattaatcaacttctctttatctcccccattctgtaccctttctggcctttg
22561 ---------+---------+---------+---------+---------+---------+ 22620
      aaatattggtaattagttgaagagaaatagagggggtaagacatgggaaagaccggaaac
```

Figure 1 – page 31

```
      gtaactatcaatatactctctatcttaatgagttccactttttttagcttccacatatca
22621 ---------+---------+---------+---------+---------+---------+ 22680
      cattgatagttatatgagagatagaattactcaaggtgaaaaaaatcgaaggtgtatagt

      gtgagaacatatgatatttgtctttctgtgtttgccttatttctcttaacatgacctgca
22681 ---------+---------+---------+---------+---------+---------+ 22740
      cactcttgtatactataaacagaaagacacaaacggaataaagagaattgtactggacgt

      gttccatgcatcttgctgcaaatgacaggatttccttctgttttaaaatctgaatagtat
22741 ---------+---------+---------+---------+---------+---------+ 22800
      caaggtacgtagaacgacgtttactgtcctaaaggaagacaaaattttagacttatcata

      tccattgtgtatatatgccacgttttcctcatccattcatccattgctggatgcttaggt
22801 ---------+---------+---------+---------+---------+---------+ 22860
      aggtaacacatatatacggtgcaaaaggagtaggtaagtaggtaacgacctacgaatcca

      tgattccatatcttggttattgtgattaatgctgcagtcaacattaggagtgcagatatt
22861 ---------+---------+---------+---------+---------+---------+ 22920
      actaaggtatagaaccaataacactaattacgacgtcagttgtaatcctcacgtctataa

      tccctgacatactgatttcatttcattcccttcccttcccctgcctgtctgcctgccttc
22921 ---------+---------+---------+---------+---------+---------+ 22980
      agggactgtatgactaaagtaaagtaagggaagggaaggggacggacagacggacggaag

      cttccttccttccttccttccttcctttcttccttccttccttcccttcctccctccacc
22981 ---------+---------+---------+---------+---------+---------+ 23040
      gaaggaaggaaggaaggaaggaaggaaagaaggaaggaaggaagggaaggagggaggtgg

      ccccccgcccctttcagatggaatctggctctgtcgcccaggctggagtgcagtggcgca
23041 ---------+---------+---------+---------+---------+---------+ 23100
      ggggggcggggaaagtctaccttagaccgagacagcgggtccgacctcacgtcaccgcgt

      atctcagctcactacaacctccgcctcctgggttcaagcaattcttctgcctcagcctcc
23101 ---------+---------+---------+---------+---------+---------+ 23160
      tagagtcgagtgatgttggaggcggaggacccaagttcgttaagaagacggagtcggagg

      cgagtagctgggattacgggcatgtgccgccatacccagctaatttttttgtatttttag
23161 ---------+---------+---------+---------+---------+---------+ 23220
      gctcatcgaccctaatgcccgtacacggcggtatgggtcgattaaaaaaacataaaaatc

      tagaggcagggttttaccatattggccaggctggtctcgaactcctgacctcatgatcca
23221 ---------+---------+---------+---------+---------+---------+ 23280
      atctccgtcccaaaatggtataaccggtccgaccagagcttgaggactggagtactaggt

      cctgcctcagcctcccaaagtgctgggattacataggtgtgagccaccgtacacagccag
23281 ---------+---------+---------+---------+---------+---------+ 23340
      ggacggagtcggagggtttcacgaccctaatgtatccacactcggtggcatgtgtcggtc

      tttcattttcttttctttttttttttttttgagacggagtctcgctctgttgcccaggc
23341 ---------+---------+---------+---------+---------+---------+ 23400
      aaagtaaaagaaaagaaaaaaaaaaaaaaaactctgcctcagagcgagacaacgggtccg
```

Figure 1 – page 32

```
      tggagtgctggagtgcagtggcacgatctcggctcactgcaagctccacctcccgggttc
23401 ---------+---------+---------+---------+---------+---------+ 23460
      acctcacgacctcacgtcaccgtgctagagccgagtgacgttcgaggtggagggcccaag

      acaccattctcctgcctcagcctcccaagtagctgggacaacaggcgcctgccactatgt
23461 ---------+---------+---------+---------+---------+---------+ 23520
      tgtggtaagaggacggagtcggagggttcatcgaccctgttgtccgcggacggtgataca

      ccggctaatttttgtatttttttagtagagatggggtttcactgtgttagccaggatgg
23521 ---------+---------+---------+---------+---------+---------+ 23580
      ggccgattaaaaacataaaaaaatcatctctaccccaaagtgacacaatcggtcctacc

      tctcgatctcctgaccttgtgatcggcccacctcggcctcccagagtgctgggattacag
23581 ---------+---------+---------+---------+---------+---------+ 23640
      agagctagaggactggaacactagccgggtggagccggagggtctcacgaccctaatgtc

      gtgtgagccaccgcgcctggcccattttctttagatatatacccaagtaggggattgct
23641 ---------+---------+---------+---------+---------+---------+ 23700
      cacactcggtggcgcggaccgggtaaaagaaatctatatatgggttcatcccctaacga

      gggtcatatagtagttctattttaatttttgaggaatctccatactgtttcccataat
23701 ---------+---------+---------+---------+---------+---------+ 23760
      cccagtatatcatcaagataaaattaaaaactccttagaggtatgacaaagggtatta

      ggctgtactaatttaaattcccaccaacagtgtgtaaggattagtgctggtgaggatgtg
23761 ---------+---------+---------+---------+---------+---------+ 23820
      ccgacatgattaaatttaagggtggttgtcacacattcctaatcacgaccactcctacac
                                            I9(-50)
      gagaaaacgatacttctgggcatttttcttctattgagactaaagttgcaactcttagt
23821 ---------+---------+---------+---------+---------+---------+ 23880
      ctcttttgctatgaagacccgtaaaaagaagataactctgatttcaacgttgagaatca
                                                          917      Exon 10
      atttttttttatactaccctttaggaaggtgaaattgttgaagtggatgaagaaacagca
23881 ---------+---------+---------+---------+---------+---------+ 23940
      taaaaaaaaatatgatgggaaatccttccactttaacaacttcacctacttctttgtcgt

                               E  G  E  I  V  E  V  D  E  E  T  A  -

      gctatcttgaagaattcaagatttgctcaagatttctgatcagaccaattggagagaag
23941 ---------+---------+---------+---------+---------+---------+ 24000
      cgatagaacttcttaagttctaaacgagttctaaagactagtctggttaacctctcttc

      A  I  L  K  N  S  R  F  A  Q  D  F  L  I  R  P  I  G  E  K  -

      ttgccaacatctggaggctgttctgctttggagttaaaggttagtttggctttcactacc
24001 ---------+---------+---------+---------+---------+---------+ 24060
      aacggttgtagacctccgacaagacgaaacctcaatttccaatcaaaccgaaagtgatgg

      L  P  T  S  G  G  C  S  A  L  E  L  K

      tgagagaactattttatttatttattttgagatggagtctctctctgtcacccagactg
24061 ---------+---------+---------+---------+---------+---------+ 24120
      actctcttgataaaataaataaataaaaactctacctcagagagagacagtgggtctgac
```

Figure 1 – page 33

```
       gagtgcagtggtgtgatcttggctcactgcaacctccgcctcctgggttcaagcaattct
24121 ---------+---------+---------+---------+---------+---------+ 24180
       ctcacgtcaccacactagaaccgagtgacgttggaggcggaggacccaagttcgttaaga

       ccctgcctcagcctcccgattagctaagattacaggcacccaccaccacgcccggctaat
24181 ---------+---------+---------+---------+---------+---------+ 24240
       gggacggagtcggagggctaatcgattctaatgtccgtgggtggtggtgcgggccgatta

       ttttgtgtttttagtagagatggggtttcgccatgttggccaggctggtcttgaactcc
24241 ---------+---------+---------+---------+---------+---------+ 24300
       aaaacacaaaaaatcatctctaccccaaagcggtacaaccggtccgaccagaacttgagg

       tgacctcaggtaacccacctgcctcagtctcccaaagtgctgggattacaggcgtgagcc
24301 ---------+---------+---------+---------+---------+---------+ 24360
       actggagtccattgggtggacggagtcagagggtttcacgaccctaatgtccgcactcgg

       actgtgcccggccagtatgcatggtctcttgaggcgcacttctcttgctggtcaaatgtt
24361 ---------+---------+---------+---------+---------+---------+ 24420
       tgacacgggccggtcatacgtaccagagaactccgcgtgaagagaacgaccagtttacaa

       gttagacggttatataccagttaaacgccaccattttgcctcttaatgtgcatgcttgag
24421 ---------+---------+---------+---------+---------+---------+ 24480
       caatctgccaatatatggtcaatttgcggtggtaaaacggagaattacacgtacgaactc

       cccacttgcccaactcccgagatcttatcgggaagctgctgatcaccagtttcaggtgtt
24481 ---------+---------+---------+---------+---------+---------+ 24540
       gggtgaacgggttgagggctctagaatagcccttcgacgactagtggtcaaagtccacaa

       tctgtttattgggagacttcctttccctggtactgtctgtgactaattatgattttcgag
24541 ---------+---------+---------+---------+---------+---------+ 24600
       agacaaataaccctctgaaggaaagggaccatgacagacactgattaatactaaaagctc

       agacagttaacaaccacctgatcatcacctaatgatcgcctgacattcctggtggagtcg
24601 ---------+---------+---------+---------+---------+---------+ 24660
       tctgtcaattgttggtggactagtagtggattactagcggactgtaaggaccacctcagc

       gcgcggggagccctctcctgccctgctcacgcctgactagctattatacctgctttaaca
24661 ---------+---------+---------+---------+---------+---------+ 24720
       cgcgcccctcgggagaggacgggacgagtgcggactgatcgataatatggacgaaattgt

       agttctccaaaattcagagacctttcgtgagtattctgattttataataaaatagttatt
24721 ---------+---------+---------+---------+---------+---------+ 24780
       tcaagaggttttaagtctctggaaagcactcataagactaaaatattattttatcaataa

       tgcataagtttagtaagagtcttttctctcaaaacaggacaattggagacacttggttat
24781 ---------+---------+---------+---------+---------+---------+ 24840
       acgtattcaaatcattctcagaaaagagagttttgtcctgttaacctctgtgaaccaata

       tttaccaaagctttgactggaataacatttgtaggtaaagttccagcaaagccaacttga
24841 ---------+---------+---------+---------+---------+---------+ 24900
       aaatggtttcgaaactgaccttattgtaaacatccatttcaaggtcgtttcggttgaact
```

Figure 1 – page 34

```
      aaagagcctatctggccaaactcttgctggacttcatgcaaatgatcaggcaaagtttaa
24901 ---------+---------+---------+---------+---------+---------+ 24960
      tttctcggatagaccggtttgagaacgacctgaagtacgtttactagtccgtttcaaatt

      taagcctaaaatttattttgcacataaattggccttactataatttgtctttagtataaa
24961 ---------+---------+---------+---------+---------+---------+ 25020
      attcggattttaaataaaacgtgtatttaaccggaatgatattaaacagaaatcatattt

      aggaggagctgggtgcagaagttcacactcataatcccagcactttgggaggctgagaca
25021 ---------+---------+---------+---------+---------+---------+ 25080
      tcctcctcgacccacgtcttcaagtgtgagtattagggtcgtgaaaccctccgactctgt

      ggcagatcacttgaggccaggagtttgacaccagcctgggtaacatgttgaaaccctgtc
25081 ---------+---------+---------+---------+---------+---------+ 25140
      ccgtctagtgaactccggtcctcaaactgtggtcggacccattgtacaactttgggacag

      tctaccaaaaatacaaaaaaattatctgggtatggtggtgcatgctggtagttccagtta
25141 ---------+---------+---------+---------+---------+---------+ 25200
      agatggtttttatgtttttttaatagacccataccaccacgtacgaccatcaaggtcaat

      ctcaagaggctgagatgggaggattgcttgagcccagggaggtggagggcaatgagccaa
25201 ---------+---------+---------+---------+---------+---------+ 25260
      gagttctccgactctaccctcctaacgaactcgggtccctccacctcccgttactcggtt

      gactgcaccactgcactccagcctgggcaacagagtgagactctgtctcaaaaaaaaaaa
25261 ---------+---------+---------+---------+---------+---------+ 25320
      ctgacgtggtgacgtgaggtcggacccgttgtctcactctgagacagagttttttttttt

      aaaaaaaaaaaaaaagaaagaaggctagagagagaaatggtttcaaaggaaaactataac
25321 ---------+---------+---------+---------+---------+---------+ 25380
      tttttttttttttttctttcttccgatctctctctttaccaaagtttcctttgatattg

      acttgttactagatttccagcctggacttttgtttttgagtgcatattgaatcattaatt
25381 ---------+---------+---------+---------+---------+---------+ 25440
      tgaacaatgatctaaaggtcggacctgaaaacaaaaactcacgtataacttagtaattaa

      atttcttggctacaataaccctctaaagataaaccaggttataatttttcttcatgtttt
25441 ---------+---------+---------+---------+---------+---------+ 25500
      taaagaaccgatgttattgggagatttctatttggtccaatattaaaaagaagtacaaaa

      tagtttgtgccctaagtggaataggttccttattctgttctgacacacgaatactctttt
25501 ---------+---------+---------+---------+---------+---------+ 25560
      atcaaacacgggattcaccttatccaaggaataagacaagactgtgtgcttatgagaaaa

      gactgtcatattattaatgttatttatagctccttgttttacttccaaagaaaccagaat
25561 ---------+---------+---------+---------+---------+---------+ 25620
      ctgacagtataataattacaataaatatcgaggaacaaaatgaaggtttctttggtctta

      catgatattctaaggttagagaatcccccgtttggaatcccactggtcctaatctgcttt
25621 ---------+---------+---------+---------+---------+---------+ 25680
      gtactataagattccaatctcttagggggcaaaccttagggtgaccaggattagacgaaa
```

Figure 1 – page 35

```
      tcactgcaaattccgtgctgctaaaattatataagcactcttctctaggcccagggacct
25681 ---------+---------+---------+---------+---------+---------+ 25740
      agtgacgtttaaggcacgacgattttaatatattcgtgagaagagatccgggtccctgga

      atcacacaaaaggtaggtgtgtgagactgtaagggccagttttgagagaattatttcaga
25741 ---------+---------+---------+---------+---------+---------+ 25800
      tagtgtgttttccatccacacactctgacattcccggtcaaaactctcttaataaagtct

      ctctccaaatcaaaaatgggcacacagatgcataaacagctggtaaaataagggactctg
25801 ---------+---------+---------+---------+---------+---------+ 25860
      gagaggtttagtttttacccgtgtgtctacgtatttgtcgaccattttattccctgagac

      cctcctgggttattatgtgtgtggcaccttttcatccatcccaatcataaagaatttcct
25861 ---------+---------+---------+---------+---------+---------+ 25920
      ggaggacccaataatacacacaccgtggaaaagtaggtagggttagtatttcttaaagga

      gcttctcgtagaatgaaaagaaaattattactgagaggatataaaggtacctcatgtcaa
25921 ---------+---------+---------+---------+---------+---------+ 25980
      cgaagagcatcttacttttcttttaataatgactctcctatatttccatggagtacagtt

      agcctcctaggtttaatactctgagttatgagatttatgcagataacatatatattttt
25981 ---------+---------+---------+---------+---------+---------+ 26040
      tcggaggatccaaattatgagactcaatactctaaatacgtctattgtatatataaaaaa

      aaaattttagaacaggccaggcacagtggctcaagcctgtaatcctagcactttgggagg
26041 ---------+---------+---------+---------+---------+---------+ 26100
      ttttaaaatcttgtccggtccgtgtcaccgagttcggacattaggatcgtgaaaccctcc

      ccaaggtgggcagattgcctgagctcaggagttcaagaccagcctgggcaacatggtgac
26101 ---------+---------+---------+---------+---------+---------+ 26160
      ggttccacccgtctaacggactcgagtcctcaagttctggtcggacccgttgtaccactg

      accccatctctactaaaatacaaaaaataaattagatgggcatggtggcgtgcgcctgta
26161 ---------+---------+---------+---------+---------+---------+ 26220
      tggggtagagatgattttatgttttttatttaatctacccgtaccaccgcacgcggacat

      gtcccagctacttgggaggctgaggcaggagaattgcttgagcccgggaggcggaggttg
26221 ---------+---------+---------+---------+---------+---------+ 26280
      cagggtcgatgaaccctccgactccgtcctcttaacgaactcgggccctccgcctccaac

      caatgagacgagattgagatggcgccactgcactccagcctggcaacagagtgagactct
26281 ---------+---------+---------+---------+---------+---------+ 26340
      gttactctgctctaactctaccgcggtgacgtgaggtcggaccgttgtctcactctgaga

      gtctcaaaataaataaataaataaataaataaataaataaataaataaattttagaa
26341 ---------+---------+---------+---------+---------+---------+ 26400
      cagagttttatttatttatttatttatttatttatttatttatttattaaaatctt

      caaattactgaaagaccacaaaaaaaaaaactgtagcacaacggaagtctctaaattcct
26401 ---------+---------+---------+---------+---------+---------+ 26460
      gtttaatgactttctggtgttttttttttgacatcgtgttgccttcagagatttaagga
```

Figure 1 – page 36

```
      tagcttaaaaggttttaacagtgcttatgttttgtatagctaattgctgtaagtctgtaa
26461 ---------+---------+---------+---------+---------+---------+ 26520
      atcgaattttccaaaattgtcacgaatacaaaacatatcgattaacgacattcagacatt

      ctaaaaccaagattacagtagcacaatgcatagaagttaaagataagtcaatttttttaac
26521 ---------+---------+---------+---------+---------+---------+ 26580
      gattttggttctaatgtcatcgtgttacgtatcttcaatttctattcagttaaaaaattg

      ctcacctttggctttttgtttgttggcttttatattaagaaattttaagggtttattaat
26581 ---------+---------+---------+---------+---------+---------+ 26640
      gagtggaaaccgaaaaacaaacaaccgaaaatataattctttaaaattcccaaataatta

      gcctatccacatccattcccatctggcctagaactttctttttttggtgggggaggggg
26641 ---------+---------+---------+---------+---------+---------+ 26700
      cggataggtgtaggtaagggtagaccggatcttgaaagaaaaaaaccacccccctccccc

      acggagtcttcctctgtcacccaggctggggtgcagtggcgtgatctcatctcactgcaa
26701 ---------+---------+---------+---------+---------+---------+ 26760
      tgcctcagaaggagacagtgggtccgaccccacgtcaccgcactagagtagagtgacgtt

      cctccgcctcacaggttcaagtgattctcctgcctcagcctcctgagtagctgtaattac
26761 ---------+---------+---------+---------+---------+---------+ 26820
      ggaggcggagtgtccaagttcactaagaggacggagtcggaggactcatcgacattaatg

      aggcatgtgccaccatgcctggctaatttttttttcttttttttttttttttccgagatg
26821 ---------+---------+---------+---------+---------+---------+ 26880
      tccgtacacggtggtacggaccgattaaaaaaaaagaaaaaaaaaaaaaaaaggctctac

      gagtcttgctctgttgcccaggctggagtgcagtggtgcgacctcggctcactgcaacct
26881 ---------+---------+---------+---------+---------+---------+ 26940
      ctcagaacgagacaacgggtccgacctcacgtcaccacgctggagccgagtgacgttgga

      ctgcctcccaagttcaagcgattcttctgcctcagcctccagagtagatgggactacagg
26941 ---------+---------+---------+---------+---------+---------+ 27000
      gacggagggttcaagttcgctaagaagacggagtcggaggtctcatctaccctgatgtcc

      tgcgtgccaccatgcctggctaatttttatttatttttttagtagagatggggtttcat
27001 ---------+---------+---------+---------+---------+---------+ 27060
      acgcacggtggtacggaccgattaaaaataaaataaaaaaatcatctctaccccaaagta

      catattggccaggctggtctcgaactccttacctcatgatccacccaccttggcctccca
27061 ---------+---------+---------+---------+---------+---------+ 27120
      gtataaccggtccgaccagagcttgaggaatggagtactaggtgggtggaaccggagggt

      aagtgctgggattataggcatgagccactgtgcccagccctaattcgtattttttagtaga
27121 ---------+---------+---------+---------+---------+---------+ 27180
      ttcacgaccctaatatccgtactcggtgacacgggtcgggattaagcataaaaatcatct

      gacagggtttcaccatgttggtcaggctggtctcaaactgctgatcttaggtgaccaacc
27181 ---------+---------+---------+---------+---------+---------+ 27240
      ctgtcccaaagtggtacaaccagtccgaccagagtttgacgactagaatccactggttgg
```

Figure 1 – page 37

```
      tgtctcggcctcccaaagtgctgagattacaggggtgaaccaccatgcctggtctggcct
27241 ---------+---------+---------+---------+---------+---------+ 27300
      acagagccggagggtttcacgactctaatgtccccacttggtggtacggaccagaccgga

      agaactttcaaattcgctatgtgtcttttggctctaagccccttgaccataggggtccca
27301 ---------+---------+---------+---------+---------+---------+ 27360
      tcttgaaagtttaagcgatacacagaaaaccgagattcggggaactggtatccccagggt

      ccaaggcacaagatggacccagggaaggcagctgtgccaccccagcaacacagtgagata
27361 ---------+---------+---------+---------+---------+---------+ 27420
      ggttccgtgttctacctgggtcccttccgtcgacacggtggggtcgttgtgtcactctat

      aaataaaagtttggtgaccattgatgttgcctctgacaaatctaggccagaatgcggaga
27421 ---------+---------+---------+---------+---------+---------+ 27480
      tttattttcaaaccactggtaactacaacggagactgtttagatccggtcttacgcctct

      aagtaaatcaaaaataaaattctaggccgggcgcggtggctcacacctgtaatcccagca
27481 ---------+---------+---------+---------+---------+---------+ 27540
      ttcatttagtttttattttaagatccggcccgcgccaccgagtgtggacattagggtcgt

      ctttgggaggccgaggcgggtggatcacaaggtcaggagttcgagaccagcctggccaac
27541 ---------+---------+---------+---------+---------+---------+ 27600
      gaaaccctccggctccgcccacctagtgttccagtcctcaagctctggtcggaccggttg

      atagtgaaaccccgtctctactaaaaataaaaaatcagccaggcgtgggggcaggcacct
27601 ---------+---------+---------+---------+---------+---------+ 27660
      tatcactttggggcagagatgatttttattttttagtcggtccgcacccccgtccgtgga

      gtagtcccagctacttgggaggctgaggcaggagaattccttgaacctgggaggtggagg
27661 ---------+---------+---------+---------+---------+---------+ 27720
      catcagggtcgatgaaccctccgactccgtcctcttaaggaacttggaccctccacctcc

      ttgcagtgagccgagatcatgccactgcactctaacctgggcgacagagcgagactccat
27721 ---------+---------+---------+---------+---------+---------+ 27780
      aacgtcactcggctctagtacggtgacgtgagattggacccgctgtctcgctctgaggta

      ctcaaaaaataaaaaaaaataaaaaaataaaaaaataaaataaaattataaaccctcaac
27781 ---------+---------+---------+---------+---------+---------+ 27840
      gagtttttattttttttttatttttttatttttttattttattttaatatttgggagttg

      catctgaacggacccctcctgtcgggcaaaggcattgcaaagttatcctaaaaaactagt
27841 ---------+---------+---------+---------+---------+---------+ 27900
      gtagacttgcctggggaggacagcccgtttccgtaacgtttcaataggatttttttgatca

      tcaggtcacgaagggaaggagaagtttggacatgcctcattattccctcctcccttttgg
27901 ---------+---------+---------+---------+---------+---------+ 27960
      agtccagtgcttcccttcctcttcaaacctgtacggagtaataagggaggagggaaaacc

      aattcagacactgctgaccagcattaccattaaaacagatcttaagactgatagaacaga
27961 ---------+---------+---------+---------+---------+---------+ 28020
      ttaagtctgtgacgactggtcgtaatggtaattttgtctagaattctgactatcttgtct
```

Figure 1 – page 38

```
      ctctttaaatctggtaagaaacatttacaatctattctctctgtagcctgctgcctagag
28021 ---------+---------+---------+---------+---------+---------+ 28080
      gagaaatttagaccattctttgtaaatgttagataagagagacatcggacgacggatctc

      gcttcatctgcatgataaaaccttggtctccacaatctcttatcataacctagacactcc
28081 ---------+---------+---------+---------+---------+---------+ 28140
      cgaagtagacgtactattttggaaccagaggtgttagagaatagtattggatctgtgagg

      cttctattgatcccaggtctttggattataactcaaccaattgccaatcacaaaatcttt
28141 ---------+---------+---------+---------+---------+---------+ 28200
      gaagataactagggtccagaaacctaatattgagttggttaacggttagtgttttagaaa

      gaatctgcctgtgacctggaaatccccacttccagttgtcccacgtttctggtctgaacc
28201 ---------+---------+---------+---------+---------+---------+ 28260
      cttagacggacactggacctttaggggtgaaggtcaacagggtgcaaagaccagacttgg

      aatgtacatattatatgtattgattgatgtcttatgtctctctaaaatgtataaaaccaa
28261 ---------+---------+---------+---------+---------+---------+ 28320
      ttacatgtataatatacataactaactacagaatacagagagattttacatattttggtt

      gttatagggtgaccactttgggcacatgtttgcagatctcctgagggctgtgtcacaggc
28321 ---------+---------+---------+---------+---------+---------+ 28380
      caatatcccactggtgaaacccgtgtacaaacgtctagaggactcccgacacagtgtccg

      cattggtcacttatttggctcagaataaatctttttaagtattttagagtttgacccttt
28381 ---------+---------+---------+---------+---------+---------+ 28440
      gtaaccagtgaataaaccgagtcttatttagaaaaattcataaaatctcaaactgggaaa

      ttgttgacaatgtttaacatcctacagttatgacaccctaatttgaatttatacagctta
28441 ---------+---------+---------+---------+---------+---------+ 28500
      aacaactgttacaaattgtaggatgtcaatactgtgggattaaacttaaatatgtcgaat

      acttcaataacatactaaaattctgctcctttaaagcttgttctcaactattttagttct
28501 ---------+---------+---------+---------+---------+---------+ 28560
      tgaagttattgtatgattttaagacgaggaaatttcgaacaagagttgataaaatcaaga

      tttttttttttttccattgacagagtttcactctatcacccaggctggagtgcagtggca
28561 ---------+---------+---------+---------+---------+---------+ 28620
      aaaaaaaaaaaaaggtaactgtctcaaagtgagatagtgggtccgacctcacgtcaccgt

      cgatcttggctcactgcagcctctgcctcctgggttcaagtgattctcctgccccagcct
28621 ---------+---------+---------+---------+---------+---------+ 28680
      gctagaaccgagtgacgtcggagacggaggacccaagttcactaagaggacggggtcgga

      cacaagtagctgggattacaggtgcgccagccaccatgcctggctaatttttttgtatttt
28681 ---------+---------+---------+---------+---------+---------+ 28740
      gtgttcatcgaccctaatgtccacgcggtcggtggtacggaccgattaaaaaacataaaa

      tagtagaggcggggtctcatcatgttggccagcctggtctcgaactcctgacatcagatg
28741 ---------+---------+---------+---------+---------+---------+ 28800
      atcatctccgccccagagtagtacaaccggtcggaccagagcttgaggactgtagtctac
```

Figure 1 – page 39

```
      atccaccagcctcggcctcccaaagtgctgggattacaggtgtgaactaccacgcccggg
28801 ---------+---------+---------+---------+---------+---------+ 28860
      taggtggtcggagccggagggtttcacgaccctaatgtccacacttgatggtgcgggccc

      tctttctagttcttgatatcacaaaattatgtctttattcattttgtgcccccaaaacgt
28861 ---------+---------+---------+---------+---------+---------+ 28920
      agaaagatcaagaactatagtgttttaatacagaaataagtaaaacacgggggttttgca

      aaactaataattatttaaatgcattggtctcttaaatcatgtggaaaacaaaaagtaga
28921 ---------+---------+---------+---------+---------+---------+ 28980
      tttgattattaataaaatttacgtaaccagagaatttagtacacctttttgtttttcatct

      gttacaaaccattgttacaataatactagctttgccgggtgtggtggcttacgccaccag
28981 ---------+---------+---------+---------+---------+---------+ 29040
      caatgtttggtaacaatgttattatgatcgaaacggcccacaccaccgaatgcggtggtc

      gtgatccacccacctaggttgcccagcctgggcaacaagagcacaactccatctcaaaaa
29041 ---------+---------+---------+---------+---------+---------+ 29100
      cactaggtgggtggatccaacgggtcggacccgttgttctcgtgttgaggtagagttttt

      aacaaaaacaaataaacaaaaaaccccaataataccagcttttttttttttttgagacag
29101 ---------+---------+---------+---------+---------+---------+ 29160
      ttgtttttgtttatttgtttttttggggttattatggtcgaaaaaaaaaaaaaactctgtc

      agcttcgctcttgttgcccaggctagagtgcaatggtgcggtcttggctcaccgcaacct
29161 ---------+---------+---------+---------+---------+---------+ 29220
      tcgaagcgagaacaacgggtccgatctcacgttaccacgccagaaccgagtggcgttgga

      ccgcctcctgggttcaagcggttctcctgcctcagcttcccaagtagctgggattacagg
29221 ---------+---------+---------+---------+---------+---------+ 29280
      ggcggaggacccaagttcgccaagaggacggagtcgaagggttcatcgaccctaatgtcc

      tgcgcaccatcacagccggctaatttttgtatttttagtagagacggggttttaccatgt
29281 ---------+---------+---------+---------+---------+---------+ 29340
      acgcgtggtagtgtcggccgattaaaaacataaaaatcatctctgccccaaaatggtaca

      tggtcaagctggtctcaaactcctgacctcaggtaatccacctgccttggcctcccaaag
29341 ---------+---------+---------+---------+---------+---------+ 29400
      accagttcgaccagagtttgaggactggagtccattaggtggacggaaccggagggtttc

      tgctgggattacaggcatgagccaccgtgcccggccaatcccagcactttgggaggctga
29401 ---------+---------+---------+---------+---------+---------+ 29460
      acgaccctaatgtccgtactcggtggcacgggccggttagggtcgtgaaaccctccgact

      ggctggcagaccacttgaggtcaggaggtcaagaccagcctggccaacatgctgaaaccg
29461 ---------+---------+---------+---------+---------+---------+ 29520
      ccgaccgtctggtgaactccagtcctccagttctggtcggaccggttgtacgactttggc

      tgtctgtactaaaaatacaaaaattagctgggcacggtggcaaatgcctataatcccagt
29521 ---------+---------+---------+---------+---------+---------+ 29580
      acagacatgatttttatgtttttaatcgacccgtgccaccgtttacggatattagggtca
```

Figure 1 – page 40

```
      tacttgggggggctgaggcaggaggatcgttttgagcccgggatgtggaggctgtagtgag
29581 ---------+---------+---------+---------+---------+---------+ 29640
      atgaacccccccgactccgtcctcctagcaaaactcgggccctacacctccgacatcactc

      ccgtgatcacaacactgtaccccagcctgggcgacagagcaagaccctgcctcaaaaaaa
29641 ---------+---------+---------+---------+---------+---------+ 29700
      ggcactagtgttgtgacatggggtcggacccgctgtctcgttctgggacggagttttttt

      aaaaaaaaaaagcacaaagcttttgagaaatcactttcaaaaatggtacatttgtagtt
29701 ---------+---------+---------+---------+---------+---------+ 29760
      ttttttttttcgtgtttcgaaaactctttagtgaaagtttttaccatgtaaacatcaa

      ggggaaggttaatcgaacctaaaatataagaatcctggaccccaaaacctggagccagta
29761 ---------+---------+---------+---------+---------+---------+ 29820
      ccccttccaattagcttggattttatattcttaggacctggggttttggacctcggtcat

      ttaccagcatgaatctaacccaagctcagtatacaagccacctgtagagctaaagagtga
29821 ---------+---------+---------+---------+---------+---------+ 29880
      aatggtcgtacttagattgggttcgagtcatatgttcggtggacatctcgatttctcact

      tttactaggccgggcacggtggcttacgcctgtaatcccagcactttgggagccgaggcg
29881 ---------+---------+---------+---------+---------+---------+ 29940
      aaatgatccggcccgtgccaccgaatgcggacattagggtcgtgaaaccctcggctccgc

      ggtggatcacgaggtcaggagttcaagaccagcctggccaagatggtgaaaccccgtctc
29941 ---------+---------+---------+---------+---------+---------+ 30000
      ccacctagtgctccagtcctcaagttctggtcggaccggttctaccactttggggcagag

      tactaaaaatacaaaaaaaattagccgggcgtggtggcatgcgcctgtaatcccagctac
30001 ---------+---------+---------+---------+---------+---------+ 30060
      atgatttttatgttttttttaatcggcccgcaccaccgtacgcggacattagggtcgatg

      tccagaggctgaggcagagaattgcttaaacctggaggggcggaggttgcagtgagccga
30061 ---------+---------+---------+---------+---------+---------+ 30120
      aggtctccgactccgtctcttaacgaatttggacctccccgcctccaacgtcactcggct

      gatcgcgccactgcactccagctggggtgacagagtgagactccatctcaaaaaaaaaaa
30121 ---------+---------+---------+---------+---------+---------+ 30180
      ctagcgcggtgacgtgaggtcgaccccactgtctcactctgaggtagagttttttttttt

      aaaagagtgatttactttctttgctttattaaattcttcagcactctgctattctgactc
30181 ---------+---------+---------+---------+---------+---------+ 30240
      ttttctcactaaatgaaagaaacgaaataatttaagaagtcgtgagacgataagactgag

      ttctgttgttcgaagaaggtgatactttggaaagtagacagatttggcttttgagtattc
30241 ---------+---------+---------+---------+---------+---------+ 30300
      aagacaacaagcttcttccactatgaaacctttcatctgtctaaaccgaaaactcataag

      aatccattaaacatttcaaaaatatgtcactgatattttgaaactcctgagagttcattg
30301 ---------+---------+---------+---------+---------+---------+ 30360
      ttaggtaatttgtaaagtttttatacagtgactataaaactttgaggactctcaagtaac
```

Figure 1 – page 41

```
      ataaggaaagctgctggtgagaatcaatatttattttaaaaggcttttatcattctaatt
30361 ---------+---------+---------+---------+---------+---------+ 30420
      tattcctttcgacgaccactcttagttataaataaaattttccgaaaatagtaagattaa

      cttctaaaacctggtttcctaaatactgattataaaagctatcagaaggcgtggtggctc
30421 ---------+---------+---------+---------+---------+---------+ 30480
      gaagattttggaccaaaggatttatgactaatattttcgatagtcttccgcaccaccgag

      acgcctgtaatcccagcactttggggaggccgaggcgggtggatcacgaggtcaggagat
30481 ---------+---------+---------+---------+---------+---------+ 30540
      tgcggacattagggtcgtgaaacccctccggctccgcccacctagtgctccagtcctcta

      cgagaccatcctggctaacacggtgaaaccccgtctctactaaaaatacaaaaaattagc
30541 ---------+---------+---------+---------+---------+---------+ 30600
      gctctggtaggaccgattgtgccactttggggcagagatgatttttatgtttttaatcg

      cgggcgtggtggcgggtgcctgtagtcccagctactcgggaggctgaggcaggagaatgg
30601 ---------+---------+---------+---------+---------+---------+ 30660
      gcccgcaccaccgcccacggacatcagggtcgatgagccctccgactccgtcctcttacc

      cgtgaacccgggaggcggagcttgcagtgagcagagatcatgccactgcactccagcctg
30661 ---------+---------+---------+---------+---------+---------+ 30720
      gcacttgggccctccgcctcgaacgtcactcgtctctagtacggtgacgtgaggtcggac

      ggcgacagagtgaggctccgtctcaagaaaaaaaaaaaatgctatcagaagataatggtt
30721 ---------+---------+---------+---------+---------+---------+ 30780
      ccgctgtctcactccgaggcagagttctttttttttttacgatagtcttctattaccaa

      acaagtaaagagggtctttcctcgagctacagtattttcagtgtactctggcttttttt
30781 ---------+---------+---------+---------+---------+---------+ 30840
      tgttcatttctcccagaaaggagctcgatgtcataaaagtcacatgagaccgaaaaaaa

      tttcctttgagacagagtctcgctctgtcacccaggctggagtgcagtggcacgatcttg
30841 ---------+---------+---------+---------+---------+---------+ 30900
      aaaggaaactctgtctcagagcgagacagtgggtccgacctcacgtcaccgtgctagaac

      gcttactcctccgcctcctgggttcaaacaattctcctgcctcagcttcccgagtagctg
30901 ---------+---------+---------+---------+---------+---------+ 30960
      cgaatgaggaggcggaggacccaagtttgttaagaggacggagtcgaagggctcatcgac

      ggactacaggcacacgccaccacgcccggctcatttttgtatttaatagagacggggt
30961 ---------+---------+---------+---------+---------+---------+ 31020
      cctgatgtccgtgtgcggtggtgcgggccgagtaaaaacataaaattatctctgcccca

      ttcaccgggttgcccaggctggtggtgaactcctgagctcaggcaatccgcccgcctcgg
31021 ---------+---------+---------+---------+---------+---------+ 31080
      aagtggcccaacgggtccgaccaccacttgaggactcgagtccgttaggcgggcggagcc

      cctcccaaagtgctgggatgacaggtgtgagccactgtgcccagccactctggctatttt
31081 ---------+---------+---------+---------+---------+---------+ 31140
      ggagggtttcacgaccctactgtccacactcggtgacacgggtcggtgagaccgataaaa
```

Figure 1 – page 42

```
      ttttaaaaaaggagttaaatgagtttgcttctgcagatgaccattttctttctgcgtagc
31141 ---------+---------+---------+---------+---------+---------+ 31200
      aaaatttttcctcaatttactcaaacgaagacgtctactggtaaaagaaagacgcatcg

      tgtccttgttctccctcccagtgtgcgtgcaacacatgtacaggaggttcttgaccttag
31201 ---------+---------+---------+---------+---------+---------+ 31260
      acaggaacaagagggagggtcacacgcacgttgtgtacatgtcctccaagaactggaatc

      atataaattgtaaaattccacatatttgaactggtttatcccaacataaggtctcctttc
31261 ---------+---------+---------+---------+---------+---------+ 31320
      tatatttaacattttaaggtgtataaacttgaccaaatagggttgtattccagaggaaag

      tgctttatttcagcctgcagatgtgccaatgtctttaggtcagtttcaagtttttgaaat
31321 ---------+---------+---------+---------+---------+---------+ 31380
      acgaaataaagtcggacgtctacacggttacagaaatccagtcaaagttcaaaaacttta

      gggaataagtgacactgaaggaagattttaataaatgaaacagttgtgtgacctaggaat
31381 ---------+---------+---------+---------+---------+---------+ 31440
      cccttattcactgtgacttccttctaaaattatttactttgtcaacacactggatcctta

      ataaccttgtgctcttagggaaggacattcttatctttttttttttttcttaacggaag
31441 ---------+---------+---------+---------+---------+---------+ 31500
      tattggaacacgagaatcccttcctgtaagaatagaaaaaaaaaaaaaagaattgccttc

      acctttatgataaacgctggagtacagacagtacacgcagctggcatgcagggtattgca
31501 ---------+---------+---------+---------+---------+---------+ 31560
      tggaaatactatttgcgacctcatgtctgtcatgtgcgtcgaccgtacgtcccataacgt

      tatacttaacatcttgagagtccttctgctttttcttcatcttctttttaatcctgatat
31561 ---------+---------+---------+---------+---------+---------+ 31620
      atatgaattgtagaactctcaggaagacgaaaaagaagtagaagaaaaattaggactata

      gcaaaatgtattttgccattaaaacaattgtactattaaaacactgcagcatctggctgg
31621 ---------+---------+---------+---------+---------+---------+ 31680
      cgttttacataaaacggtaattttgttaacatgataattttgtgacgtcgtagaccgacc

      gcgtggtggctcacacctgtaatcccagcattttgggaggctgaggcgggtggatcactt
31681 ---------+---------+---------+---------+---------+---------+ 31740
      cgcaccaccgagtgtggacattagggtcgtaaaaccctccgactccgcccacctagtgaa

      gaggtcaggagttcaacagcagcctgtctaacatggtgaaacccctctctactaaaaat
31741 ---------+---------+---------+---------+---------+---------+ 31800
      ctccagtcctcaagttgtcgtcggacagattgtaccactttggggagagatgattttta

      acaaaaattagctgggtgtggtggcgggtgcctgtaatcccagcttttggaagactgag
31801 ---------+---------+---------+---------+---------+---------+ 31860
      tgtttttaatcgacccacaccaccgcccacggacattagggtcgaaaaccttctgactc

      gcaggaggatcacctgggaggcagaggttgcagtgagccaagatcgtgccactgcactcc
31861 ---------+---------+---------+---------+---------+---------+ 31920
      cgtcctcctagtggaccctccgtctccaacgtcactcggttctagcacggtgacgtgagg
```

Figure 1 – page 43

```
      agcctcggcgacaaagggagactccctctcaaaaacaaaaaaacaacaaaacactgcagc
31921 ---------+---------+---------+---------+---------+---------+ 31980
      tcggagccgctgtttccctctgagggagagtttttgtttttttgttgttttgtgacgtcg

      atctgaaatgatgcaaacaggattagggctatggactgtcttaatagtaatggtagtaat
31981 ---------+---------+---------+---------+---------+---------+ 32040
      tagactttactacgtttgtcctaatcccgatacctgacagaattatcattaccatcatta

      agcattaacaaccatagcagtaatatagaggaattaacttttattgaatagttaatatgt
32041 ---------+---------+---------+---------+---------+---------+ 32100
      tcgtaattgttggtatcgtcattatatctccttaattgaaaataacttatcaattataca

      ttaaggcaccctgtcatttagtcctcacaatcacccctattatcttcatttgacagatgg
32101 ---------+---------+---------+---------+---------+---------+ 32160
      aattccgtgggacagtaaatcaggagtgttagtggggataatagaagtaaactgtctacc

      agagactgaggctctgaaagattcatttacaaatccaaagtcatacagctagaaagtggt
32161 ---------+---------+---------+---------+---------+---------+ 32220
      tctctgactccgagactttctaagtaaatgtttaggtttcagtatgtcgatctttcacca

      gaatttgcacccacatctgattctggagctggcactctaaaccagtgtgctgctccatct
32221 ---------+---------+---------+---------+---------+---------+ 32280
      cttaaacgtgggtgtagactaagacctcgaccgtgagatttggtcacacgacgaggtaga

      ctccatagttgtacttctcatagaatcacaggatgttggtgcaggaaaggactgcttata
32281 ---------+---------+---------+---------+---------+---------+ 32340
      gaggtatcaacatgaagagtatcttagtgtcctacaaccacgtcctttcctgacgaatat

      tctgggtaccccacctttcatttccttcaagtcttgagatctttttgaactagaagcatg
32341 ---------+---------+---------+---------+---------+---------+ 32400
      agacccatggggtggaaagtaaaggaagttcagaactctagaaaaacttgatcttcgtac

      catttagaagtgatattgatatcaccatctcctgttggtagatagatcattgagtggaaa
32401 ---------+---------+---------+---------+---------+---------+ 32460
      gtaaatcttcactataactatagtggtagaggacaaccatctatctagtaactcaccttt

      gaagagggttcaagggattctcccacctcagcctcatagtagccaccacgcccaactaat
32461 ---------+---------+---------+---------+---------+---------+ 32520
      cttctcccaagttccctaagagggtggagtcggagtatcatcggtggtgcgggttgatta

      ttttatattttcagtagagacggggtttcatcatgttggccaggctggtctcgaactcct
32521 ---------+---------+---------+---------+---------+---------+ 32580
      aaaatataaaagtcatctctgccccaaagtagtacaaccggtccgaccagagcttgagga

      gacctcaggtgatccactgccttggcctcccagagtgctgggattactcccagagtacat
32581 ---------+---------+---------+---------+---------+---------+ 32640
      ctggagtccactaggtgacggaaccggagggtctcacgaccctaatgagggtctcatgta

      gagccaccgcaccaggccagggcaaaccctttcaagcaggagttccagtatactgagaga
32641 ---------+---------+---------+---------+---------+---------+ 32700
      ctcggtggcgtggtccggtcccgtttgggaaagttcgtcctcaaggtcatatgactctct
```

Figure 1 – page 44

```
       tggaaatgcaattgatgtgaagtcctagcagtagcaaccagcagagctggccttcttcca
32701  ---------+---------+---------+---------+---------+---------+ 32760
       acctttacgttaactacacttcaggatcgtcatcgttggtcgtctcgaccggaagaaggt

       ggcttggagatcctctgccagatgctcatcttaccagatgcaggcagacctcttcatttc
32761  ---------+---------+---------+---------+---------+---------+ 32820
       ccgaacctctaggagacggtctacgagtagaatggtctacgtccgtctggagaagtaaag

       agaaaggtagacactgagggacagagagaccaaggccagcaggaagtcagtcactttagt
32821  ---------+---------+---------+---------+---------+---------+ 32880
       tctttccatctgtgactccctgtctctctggttccggtcgtccttcagtcagtgaaatca

       aaagggtccaccagtctatcagtttcatgaatgtagagtctgtgcctgccttgtacaccc
32881  ---------+---------+---------+---------+---------+---------+ 32940
       tttcccaggtggtcagatagtcaaagtacttacatctcagacacggacggaacatgtggg

       ctctatttgcagtgaccagaataagtagtaggactgtaaatttatgttataatgaattca
32941  ---------+---------+---------+---------+---------+---------+ 33000
       gagataaacgtcactggtcttattcatcatcctgacatttaaatacaatattacttaagt

       ttaccattatttaaagtggcatgttcatgctttttttttttttttgagatggagtctcg
33001  ---------+---------+---------+---------+---------+---------+ 33060
       aatggtaataaatttcaccgtacaagtacgaaaaaaaaaaaaaaaactctacctcagagc

       ctctgtcacccaggttggagtgcagtggtgtgatctcagctcactgcaacctccacctcc
33061  ---------+---------+---------+---------+---------+---------+ 33120
       gagacagtgggtccaacctcacgtcaccacactagagtcgagtgacgttggaggtggagg

       taggttcaagtgattctcttgcctcagcctcccgagtagctgagactacagacgtgccac
33121  ---------+---------+---------+---------+---------+---------+ 33180
       atccaagttcactaagagaacggagtcggagggctcatcgactctgatgtctgcacggtg

       cacacccagctaatttttgtatttttagtagagatgggattttgccatattgcccaggc
33181  ---------+---------+---------+---------+---------+---------+ 33240
       gtgtgggtcgattaaaaacataaaaatcatctctaccctaaaacggtataacgggtccg

       ttgtctcaaactcctggcctcaggtgatccattggcctcggcctctcaaagtgctgggat
33241  ---------+---------+---------+---------+---------+---------+ 33300
       aacagagtttgaggaccggagtccactaggtaaccggagccggagagtttcacgaccctaa

       tacaggcgtgagccaccgtgcccagaccctgtgctcttgatttcctatctttgtacttgg
33301  ---------+---------+---------+---------+---------+---------+ 33360
       atgtccgcactcggtggcacgggtctgggacacgagaactaaaggatagaaacatgaacc

       cttttctctggccccactggtactattgttagaggtatctcatttggaggtgaaaggagg
33361  ---------+---------+---------+---------+---------+---------+ 33420
       gaaaagagaccggggtgaccatgataacaatctccatagagtaaacctccactttcctcc

       ggaaataaatacagcagtcttgtcttttaaataaatacagcagtcttatgttactctact
33421  ---------+---------+---------+---------+---------+---------+ 33480
       cctttatttatgtcgtcagaacagaaaatttatttatgtcgtcagaatacaatgagatga
```

Figure 1 – page 45

```
       ctgagatctgtctggccattgttggcaatttcatctgagcatcagcaattgctagtgaca
 33481 ---------+---------+---------+---------+---------+---------+ 33540
       gactctagacagaccggtaacaaccgttaaagtagactcgtagtcgttaacgatcactgt

       gccctacatctgggactcactttcctgtttggtataaatgtttctggagattagaataag
 33541 ---------+---------+---------+---------+---------+---------+ 33600
       cgggatgtagaccctgagtgaaaggacaaaccatatttacaaagacctctaatcttattc

       ggaagagaagtcgttttagcatttccgtatctcagttccaaagaggtttaaaaggcacgt
 33601 ---------+---------+---------+---------+---------+---------+ 33660
       ccttctcttcagcaaaatcgtaaaggcatagagtcaaggtttctccaaattttccgtgca
                   I10(-282)
       gcaaatgacaacccacaaaacaaaatcaactgagcaaaaatcaatgctctgcccaagag
 33661 ---------+---------+---------+---------+---------+---------+ 33720
       cgtttactgttggggtgttttgttttagttgactcgtttttagttacgagacgggttctc
                                                  I10(-189)
       ggaccatctttaagaagctttaagtgaagtttaccttgaaagttgtaattagaagcttca
 33721 ---------+---------+---------+---------+---------+---------+ 33780
       cctggtagaaattcttcgaaattcacttcaaatggaactttcaacattaatcttcgaagt

       ggaagcaagtgcctttatggcagaatgactgatgttactcccaggatctcatggaattgt
 33781 ---------+---------+---------+---------+---------+---------+ 33840
       ccttcgttcacggaaataccgtcttactgactacaatgagggtcctagagtaccttaaca
                         I10(-94)
       aaaatttatctctgttctgtgtaagtcaacctaaatcaaacagaaatattagtgtttgg
 33841 ---------+---------+---------+---------+---------+---------+ 33900
       ttttaaaatagagacaagacacattcagttggatttagtttgtctttataatcacaaacc
                                                                    Exon 11
       gtacatcaaaacacctttaacttgtcctttcatttggtttgccttttgacaggatataa
 33901 ---------+---------+---------+---------+---------+---------+ 33960
       catgtagttttgtggaaattgaacaggaaagtaaaaccaaacggaaaactgtcctatatt

                                                         D  I  I -

       tcacagatccatttaagcttgcagaagagtctgacagtatgaagtccagatgtgtccctg
 33961 ---------+---------+---------+---------+---------+---------+ 34020
       agtgtctaggtaaattcgaacgtcttctcagactgtcatacttcaggtctacacagggac

         T  D  P  F  K  L  A  E  E  S  D  S  M  K  S  R  C  V  P  D -

       atgctgctggaggctgctgtggcacaaagaaaagctgctaaatctatagccaaccagggg
 34021 ---------+---------+---------+---------+---------+---------+ 34080
       tacgacgacctccgacgacaccgtgtttcttttcgacgatttagatatcggttggtcccc

        A  A  G  G  C  C  G  T  K  K  S  C  *

       accacagtagtgggcaagagtgatctgcatgtttttaacctgcttttccccatagcaca
 34081 ---------+---------+---------+---------+---------+---------+ 34140
       tggtgtcatcacccgttctcactagacgtacaaaaaattggacgaaaaggggtatcgtgt

       gaccataagaaacaacaaatggggccgggcacagtggctcatgcctataatcccagcact
 34141 ---------+---------+---------+---------+---------+---------+ 34200
       ctggtattctttgttgtttaccccggcccgtgtcaccgagtacggatattagggtcgtga
```

Figure 1 – page 46

```
      ttgggaggccgaggcaggcagatcacctgaggtcaggagtttgataccagcctggccaac
34201 ---------+---------+---------+---------+---------+---------+ 34260
      aaccctccggctccgtccgtctagtggactccagtcctcaaactatggtcggaccggttg

      atggtgaaatcctgtctctaccaaaaatacaaaaaaaattagctgggcatggtggtgcac
34261 ---------+---------+---------+---------+---------+---------+ 34320
      taccactttaggacagagatggtttttatgttttttttaatcgacccgtaccaccacgtg

      acctatagtctcagctactcgggaggctgaggcaggagaattgcttgaacccaggaagta
34321 ---------+---------+---------+---------+---------+---------+ 34380
      tggatatcagagtcgatgagccctccgactccgtcctcttaacgaacttgggtccttcat

      gaggctgcagtgagtaagcatcacgccactgtactccagcctgggcaacagagcaagact
34381 ---------+---------+---------+---------+---------+---------+ 34440
      ctccgacgtcactcattcgtagtgcggtgacatgaggtcggacccgttgtctcgttctga

      ctgtctcaaaagcaaaaaaaaaaaaaaaaaaagaaagaaagaaaaagaaaacaacaaatg (SEQ ID NO:1)
34441 ---------+---------+---------+---------+---------+---------+ 34500
      gacagagttttcgttttttttttttttttttctttctttctttttcttttgttgtttac (SEQ ID NO:2)
```

Figure 2A – page 1

```
    GAGACAGTGAGTGCGCGCCCTGAGTCGCAGGCCGAGGAGACAGTGAGTGCGCGCCCTGAG
  1 ---------+---------+---------+---------+---------+---------+ 60
    CTCTGTCACTCACGCGCGGGACTCAGCGTCCGGCTCCTCTGTCACTCACGCGCGGGACTC

    TCGCAGGCCGAGGAGACATGGCTGCACTTCGTGACGCTGAGATACAGAAGGACGTGCAGA
 61 ---------+---------+---------+---------+---------+---------+ 120
    AGCGTCCGGCTCCTCTGTACCGACGTGAAGCACTGCGACTCTATGTCTTCCTGCACGTCT

                      M  A  A  L  R  D  A  E  I  Q  K  D  V  Q  T -

    CCTACTACGGGCAGGTGCTGAAGAGATCGGCAGACCTCCAGACCAACGGCTGTGTCACCA
121 ---------+---------+---------+---------+---------+---------+ 180
    GGATGATGCCCGTCCACGACTTCTCTAGCCGTCTGGAGGTCTGGTTGCCGACACAGTGGT

      Y  Y  G  Q  V  L  K  R  S  A  D  L  Q  T  N  G  C  V  T  T -

    CAGCCAGGCCGGTCCCCAAGCACATCCGGGAAGCCTTGCAAAATGTACACGAAGAAGTAG
181 ---------+---------+---------+---------+---------+---------+ 240
    GTCGGTCCGGCCAGGGGTTCGTGTAGGCCCTTCGGAACGTTTTACATGTGCTTCTTCATC

      A  R  P  V  P  K  H  I  R  E  A  L  Q  N  V  H  E  E  V  A -

    CCCTAAGATATTATGGCTGTGGTCTGGTGATCCCTGAGCATCTAGAAAACTGCTGGATTT
241 ---------+---------+---------+---------+---------+---------+ 300
    GGGATTCTATAATACCGACACCAGACCACTAGGGACTCGTAGATCTTTTGACGACCTAAA

      L  R  Y  Y  G  C  G  L  V  I  P  E  H  L  E  N  C  W  I  L -

    TGGATCTGGGTAGTGGAAGTGGCAGAGATTGCTATGTACTTAGCCAGCTGGTTGGTGAAA
301 ---------+---------+---------+---------+---------+---------+ 360
    ACCTAGACCCATCACCTTCACCGTCTCTAACGATACATGAATCGGTCGACCAACCACTTT

      D  L  G  S  G  S  G  R  D  C  Y  V  L  S  Q  L  V  G  E  K -

    AAGGACACGTGACTGGAATAGACATGACCAAAGGCCAGGTGGAAGTGGCTGAAAAGTATC
361 ---------+---------+---------+---------+---------+---------+ 420
    TTCCTGTGCACTGACCTTATCTGTACTGGTTTCCGGTCCACCTTCACCGACTTTTCATAG

      G  H  V  T  G  I  D  M  T  K  G  Q  V  E  V  A  E  K  Y  L -

    TTGACTATCACATGGAAAAATATGGCTTCCAGGCATCTAATGTGACTTTTTTCCATGGCA
421 ---------+---------+---------+---------+---------+---------+ 480
    AACTGATAGTGTACCTTTTTATACCGAAGGTCCGTAGATTACACTGAAAAAAGGTACCGT

      D  Y  H  M  E  K  Y  G  F  Q  A  S  N  V  T  F  F  H  G  N -

    ACATTGAGAAGTTGGCAGAGGCTGGAATCAAGAATGAGAGCCATGATATTGTTGTATCAA
481 ---------+---------+---------+---------+---------+---------+ 540
    TGTAACTCTTCAACCGTCTCCGACCTTAGTTCTTACTCTCGGTACTATAACAACATAGTT

      I  E  K  L  A  E  A  G  I  K  N  E  S  H  D  I  V  V  S  N -
```

Figure 2A – page 2

```
     ACTGTGTTATTAACCTTGTGCCTGATAAACAACAAGTGCTTCAGGAGGCATATCGGGTGC
 541 ---------+---------+---------+---------+---------+---------+ 600
     TGACACAATAATTGGAACACGGACTATTTGTTGTTCACGAAGTCCTCCGTATAGCCCACG

      C  V  I  N  L  V  P  D  K  Q  Q  V  L  Q  E  A  Y  R  V  L -

     TGAAGCATGGTGGGGAGTTATATTTCAGTGACGTCTATACGAGCCTTGAACTGCCAGAAG
 601 ---------+---------+---------+---------+---------+---------+ 660
     ACTTCGTACCACCCCTCAATATAAAGTCACTGCAGATATGCTCGGAACTTGACGGTCTTC

      K  H  G  G  E  L  Y  F  S  D  V  Y  T  S  L  E  L  P  E  E -

     AAATCAGGACACACAAAGTTTTATGGGGTGAGTGTCTGGGTGGTGCTTTATACTGGAAGG
 661 ---------+---------+---------+---------+---------+---------+ 720
     TTTAGTCCTGTGTGTTTCAAAATACCCCACTCACAGACCCACCACGAAATATGACCTTCC

      I  R  T  H  K  V  L  W  G  E  C  L  G  G  A  L  Y  W  K  E -

     AACTTGCTGTCCTTGCTCAAAAAATTGGGTTCTGCCCTCCACGTTTGGTCACTGCCAATC
 721 ---------+---------+---------+---------+---------+---------+ 780
     TTGAACGACAGGAACGAGTTTTTTAACCCAAGACGGGAGGTGCAAACCAGTGACGGTTAG

      L  A  V  L  A  Q  K  I  G  F  C  P  P  R  L  V  T  A  N  L -

     TCATTACAATTCAAAACAAGGAACTGGAAAGAGTTATCGGTGACTGTCGTTTTGTTTCTG
 781 ---------+---------+---------+---------+---------+---------+ 840
     AGTAATGTTAAGTTTTGTTCCTTGACCTTTCTCAATAGCCACTGACAGCAAAACAAAGAC

      I  T  I  Q  N  K  E  L  E  R  V  I  G  D  C  R  F  V  S  A -

     CAACATTTCGCCTCTTCAAACACTCTAAGACAGGACCAACCAAGAGATGCCAAGTTATTT
 841 ---------+---------+---------+---------+---------+---------+ 900
     GTTGTAAAGCGGAGAAGTTTGTGAGATTCTGTCCTGGTTGGTTCTCTACGGTTCAATAAA

      T  F  R  L  F  K  H  S  K  T  G  P  T  K  R  C  Q  V  I  Y -

     ACAATGGAGGAATTACAGGACATGAAAAAGAACTAATGTTTGATGCCAATTTTACATTTA
 901 ---------+---------+---------+---------+---------+---------+ 960
     TGTTACCTCCTTAATGTCCTGTACTTTTTCTTGATTACAAACTACGGTTAAAATGTAAAT

      N  G  G  I  T  G  H  E  K  E  L  M  F  D  A  N  F  T  F  K -

     AGGAAGGTGAAATTGTTGAAGTGGATGAAGAAACAGCAGCTATCTTGAAGAATTCAAGAT
 961 ---------+---------+---------+---------+---------+---------+ 1020
     TCCTTCCACTTTAACAACTTCACCTACTTCTTTGTCGTCGATAGAACTTCTTAAGTTCTA

      E  G  E  I  V  E  V  D  E  E  T  A  A  I  L  K  N  S  R  F -

     TTGCTCAAGATTTTCTGATCAGACCAATTGGAGAGAAGTTGCCAACATCTGGAGCTGTTC
1021 ---------+---------+---------+---------+---------+---------+ 1080
     AACGAGTTCTAAAAGACTAGTCTGGTTAACCTCTCTTCAACGGTTGTAGACCTCGACAAG

      A  Q  D  F  L  I  R  P  I  G  E  K  L  P  T  S  G  G  C  S -
```

Figure 2A – page 3

```
     TGCTTTGGAGTTAAAGGATATAATCACAGATCCATTTAAGCTTGCAGAAGAGGTCTGACA
1081 ---------+---------+---------+---------+---------+---------+ 1140
     ACGAAACCTCAATTTCCTATATTAGTGTCTAGGTAAATTCGAACGTCTTCTCCAGACTGT

      A  L  E  L  K  D  I  I  T  D  P  F  K  L  A  E  E  S  D  S  -

     GTATGAAGTCCAGATGTGTCCCTGATGCTGCTGGAGGCTGCTGTGGCACAAAGAAAAGCT
1141 ---------+---------+---------+---------+---------+---------+ 1200
     CATACTTCAGGTCTACACAGGGACTACGACGACCTCCGACGACACCGTGTTTCTTTTCGA

      M  K  S  R  C  V  P  D  A  A  G  G  C  C  G  T  K  K  S  C  -

     GCTAAATCTATAGCCAACCAGGGGACCACAGTAGTGGGCAAGAGTGATCTGCATGTTTTTT
1201 ---------+---------+---------+---------+---------+---------+ 1260
     CGATTTAGATATCGGTTGGTCCCCTGGTGTCATCACCCGTTCTCACTAGACGTACAAAAAA

      *

     TAACCTGCTTTTCCCCATAGCACAGACCATAAGAAACAACAAATGAGCCACTGCGCCCGG
1261 ---------+---------+---------+---------+---------+---------+ 1320
     ATTGGACGAAAAGGGGTATCGTGTCTGGTATTCTTTGTTGTTTACTCGGTGACGCGGGCC

     CCATAAATGAATTATTTTTAAGAGGCATTGATTAAAGATTCACAGCAAATCACTAGTTAA
1321 ---------+---------+---------+---------+---------+---------+ 1380
     GGTATTTACTTAATAAAAATTCTCCGTAACTAATTTCTAAGTGTCGTTTAGTGATCAATT

     GCAGATTTTTTTTCTATTTCCTACTTCAAAGTTCTGGTGCCACATAGTGGTCAGAAATGG
1381 ---------+---------+---------+---------+---------+---------+ 1440
     CGTCTAAAAAAAAGATAAAGGATGAAGTTTCAAGACCACGGTGTATCACCAGTCTTTACC

     AACAGAGAAGCTGTCTTAAGCCTTGTTCAAGAAGCAGGAAAGGCATCAGAAGAAGTAACA
1441 ---------+---------+---------+---------+---------+---------+ 1500
     TTGTCTCTTCGACAGAATTCGGAACAAGTTCTTCGTCCTTTCCGTAGTCTTCTTCATTGT

     GTTGGCAGAGGGTCTCAGGAAAAACATCTTCCTTCTGATCTTTTGCATAGCACCTTTTGG
1501 ---------+---------+---------+---------+---------+---------+ 1560
     CAACCGTCTCCCAGAGTCCTTTTTGTAGAAGGAAGACTAGAAAACGTATCGTGGAAAACC

     AATTTTCATCATGTTTGCTTATTAAACAAAGCTCCTACTGCCATCATACTAATCATGCAA
1561 ---------+---------+---------+---------+---------+---------+ 1620
     TTAAAAGTAGTACAAACGAATAATTTGTTTCGAGGATGACGGTAGTATGATTAGTACGTT

     AAAGATTGCCAAATCATGTTTGGTAGGAGGACTTTTGAGGTAGCTTTTGAACAAATGTTT
1621 ---------+---------+---------+---------+---------+---------+ 1680
     TTTCTAACGGTTTAGTACAAACCATCCTCCTGAAAACTCCATCGAAAACTTGTTTACAAA

     TTTTCTTTTTTCTTTTTTTTTGCAATAAAGAAAACAAATTAATCATAAAAAAAAA (SEQ ID NO:3)
1681 ---------+---------+---------+---------+---------+----- 1735
     AAAAGAAAAAAGAAAAAAAAACGTTATTTCTTTTGTTTAATTAGTATTTTTTTTT (SEQ ID NO:4)
```

Figure 2B

MAALRDAEIQKDVQTYYGQVLKRSADLQTNGCVTTARPVPKHIREALQNVHEEVALRY
YGCGLVIPEHLENCWILDLGSGSGRDCYVLSQLVGEKGHVTGIDMTKGQVEVAEKYLD
YHMEKYGFQASNVTFIHGYIEKLGEAGIKNESHDIVVSNCVINLVPDKQQVLQEAYRVL
KHGGELYFSDVYTSLELPEEIRTHKVLWGECLGGALYWKELAVLAQKIGFCPPRLVTAN
LITIQNKELERVIGDCRFVSATFRLFKHSKTGPTKRCQVIYNGGITGHEKELMFDANFTFK
EGEIVEVDEETAAILKNSRFAQDFLIRPIGEKLPTSGGCSALELKDIITDPFKLAEESDSMK
SRCVPDAAGGCCGTKKSC (SEQ ID NO:5)

basic
(-114G), *V4
(-114G), *V3
(-114G), *V2
(-114C), *2V
Construct
0
10
20
30
40
50
60
Activity/Basic
*
*
*

ARSENIC METHYLTRANSFERASE SEQUENCE VARIANTS

CROSS-REFERENCE TO RELATED APPLICATIONS

This application claims priority from U.S. Provisional Application Ser. No. 60/463,114, filed Apr. 15, 2003.

STATEMENT AS TO FEDERALLY SPONSORED RESEARCH

Funding for the work described herein was provided in part by the federal government under grant nos. RO1 GM28157, RO1 GM35720, and UO1 GM61388. The federal government may have certain rights in the invention.

TECHNICAL FIELD

The invention relates to arsenic methyltransferase (ASMT) nucleic acid and amino acid sequence variants.

BACKGROUND

Acute exposure to inorganic arsenic compounds can lead to fever, cardiac arrhythmia, cardiac failure, hepatomegaly, melanosis, peripheral neuropathy, hematopoietic effects, loss of peripheral nervous system function, leukopenia, anemia, or death. Chronic exposure can lead to neurotoxicity, demyelination, liver injury, peripheral vascular disease, and carcinogenesis resulting in hemangiosarcoma of liver, skin cancer, and lung cancer. The majority of occupational exposure to arsenic is in the manufacture of pesticides, herbicides, and other agricultural products, and in the smelting industry. Exposure to arsenic also can result from environmental exposure to contaminated ground water. Metabolism of arsenic is complex as arsenic can be trivalent or pentavalent and can form many different compounds. Methylated and dimethylated arsenic compounds are the major transformation products in vivo and are rapidly excreted in urine. While methylation typically is regarded as a mechanism for detoxification, certain methylated arsenic compounds that contain $As^{III}$ are more cytotoxic and genotoxic than arsenate (the most stable form of arsenic) and arsenite ($AsO_3^{3-}$), and also more potent inhibitors of GSH reductase, thioredoxin reductase, and pyruvate dehydrogenase than arsenite. See, Lin et al., *J. Biol. Chem.* 277(13): 10795-10803 (2002). ASMT (also referred to as AMT) is an enzyme that methylates arsenite using S-adenosyl-L-methionine as the methyl group donor. ASMT is expressed in the liver, kidney, and brain in humans. In rats, ASMT is expressed in heart, adrenal glands, urinary bladder, brain, kidney, lung, and liver.

SUMMARY

The invention is based on the discovery of sequence variants that occur in both coding and non-coding regions of ASMT nucleic acids. Certain ASMT nucleotide sequence variants encode ASMT enzymes that are associated with individual differences in enzymatic activity. Other sequence variants in non-coding regions of the ASMT nucleic acid may alter regulation of transcription and/or splicing of the ASMT nucleic acid. Discovery of these sequence variants allows individual differences in the methylation of drugs and other xenobiotics in humans to be assessed such that particular treatment regimens can be tailored to an individual based on the presence or absence of one or more sequence variants. Identification of ASMT sequence variants also allows predisposition to hemangiosarcoma of liver, skin cancer, and lung cancer to be assessed in individuals.

In one aspect, the invention features an isolated nucleic acid molecule containing an ASMT nucleic acid sequence, wherein the nucleic acid molecule is at least ten nucleotides in length, and wherein the ASMT nucleic acid sequence comprises a nucleotide sequence variant. The nucleotide sequence variant can be at a position selected from the group consisting of position 2278, 2412, 2477, 2534, 2615, 2838, 2840, 3370, 3398, 3435, 5791, 6176, 6324, 6373, 6426, 8011, 8078, 10259, 12025, 12084, 12327, 23855, 23936, 33672, 33765, and 33860 of SEQ ID NO:1.

The nucleotide sequence variant can be a nucleotide substitution or a nucleotide insertion. For example, the nucleotide sequence variant can be a cytosine substitution for thymine at position 2278 of SEQ ID NO:1; an adenine substitution for guanine at position 2412 of SEQ ID NO:1; a guanine substitution for adenine at position 2477 of SEQ ID NO:1; a guanine substitution for cytosine at position 2534 of SEQ ID NO:1; a cytosine substitution for thymine at position 2615 of SEQ ID NO:1; an adenine substitution for cytosine at position 2838 of SEQ ID NO:1; or a cytosine substitution for guanine at position 2840 of SEQ ID NO:1. The nucleotide sequence variant also can be an adenine substitution for thymine at nucleotide 3370 of position 3370 of SEQ ID NO:1; an insertion of a cytosine at position 3398 of SEQ ID NO:1; or a thymine substitution for guanine at position 3435 of SEQ ID NO:1. The nucleotide sequence variant can be an adenine substitution for guanine at position 5791 of SEQ ID NO:1; a guanine substitution for an adenine at position 6178 of SEQ ID NO:1; an adenine substitution for a guanine at position 6324 of SEQ ID NO:1; a cytosine substitution for thymine at position 6373 of SEQ ID NO:1; or a thymine substitution for adenine at position 6426 of SEQ ID NO:1. The nucleotide sequence variant can be a thymine substitution for cytosine at position 8011 of SEQ ID NO:1; a guanine substitution for adenine at position 8078 of SEQ ID NO:1; a cytosine substitution for guanine at position 10259 of SEQ ID NO:1; a cytosine substitution for an adenine at position 12025 of SEQ ID NO:1; or a thymine substitution for a cytosine at position 12084 of SEQ ID NO:1. The nucleotide sequence variant can be a cytosine substitution for thymine at position 12327 of SEQ ID NO:1, a cytosine substitution for thymine at position 23855 of SEQ ID NO:1; or a thymine substitution for cytosine at position 23936 of SEQ ID NO:1. The nucleotide sequence variant also can be a thymine substitution for cytosine at position 33672 of SEQ ID NO:1, an adenine substitution for guanine at position 33765 of SEQ ID NO:1, or an adenine substitution for guanine at position 33860 of SEQ ID NO:1.

Alternatively, the variant can be an insertion or a deletion of a variable number tandem repeat. The deletion or insertion can be between nucleotides 2820 and 3020 of SEQ ID NO:1.

In another aspect, the invention features an isolated nucleic acid encoding an ASMT polypeptide, wherein the polypeptide contains an ASMT amino acid sequence variant relative to the amino acid sequence of SEQ ID NO:5. The amino acid sequence variant can be at a residue selected from the group consisting of 173, 287, and 306 (e.g., a tryptophan at residue 173, a threonine at residue 287, or an isoleucine at residue 306).

In another aspect, the invention features an isolated ASMT polypeptide, wherein the polypeptide contains an ASMT amino acid sequence variant relative to the amino acid sequence of SEQ ID NO:5. The amino acid sequence variant can be at a residue selected from the group consisting of 173, 287, and 306 (e.g., a tryptophan at residue 173, a threonine at residue 287, or an isoleucine at residue 306). Activity of the polypeptide can be altered relative to a wild type ASMT polypeptide.

The invention also features an isolated nucleic acid molecule containing an ASMT nucleic acid sequence, wherein the nucleic acid molecule is at least ten nucleotides in length, wherein the ASMT nucleic acid sequence has at least 99% sequence identity to a region of SEQ ID NO:3. In the ASMT nucleic acid sequence, position 594 is a thymine, position 937 is a cytosine, and position 994 is a thymine. The region can be selected from the group consisting of nucleotides 550 to 650 of SEQ ID NO:3, nucleotides 900 to 950 of SEQ ID NO:3, and nucleotides 951 to 1000 of SEQ ID NO:3.

In yet another aspect, the invention features an article of manufacture including a substrate, wherein the substrate includes a population of isolated ASMT nucleic acid molecules, and wherein the nucleic acid molecules include an ASMT nucleotide sequence variant. The substrate can include a plurality of discrete regions, wherein each region includes a different population of isolated ASMT nucleic acid molecules, and wherein each population of molecules includes a different ASMT nucleotide sequence variant.

The invention also features a method for determining if a mammal is predisposed to increased risk for acute or chronic arsenic exposure. The method includes obtaining a biological sample from a mammal, and detecting the presence or absence of an ASMT nucleotide sequence variant in the sample, wherein risk for toxicity is determined based on the presence or absence of a variant. The method can further include detecting the presence or absence of a plurality of ASMT nucleotide sequence variants in the sample to obtain a variant profile of the mammal, and wherein risk for toxicity is determined based on the variant profile.

In another aspect, the invention features a method for assisting a medical or research professional. The method includes obtaining a biological sample from a mammal, and detecting the presence or absence of a plurality of ASMT nucleotide sequence variants in the sample to obtain a variant profile of the mammal. The method can further include communicating the profile to the medical or research professional.

In yet another aspect, the invention features a method for determining the methyltransferase status of an individual. The method includes determining whether the subject contains a variant ASMT nucleic acid.

The invention also features an isolated nucleic acid molecule including an ASMT nucleic acid sequence, wherein the nucleic acid molecule is at least ten nucleotides in length, and wherein the ASMT nucleic acid sequence includes at least two nucleotide sequence variants. The variants can be within any combination of coding sequences, intron sequences, 5' untranslated sequences, or 3' untranslated sequences.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the nucleotide sequence of the reference ASMT (SEQ ID NO:1) and its complement (SEQ ID NO:2). Exons are labeled and are in bold type. Single nucleotide polymorphisms (SNPs) are circled and labeled. Primer sequences are underlined, and the start and stop codons are double-underlined. The translation initiation codon begins at nucleotide 2954 of SEQ ID NO:1. Exon 1 contains nucleotides 2877 to 2954 of SEQ ID NO:1. Intron 1 contains nucleotides 2955 to 3165 of SEQ ID NO:1. Exon 2 contains nucleotides 3166 to 3206 of SEQ ID NO:1. Intron 2 contains nucleotides 3207 to 3444 of SEQ ID NO:1. Exon 3 contains nucleotides 3445 to 3572 of SEQ ID NO:1. Intron 3 contains nucleotides 3573 to 5808 of SEQ ID NO:1. Exon 4 contains nucleotides 5809 to 5959 of SEQ ID NO:1. Intron 4 contains nucleotides 5960 to 6457 of SEQ ID NO:1. Exon 5 contains nucleotides 6458 to 6594 of SEQ ID NO:1. Intron 5 contains nucleotides 6595 to 7952 of SEQ ID NO:1. Exon 6 contains nucleotides 7953 to 8022 of SEQ ID NO:1. Intron 6 contains nucleotides 8023 to 10314 of SEQ ID NO:1. Exon 7 contains nucleotides 10315 to 10396 of SEQ ID NO:1. Intron 7 contains nucleotides 10397 to 11739 of SEQ ID NO:1. Exon 8 contains nucleotides 11740 to 11871 of SEQ ID NO:1. Intron 8 contains nucleotides 11872 to 12209 of SEQ ID NO:1. Exon 9 contains nucleotides 12210 to 12352 of SEQ ID NO:1. Intron 9 contains nucleotides 12353 to 23904 of SEQ ID NO:1. Exon 10 contains nucleotides 23905 to 24039 of SEQ ID NO:1. Intron 10 contains nucleotides 24040 to 33953 of SEQ ID NO:1. Exon 11 contains nucleotides 33954 to 34161 of SEQ ID NO:1.

FIG. 2A is a cDNA sequence (SEQ ID NO:3) containing the open reading frame of the reference ASMT (nucleotides 78-1202) and the complementary sequence (SEQ ID NO:4) of the cDNA sequence. SNPs are circled, and the start and stop codons are double-underlined.

FIG. 2B is the amino acid sequence (SEQ ID NO:5) of the reference ASMT.

DETAILED DESCRIPTION

Figure 3:
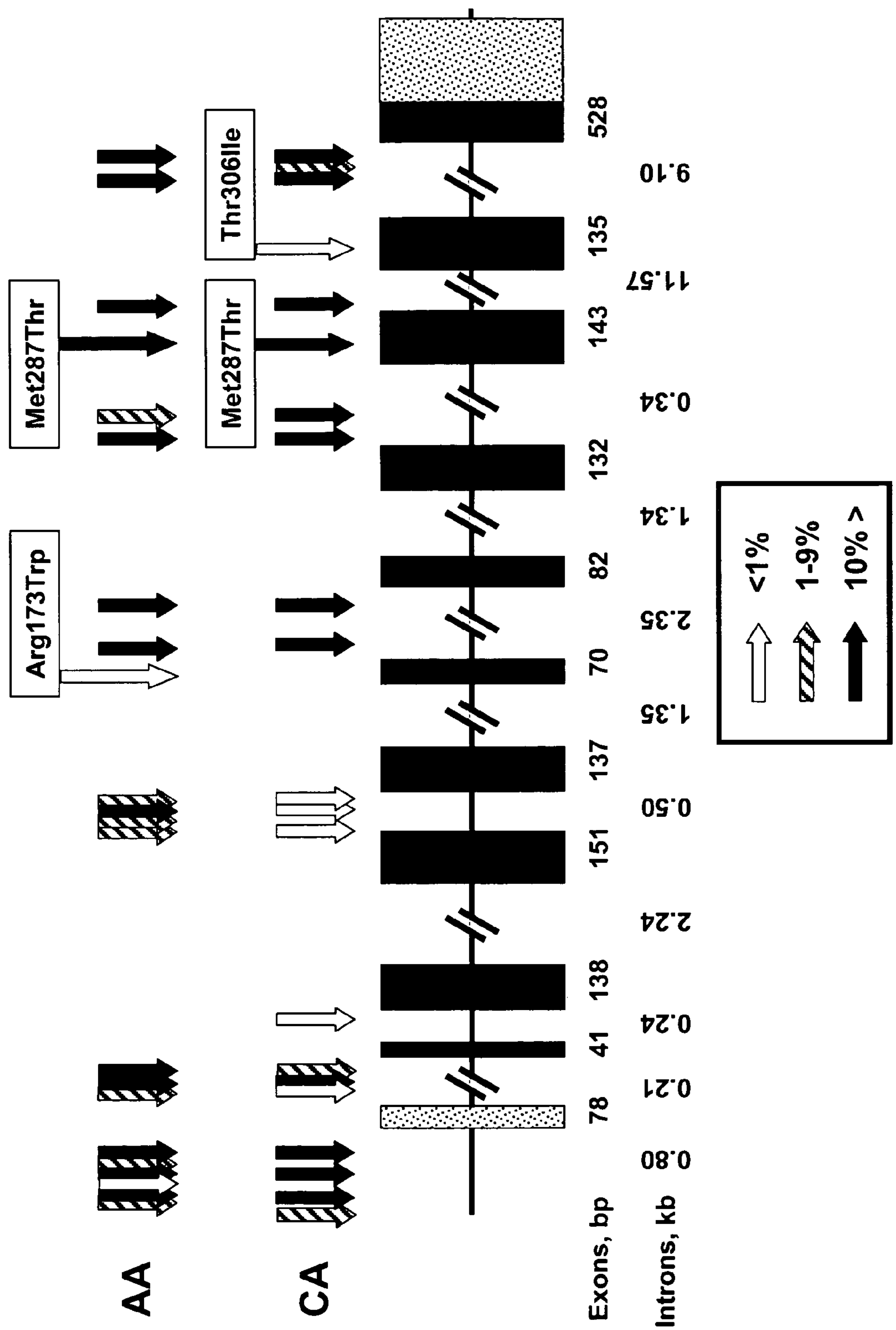
FIG. 3 is a schematic of the locations of polymorphisms within the human ASMT sequence in Caucasian Americans (CA) and African Americans (AA).

The invention features ASMT nucleotide and amino acid sequence variants. ASMT is an enzyme that methylates arsenite and methylarsonous acid using S-adenosylmethionine (SAM) as the methyl donor. Genetically-based variations in ASMT that lead to altered levels of ASMT or altered ASMT activity may be important in determining the risk associated with acute or chronic exposure to arsenic and development of arsenic-induced skin lesions, cancer (e.g., liver, skin, or lung), neurotoxicity, neuropathy, or liver injury.

Nucleic Acid Molecules

The invention features isolated nucleic acids that include an ASMT nucleic acid sequence. The ASMT nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-ASMT proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids of the invention can be in a sense or antisense orientation, can be complementary to the ASMT reference sequence (e.g., SEQ ID NO:2 and SEQ ID NO:4), and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in an ASMT reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference ASMT nucleic acid sequence is provided in FIG. 1 (SEQ ID NO:1) and in GenBank (Accession No. NT_008804). The reference ASMT cDNA including the ASMT ORF is provided in FIG. 2A (SEQ ID NO:3) and the corresponding reference ASMT amino acid sequence is provided in FIG. 2B (SEQ ID NO:5). The nucleic acid and amino acid reference sequences also are referred to herein as "wild type."

As used herein, "untranslated sequence" includes 5' and 3' flanking regions that are outside of the messenger RNA (mRNA) as well as 5' and 3' untranslated regions (5'-UTR or 3'-UTR) that are part of the MRNA, but are not translated. Positions of nucleotide sequence variants in 5' untranslated sequences are designated as "−X" relative to the "A" in the translation initiation codon; positions of nucleotide sequence variants in the coding sequence and 3' untranslated sequence are designated as "+X" or "X" relative to the "A" in the translation initiation codon. Nucleotide sequence variants that occur in introns are designated as "+X" or "X" relative to the "G" in the splice donor site (GT) or as "−X" relative to the "G" in the splice acceptor site (AG).

In some embodiments, an ASMT nucleotide sequence variant encodes an ASMT polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-250 residues, or a full-length ASMT polypeptide). ASMT polypeptides may or may not have ASMT catalytic activity, or may have altered activity relative to the reference ASMT polypeptide. Polypeptides that do not have activity or have altered activity are useful for diagnostic purposes (e.g., for producing antibodies having specific binding affinity for variant ASMT polypeptides).

Corresponding ASMT polypeptides, irrespective of length, that differ in amino acid sequence are herein referred to as allozymes. For example, an ASMT nucleic acid sequence that includes a thymine at nucleotide 517 (nucleotide 8011 of SEQ ID NO:1) encodes an ASMT polypeptide having a tryptophan at amino acid residue 173. This polypeptide (Arg173Trp) would be considered an allozyme with respect to the reference ASMT polypeptide that contains an arginine at amino acid residue 173. Additional non-limiting examples of ASMT sequence variants that alter amino acid sequence include variants at nucleotides 860 and 917 (nucleotides 12327 and 23936, respectively, of SEQ ID NO:1). For example, an ASMT nucleic acid molecule can include a cytosine at nucleotide 860 and encode an ASMT polypeptide having a threonine at amino acid residue 287 in place of a methionine residue (Met287Thr); or a thymine at nucleotide 917 and encode an ASMT polypeptide having an isoleucine at amino acid 306 in place of a threonine residue (Thr306Ile).

ASMT allozymes as described herein are encoded by a series of ASMT alleles. These alleles represent nucleic acid sequences containing sequence variants, typically multiple sequence variants, within coding and non-coding sequences. Representative examples of single nucleotide variants are described above. Table 2 sets out a series of ASMT alleles that encode ASMT. Some alleles are commonly observed, i.e., have allele frequencies >1%, such as the allele having a guanine at nucleotide −477 (nucleotide 2477 of SEQ ID NO:1) in place of an adenine. The relatively large number of alleles and allozymes for ASMT indicates the potential complexity of ASMT pharmacogenetics. Such complexity emphasizes the need for determining single nucleotide variants, (i.e., single nucleotide polymorphisms, SNPs) as well as multiple nucleotide variants and complete ASMT haplotypes (i.e., the set of alleles on one chromosome or a part of a chromosome) of patients. See, e.g., the haplotypes set forth in Table 5.

Certain ASMT nucleotide sequence variants do not alter the amino acid sequence. Such variants, however, could alter regulation of transcription as well as mRNA stability. ASMT variants can occur in intron sequences, for example, within introns 1, 2, 3, 4, 5, 6, 7, 8, 9, or 10. See, for example, the intronic sequence variants set forth in Table 2.

ASMT nucleotide sequence variants that do not change the amino acid sequence also can be within an exon or in 5' or 3' untranslated sequences. Nucleotide sequence variants in the 5' UTR can include a cytosine substitution for thyrnine at nucleotide −676 (nucleotide 2278 of SEQ ID NO:1); an adenine substitution for guanine at nucleotide −542 (nucleotide 2412 of SEQ ID NO:1); a guanine substitution for adenine at nucleotide −477 (nucleotide 2477 of SEQ ID NO:1); a cytosine substitution for thymine at nucleotide −339 (nucleotide 2615 of SEQ ID NO:1); an adenine substitution for cytosine at nucleotide −116 (nucleotide 2838 of SEQ ID NO:1); or a cytosine substitution for guanine at nucleotide −114 (nucleotide 2840 of SEQ ID NO:1).

Other variants in the 5' untranslated sequences can be an insertion or deletion of one or more variable number tandem repeats (VNTR). A VNTR can be any tandemly repeated sequence. Typically, a VNTR can be between about 20 and about 50 (e.g., 20, 22, 24, 26, 28, 30, 31, 32, 33, 34, 35, 36, 37, 38, 39, 40, 42, 44, 46, 48, or 50) nucleotides in length. For example, a VNTR can contain between about 30 and about 40 (e.g., 30, 31, 32, 33, 34, 35, 36, 37, 38, 39, or 40) contiguous nucleotides of the sequence 5'-GAGTCGCAGGCCGAGGAGACAGTGAGTGCGCGCCCTGAGT-3' (SEQ ID NO:6). Alternatively, a VNTR can have a sequence that between about 30 and about 40 nucleotides in length and is at least 90% identical (e.g., 90%, 91%, 92%, 93%, 94%, 95%, 96%, 97%, 98%, or 99% identical) to the sequence set forth in SEQ ID NO:6, wherein the percent identity is determined as described below. A VNTR can be located in the 5' flanking region, exon 1, intron 1, and/or combinations thereof. Thus, the insertion or deletion of a VNTR can be in the 5' untranslated region between, for example, nucleotides 2820 and 3020 of SEQ ID NO:1 (e.g., between nucleotides 2830 and 3010, 2840 and 3000, or 2850 and 2990 of SEQ ID NO:1). In one embodiment, a VNTR can have a nucleotide sequence that is 36 nucleotides in length and contains ASMT sequences from the 5'-FR and exon 1. In another embodiment, a VNTR can have a nucleotide sequence that is 35 nucleotides in length and contains ASMT sequences from exon 1 and intron 1. A genomic ASMT nucleic acid sequence typically can include two, three, or four VNTRs. While a change in the number of VNTRs does not alter the encoded ASMT amino acid sequence, an increase or a decrease in the number of repeats can increase or decrease expression of an ASMT polypeptide.

In some embodiments, nucleic acid molecules of the invention can have at least 97% (e.g., 97.5%, 98%, 98.5%, 99.0%, 99.5%, 99.6%, 99.7%, 99.8%, 99.9%, or 100%) sequence identity with a region of SEQ ID NO:1, SEQ ID NO:2, SEQ ID NO:3, or SEQ ID NO:4 that includes one or more variants described herein. The region of SEQ ID NO:1, 2, 3, or 4 is at least ten nucleotides in length (e.g., 10, 15, 20, 50, 60, 70, 75, 100, 150 or more nucleotides in length). For example, a nucleic acid molecule can have at least 99% identity with nucleotides 550 to 650, 900 to 950, 925 to 975, 951 to 1000,or 950 to 1050 of SEQ ID NO:3, where the nucleotide sequence of SEQ ID NO:3 includes one or more of the variants described herein. For example, the nucleotide sequence of SEQ ID NO:3 can have a thymine at nucleotide 594, a cytosine at nucleotide 937, or a thymine at nucleotide 994, and combinations thereof.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq1.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. The following command will generate an output file containing a comparison between two sequences: C:\Bl2seq −i c:\seq1.txt −j c:\seq2.txt −p blastn −o c:\output.txt −q −1 −r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 969 nucleotides from the target sequence aligned with a region of the sequence set forth in SEQ ID NO: 1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing an ASMT nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis *Genetic Engineering News,* 12(9):1 (1992); Guatelli et al., *Proc. Natl. Acad. Sci. USA,* 87:1874-1878 (1990); and Weiss, *Science,* 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequences depicted in FIG. 1 or 2A can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified are described herein.

ASMT Polypeptides

Isolated ASMT polypeptides of the invention include an amino acid sequence variant relative to the reference ASMT (FIG. 2B, SEQ ID NO:5). The term "isolated" with respect to an ASMT polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

ASMT polypeptides of the invention include variants at one or more of amino acid residues 173, 287, and 306. In particular, a tryptophan residue can be substituted at position 173, a threonine residue at position 287, or an isoleucine residue at position 306. In some embodiments, activity of ASMT polypeptides is altered relative to the reference ASMT. Certain ASMT allozymes can have reduced activity, while other allozymes can have activity that is comparable to the reference ASMT. Other allozymes can have increased activity relative to the reference ASMT. Activity of ASMT polypeptides can be assessed in vitro. For example, the activity of ASMT polypeptides can be assessed by determining the amount of [$^{14}$C]-methylated arsenic products that are produced by a recombinant methyltransferase (e.g., recombinant ASMT) in the presence of sodium arsenite (2.5 mM) and $^{14}$C-SAM (10 μM).

Other biochemical properties of allozymes, such as apparent $K_m$ values, also can be altered relative to the reference ASMT. Apparent $K_m$ values can be calculated, for example, by using the method of Wilkinson with a computer program written by Cleland. Wilkinson, *Biochem. J.,* 80:324-332 (1961); and Cleland, *Nature,* 198:463-365 (1963).

Isolated polypeptides of the invention can be obtained, for example, by extraction from a natural source (e.g., brain tissue), chemical synthesis, or by recombinant production in a host cell. To recombinantly produce ASMT polypeptides, a nucleic acid encoding an ASMT nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to an ASMT nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wisc.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of Escherichia coli can be used to express ASMT variant polypeptides. For example, BL-21 cells can be transformed with a pGEX vector containing an ASMT nucleic acid sequence. The transformed bacteria can be grown exponentially and then stimulated with isopropylthiogalactopyranoside (IPTG) prior to harvesting. In general, the ASMT-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed ASMT polypeptide can be released from the GST moiety.

In eukaryotic host cells, a number of viral-based expression systems can be utilized to express ASMT variant polypeptides. A nucleic acid encoding a polypeptide of the invention can be cloned into, for example, a baculoviral vector such as pBlueBac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Eukaryotic cell lines that stably express ASMT variant polypeptides can be produced using expression vectors with the appropriate control elements and a selectable marker. For example, the eukaryotic expression vector pCR3.1 (Invitrogen, San Diego, Calif.) and p91023(B) (see Wong et al., *Science* (1985) 228:810-815) or modified derivatives thereof are suitable for expression of ASMT variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pcDNA3 (Invitrogen) and then transcribed and translated in vitro using wheat germ extract or rabbit reticulocyte lysate.

ASMT variant polypeptides can be purified by known chromatographic methods including ion exchange and gel filtration chromatography. See, for example, Caine et al., *Protein Expr. Purif.* (1996) 8(2):159-166. ASMT polypeptides can be "engineered" to contain a tag sequence describe herein that allows the polypeptide to be purified (e.g., captured onto an affinity matrix). Immunoaffinity chromatography also can be used to purify ASMT polypeptides.

Non-Human Mammals

The invention features non-human mammals that include ASMT nucleic acids of the invention, as well as progeny and cells of such non-human mammals. Non-human mammals include, for example, rodents such as rats, guinea pigs, and mice, and farm animals such as pigs, sheep, goats, horses, and cattle. Non-human mammals of the invention can express an ASMT variant nucleic acid in addition to an endogenous ASMT (e.g., a transgenic non-human that includes an ASMT nucleic acid randomly integrated into the genome of the non-human mammal). Alternatively, an endogenous ASMT nucleic acid can be replaced with an ASMT variant nucleic acid of the invention by homologous recombination. See, Shastry, *Mol. Cell Biochem.*, (1998) 181(1-2):163-179, for a review of gene targeting technology.

In one embodiment, non-human mammals are produced that lack an endogenous ASMT nucleic acid (i.e., a knockout), and then an ASMT variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous ASMT nucleic acid. That is, cultured ES cells can be transformed with a knockout construct and cells selected in which the ASMT gene is inactivated.

Nucleic acid constructs can be introduced into ES cells, for example, by electroporation or other standard technique.

Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual*, second edition, Cold Spring Harbor Press, Plainview; N.Y., 1989.

To generate a knockout animal, ES cells having at least one inactivated ASMT allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated ASMT allele. If the original ES cell was heterozygous for the inactivated ASMT allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the ASMT gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous ASMT gene and express an ASMT nucleic acid of the invention, and then fused with enucleated oocytes. After activation of the oocytes, the eggs are cultured to the blastocyst stage, and implanted into a recipient. See, Cibelli et al., *Science*, (1998) 280:1256-1258. Adult somatic cells, including, for example, cumulus cells and mammary cells, can be used to produce animals such as mice and sheep, respectively. See, for example, Wakayama et al., *Nature*, (1998) 394(6691):369-374; and Wilmut et al., *Nature*, (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al. 1998, supra.

Non-human mammals of the invention such as mice can be used, for example, to screen toxicity of compounds that are substrates for ASMT, drugs that alter ASMT activity, or for carcinogenesis. For example, ASMT activity or toxicity can be assessed in a first group of such non-human mammals in the presence of a compound, and compared with ASMT activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting ASMT Sequence Variants

ASMT nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33-39), denaturing high performance liquid chromatography (DHPLC, Underhill et al., 1997, *Genome Res.,* 7:996-1005), infrared matrix-assisted laser desorption/ionization (IR-MALDI) mass spectrometry (WO 99/57318), and combinations of such methods.

Genomic DNA generally is used in the analysis of ASMT nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the ASMT gene can be amplified then directly sequenced. Dye primer sequencing can be used to increase the accuracy of detecting heterozygous samples.

Allele specific hybridization also can be used to detect sequence variants, including complete haplotypes of a mammal. See, Stoneking et al., 1991, *Am. J. Hum. Genet.* 48:370-382; and Prince et al., 2001, *Genome Res.,* 11(1): 152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2X SSC (0.3 M NaCl/0.03 M sodium citrate/0.1% sodium dodecyl sulfate (SDS) and washed in 0.1X SSC (0.015 M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For ASMT sequence variants that do not alter a common restriction site, mutagenic primers can be designed that introduce a restriction site when the variant allele is present or when the wild type allele is present. A portion of ASMT nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of ASMT can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected with each set of primers. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, ASMT variants can be detected by antibodies that have specific binding affinity for variant ASMT polypeptides. Variant ASMT polypeptides can be produced in various ways, including recombinantly, as discussed above. Host animals such as rabbits, chickens, mice, guinea pigs, and rats can be immunized by injection of an ASMT variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using an ASMT variant polypeptide and standard hybridoma technology. In particular, monoclonal antibodies can be obtained by any technique that provides for the production of antibody molecules by continuous cell lines in culture such as described by Kohler et al., *Nature,* 256:495 (1975), the human B-cell hybridoma technique (Kosbor et al., *Immunology Today,* 4:72 (1983); Cole et al., *Proc. Natl. Acad. Sci USA,* 80:2026 (1983)), and the EBV-hybridoma technique (Cole et al., *Monoclonal Antibodies and Cancer Therapy,* Alan R. Liss, Inc., pp. 77-96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for an ASMT variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science,* 246: 1275 (1989). Once produced, antibodies or fragments thereof are tested for recognition of ASMT variant polypeptides by standard immunoassay methods including ELISA techniques, radioimmunoassays and Western blotting. See,

*Short Protocols in Molecular Biology*, Chapter 11, Green Publishing Associates and John Wiley & Sons, edited by Ausubel et al., 1992.

Methods

As a result of the present invention, it is possible to determine methyltransferase status of a subject (e.g., a mammal such as a human). “Methyltransferase status” refers to the ability of a subject to transfer a methyl group to a substrate (e.g., arsenite). Methyltransferase status of a subject can be determined by measuring the level of methyltransferase (e.g., ASMT) activity in the subject using, for example, the methods described herein. Alternatively, methyltransferase status can be evaluated by determining whether a methyltransferase nucleic acid sequence (e.g., an ASMT nucleic acid sequence) of a subject contains one or more variants (e.g., one or more variants that are correlated with increased or decreased methyltransferase activity). A variant that results in decreased or increased ASMT activity, for example, can be said to result in “reduced” or “enhanced” methyltransferase status, respectively. In some embodiments, the variant profile of a subject can be used to determine the methyltransferase status of the subject.

“Variant profile” refers to the presence or absence of a plurality (e.g., two or more) of ASMT nucleotide sequence variants or ASMT amino acid sequence variants. For example, a variant profile can include the complete ASMT haplotype of the subject (e.g., see Table 5) or can include the presence or absence of a set of particular non-synonymous SNPs (e.g., single nucleotide substitutions that alter the amino acid sequence of an ASMT polypeptide). In one embodiment, determining the variant profile includes detecting the presence or absence of two or more non-synonymous SNPs (e.g., 2, 3, or 4 non-synonymous SNPs), including those described herein. There may be ethnic-specific pharmacogenetic variation, as certain of the nucleotide and amino acid sequence variants described herein were detected solely in African-American or Caucasian-American subjects. In addition, determining the variant profile can include detecting the presence or absence of any type of ASMT variant (e.g., a SNP or an alteration in the number of VNTRs) together with any other ASMT variant (e.g., a polymorphism pair or a group of polymorphism pairs). Such polymorphism pairs include, without limitation, the pairs described in Table 4. Further, determining the variant profile can include detecting the presence or absence of any ASMT variant together with one or more variants from other methyltransferases.

Methyltransferase activity of an enzyme such as ASMT can be measured using, for example, in vitro methods such as those described herein. As used herein, the term “reduced methyltransferase status” refers to a decrease (e.g., a 5%, 10%, 15%, 20%, 25%, 30%, 40%, 50%, 60%, 70%, 75%, 80%, 90%, 95%, or 100% decrease) in methyltransferase activity (e.g., ASMT activity) of a subject, as compared to a control level of methyltransferase activity. Similarly, the term “enhanced methyltransferase status” refers to an increase (e.g., a 5%, 10%, 15%, 20%, 25%, 30%, 40%, 50%, 60%, 70%, 75%, 80%, 90%, 95%, 100%, or more than 100% increase) in methyltransferase activity of a subject, as compared to a control level of methyltransferase activity. A control level of methyltransferase activity can be, for example, an average level of methyltransferase activity in a population of individuals. In one embodiment, the population includes individuals that do not contain particular ASMT nucleotide sequence variants or particular ASMT amino acid sequence variants (e.g., particular variants that affect methyltransferase status). Alternatively, a control level of methyltransferase activity can refer to the level of methyltransferase activity in a control subject (e.g., a subject that does not contain an ASMT nucleic acid containing a variant).

In further embodiments of the invention, methyltransferase status can be linked to predisposition to (i.e., a relative greater risk of) a particular condition (e.g., acute or chronic toxicity from arsenic exposure). Additional risk factors including, for example, family history and other genetic factors (e.g., polymorphisms in reductases that convert arsenate and methylarsonic acid to arsine and methylarsonous acid) can be considered when determining risk. Predisposition to such conditions can be determined based on the presence or absence of a single ASMT sequence variant or based on a variant profile.

Articles of Manufacture

Articles of manufacture of the invention include populations of isolated ASMT nucleic acid molecules or ASMT polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different ASMT nucleic acid or ASMT polypeptide sequence variant. Such articles of manufacture can include two or more sequence variants of ASMT, or can include all of the sequence variants known for ASMT. For example, the article of manufacture can include two or more of the sequence variants identified herein and one or more other ASMT sequence variants, such as nucleic acid variants that occur in the 5'-flanking region of the ASMT gene. Furthermore, nucleic acid molecules containing sequence variants for other methyltransferases can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., *Nature Genet.,* 14:441-447 (1996); and U.S. Pat. Nos. 5,770,722 and 5,733,729.

The invention will be further described in the following examples, which do not limit the scope of the invention described in the claims.

EXAMPLES

Example 1—Methods and Materials

PCR Amplification and DNA Sequencing: The gene encoding ASMT (also known as CYT19) was cloned based on homology with the rat and mouse sequences and other known methyltransferases. Tissue localization was determined by 3' and 5' RACE.

Anonymized DNA samples from 60 Caucasian-American and 60 African-American subjects were obtained from the Coriell Institute Cell Repository (Camden, N.J.). Eleven PCR reactions were performed with each DNA sample to amplify all ASMT exons and splice junctions. The amplicons were then sequenced using dye-primer sequencing chemistry to facilitate the identification of heterozygous bases (Chadwick et al. *Biotechniques* 20:676-683 (1996)). Universal M13 sequencing tags were added to the 5'-ends of each forward and reverse primer for sequencing purposes. All forward primers contained the M13 forward sequence (5'-TGTAAAACGACGGCCAGT-3'; SEQ ID NO:7), and all reverse primers contained the M13 reverse sequence (5'-CAGGAAACAGCTATGACC-3'; SEQ ID NO:8). The sequences and locations of each primer within the gene are listed in Table 1. "F" represents forward; "R", reverse; "U", upstream; "D", downstream; "I", intron; "FR", flanking region; and "UTR", untranslated region. The locations of primers in the gene were chosen to avoid repetitive sequence.

Amplifications were performed with AmpliTaq Gold DNA polymerase (Perkin Elmer, Foster City, Calif.) using a "hot start" to help ensure amplification specificity. Amplicons were sequenced in the Mayo Molecular Biology Core Facility with an ABI 377 DNA sequencer using BigDye™ (Perkin Elmer) dye-primer sequencing chemistry. Both DNA strands were sequenced in all cases. To exclude PCR-induced artifacts, independent amplification followed by DNA sequencing was performed for all samples in which a SNP was only observed once among the samples resequenced. DNA sequence chromatograms were analyzed using the PolyPhred 3.0 (Nickerson et al. *Nucl. Acids Res.* 25:2745-2751 (1997)) and Consed 8.0 (Gordon et al. *Genome Res.* 8:195-202 (1998)) programs developed by the University of Washington (Seattle, WA). The University of Wisconsin GCG software package, Version 10, was also used to analyze nucleotide sequence. GenBank accession numbers for the ASMT reference sequences were AF226730.

TABLE 1

PCR primers used for resequencing ASMT

| Primer Name | Primer Location | Primer Sequence (5' to 3' direction)* | SEQ ID NO: |
|---|---|---|---|
| UF(-783) M13 | 5'-FR | TGTAAAACGACGGCCAGTTCTGCAAGATGAAGTGACAATAC | 9 |
| UR(-275) M13 | 5'-FR | CAGGAAACAGCTATGACCTTGTTCGCTCCACTGCGATT | 10 |
| UF(-312) M13 | 5'-FR | TGTAAAACGACGGCCAGTACGAGATTTATCCGTGAAAATCGCA | 11 |
| I1R64 M13 | Intron 1 | CAGGAAACAGCTATGACCGGAGGCGCTCGCGTTCCCGCCTT | 12 |
| I1F86 M13 | Intron 1 | TGTAAAACGACGGCCAGTAGCTGTGTCTCGAGACCTTTGT | 13 |
| I3R84 M13 | Intron 3 | CAGGAAACAGCTATGACCGTTAATTCCCTAGTGACCTGCATCATTAT | 14 |
| I3F(-256) M13 | Intron 3 | TGTAAAACGACGGCCAGTTTATTTTAGATGGCTTATGAAGTCTTAGT | 15 |
| I4R172 M13 | Intron 4 | CAGGAAACAGCTATGACCTAATTGTTCAAGTTATCAGTTTCCAA | 16 |
| I4F101 M13 | Intron 4 | TGTAAAACGACGGCCAGTAGCTTCTAGTTAGCAATGCTCATTT | 17 |
| I5R33 M13 | Intron 5 | CAGGAAACAGCTATGACCGCTATAGTCATAACAGTAAGAATATAGA | 18 |
| I5F(-234) M13 | Intron 5 | TGTAAAACGACGGCCAGTTGCCTGATGTTATTTTCTGCACATTCAAACTT | 19 |
| I6R224 M13 | Intron 6 | CAGGAAACAGCTATGACCATTCAGTGACAACTGTCACCACGGATTTA | 20 |
| I6F(-179) M13 | Intron 6 | TGTAAAACGACGGCCAGTCCTTGGCACTTGACTATTGATTGTAA | 21 |
| I7R78M13 | Intron 7 | CAGGAAACAGCTATGACCATCCTGGCTATTAGCAGAAAGGAGTT | 22 |
| I7F(-277) M13 | Intron 7 | TGTAAAACGACGGCCAGTGTGGCGTACTGCATACATGAATATTAT | 23 |
| I8R115 M13 | Intron 8 | CAGGAAACAGCTATGACCCCAGATAACAGAAGTATCCCTCAAT | 24 |
| I8F9 M13 | Intron 8 | TGTAAAACGACGGCCAGTTGACAGACAGCAGGGACTATTATAA | 25 |
| I9R96 M13 | Intron 9 | CAGGAAACAGCTATGACCAGAAAAATGGGAGGCAATGCAAAGTCAA | 26 |
| I9F(-118) M13 | Intron 9 | TGTAAAACGACGGCCAGTCAGTGTGTAAGGATTAGTGCTGGT | 27 |
| I10R79M13 | Intron 10 | CAGGAAACAGCTATGACCGTCTGGGTGACAGAGAGAGACTCCA | 28 |
| I10F(-349) M13 | Intron 10 | TGTAAAACGACGGCCAGTGAGAAGTCGTTTTAGCATTTCCGTAT | 29 |
| DR1228M13 | 3'UTR | CAGGAAACAGCTATGACCCATTTGTTGTTTCTTATGGTCTGTGCTAT | 30 |

*underlined nucleotides indicate M13 tag

Recombinant ASMT Expression Constructs and Allozyme Expression: ASMT cDNA sequences for the three non-synonymous cSNPs observed during the resequencing experiments were created using the QuickChange Site-Directed Mutagenesis kit (Stratagene, La Jolla, Calif.), with the wild type ASMT cDNA open reading frame (ORF) in the pUni/V5-His-TOPO (pUni) vector (Invitrogen) as template. Specifically, the full-length wild type ORF was amplified using human brain Marathon-Ready cDNA (Clontech) as template. The resultant ASMT cDNA was subcloned into pUni, a vector that is only 2.3 kilobases in length and thus is well suited for performing "circular PCR" during site-directed mutagenesis. Site-directed mutagenesis was performed using internal primers that contained the variant nucleotide sequences. The ASMT cDNA inserts in pUni were excised and re-ligated into the eukaryotic expression vector p91023(b) (Wong et al. *Science* 228:810-815 (1985)). The sequences of inserts in p91023*(b) were confirmed by completely sequencing both strands.*

Expression constructs for the wild type and variant ASMT sequences were transfected into COS-1 cells using the TransFast reagent (Promega), with a 1:1 charge ratio. pSV-β-Galactosidase (Promega) was co-transfected as an internal control to make it possible to correct for transfection efficiency. The COS-1 cells were harvested after 48 hours and homogenized with a Polytron homogenizer (Brinkmann Instruments, Westbury, N.Y.) in 25 mM potassium phosphate buffer, pH 7.8 containing 1 mM dithiothreitol (DTT) and 1 mM EDTA. Cell homogenates were centrifuged at 15,000 x g for 15 minutes, and the resultant supernatant preparations were used for enzyme assays and substrate kinetic studies.

ASMT Enzyme Activity: ASMT activity was measured using the methods of Zakharayan et al. (*Chem. Res. Toxicol.* 8(8):1029-1038 (1995)). Briefly, 0.10 M Tris-HCl buffer (pH 8.0), 4 mM glutathione, 1 mM magnesium chloride, 2.5 mM sodium arsenite, 10 μM [$^{14}C-CH_3$]-S-adenosylmethionine, and recombinant enzyme were combined in a final volume of 250 μL. The cell homogenate preparations of recombinant ASMT allozymes described above were used for the activity studies without any further purification. The protein concentration of each recombinant protein preparation was determined by the dye-binding method of Bradford (*Anal. Biochem.* 72:248-254 (1976)) with bovine serum albumin as a standard. "Blank" samples included the same quantity of COS-1 15,000 x g supernatant from cells that were transfected with "empty" p91023(b) expression vector to correct for endogenous activity.

Reaction mixtures were incubated for 60 minutes at 37° C. and stopped by the addition of 750 μL 12 M HCl. The methylated arsenic compounds, products of the enzyme reaction, were isolated using the standard extraction procedure from Zakharyan et al., 1995, supra. Activities of recombinant ASMT allozymes were compared after correction for transfection efficiency by measuring the activity of cotransfected β-galatosidase using the β-Galactosidase Assay System (Promega) as described by the manufacturer.

Estimating Apparent $K_m$ Values: To estimate apparent $K_m$ values of ASMT for the sodium arsenite and SAM, a series of sodium arsenite and SAM concentrations were tested with the recombinant allozymes. Blanks for each substrate concentration were included by assaying COS-1 cell cytosol after transfection with empty p91023(b) vector. These data were fitted to a series of kinetic models, and the most appropriate model was selected on the basis of the dispersion of residuals and a determination of whether the F-test showed a significant reduction ($P<0.05$) in the residual sums of squares. Apparent $K_m$ values were calculated using the method of Wilkinson with a computer program written by Cleland. Wilkinson supra; and Cleland supra.

Western Blot Analysis: Quantitative Western blot analysis was performed with recombinant ASMT allozymes after expression in COS-1 cells. Polyclonal antibodies were generated against two synthetic polypeptides corresponding to ASMT amino acid residues 5-28 (RDAEIQKDVQTYYGQVLKRSADLQC; SEQ ID NO:31) and amino acid residues 341-360 (DIITDPFKLAEESDSMKSRC; SEQ ID NO:32). These antibodies were used to measure levels of immunoreactive ASMT protein with the ECL detection system (Amersham Pharmacia, Piscataway, N.J.). The quantity of COS-1 cell preparation loaded on the gel for each allozyme was adjusted to achieve equal quantities of β-galactosidase activity, i.e., gel loading was adjusted to correct for transfection efficiency. The AMBIS Radioanalytic Imaging System, Quant Probe Version 4.31 (Ambis, Inc., San Diego, Calif.) was used to quantitate immunoreactive protein in each lane, and those data were expressed as a percentage of the intensity of the wild type ASMT band on the gel.

Reporter Activity: VNTR sequences from the ASMT 5'-UTR were subcloned into the pGL3-basic luciferase reporter vector (Promega). The VNTR sequences were prepared by PCR amplification, using individual DNA samples from subjects with known VNTR genotypes as templates. PCR primers had the sequences 5'-AAGAAGGGTACCACGAGATTTATCCGTGAAAATCGCA-3' (SEQ ID NO:33) and AAGAAGCTCGAGAGGGAAGGGGCTGGGGGCT (SEQ ID NO:34). PCR products and pGL3-basic were digested with XhoI and Acc65I and ligated together.

Reporters were cotransfected into HepG2 and HEK293 cells (American Type Culture Collection, Manassas, Va.) using the TransFast™ reagent (Promega). The pRL-TK vector (Promega) was cotransfected as an internal control to correct for transfection efficiency. After 48 hours, cells were lysed and luciferase activity was measured using the Dual-Luciferase® Reporter Assay System (Promega).

Data Analysis: Statistical comparisons of data was performed by ANOVA with the StatView program, version 4.5 (Abacus Concepts, Inc., Berkeley, Calif.). Linkage analysis was performed after all DNA samples had been genotyped at each of the polymorphic sites observed, using the EH program developed by Terwilliger and Ott, *Handbook of Human Genetic Linkage*, The Johns Hopkins University Press, Baltimore, pp. 188-193 (1994). D' values, a quantitative method for reporting linkage data that is independent of allele frequency (Hartl and Clark *Principles of Population Genetics*, 3rd edition, Sinauer Associates, Inc., (Sunderland, Mass.), pp 96-106 (1997); and Hedrick Genetics of Populations, 2nd edition, Jones and Bartlett (Sudbury, Mass.), pp. 396-405 (2000)), were then calculated. The genotype data also were used to assign inferred haplotypes using a program based on the E-M algorithm (Long et al. *Am. J. Hum. Genet.* 56:799-810 (1995); and Excoffier and Slatkin *Mol. Biol. Evol.* 12:921-927 (1995)). Unambiguous haplotype assignment also was possible on the basis of genotype for samples that contained no more than one heterozygous polymorphism.

Example 2—ASMT Polymorphisms

Eleven separate PCR amplifications were performed for each of the 120 DNA samples studied. All PCR amplicons were sequenced on both strands, making it possible to verify the presence of polymorphisms using data from the complimentary strand. A total of 26 polymorphisms were observed (Table 2). Polymorphisms in exons, untranslated regions (UTR), and flanking regions (FR) are numbered relative to the adenine in the ASMTtranslation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1).

Variant allele frequencies ranged from 0.8% to 45%, with differences between the African-American and Caucasian-American subjects. Twenty-two polymorphisms were observed in 60 DNA samples from African-American subjects, while 21 were found in the 60 samples from Caucasian-American subjects. The overall number of ASMT polymorphisms per kilobase of sequence in the 120 samples studied (4.8 polymorphisms/kilobase, Table 3) was close to that (4.6/kilobase) observed in similar studies of other human genes (Halushka et al., *Nature Genet.*, 22:239-247 (1999)). Three of the SNPs were within the coding-region (cSNPs). All of these were nonsynonymous and resulted in the amino acid alterations Arg173Trp, Met287Thr, and Thr306Ile. The Arg173Trp polymorphism had a frequency of 0.8% in African-American subjects but was not observed in DNA from Caucasian subjects. The Met287Thr polymorphism had a frequency of 10.8% in African Americans, and 10% in Caucasians. The Thr306Ile polymorphism had a frequency of 0.8% in Caucasians but was not observed in DNA from African-American subjects. To exclude artifacts introduced by PCR-dependent misincorporation, independent amplifications were performed and the amplicons were sequenced in all cases in which a polymorphism was observed only once among the DNA samples studied.

TABLE 2

ASMT Polymorphisms

| Location | Nucleotide | Wild Type | Variant | Amino Acid | African American | Caucasian American |
|---|---|---|---|---|---|---|
| 5'-FR | −676 | T | C | | 0.000 | 0.017 |
| 5'-FR | −542 | G | A | | 0.025 | 0.000 |
| 5'-FR | −477 | A | G | | 0.317 | 0.383 |
| 5'-FR | −420 | C | G | | 0.008 | 0.000 |
| 5'-FR | −339 | T | C | | 0.108 | 0.217 |
| 5'-FR | −116 | C | A | | 0.008 | 0.000 |
| 5'-FR | −114 | G | C | | 0.242 | 0.117 |
| Intron 2 | I2(−75) | T | A | | 0.025 | 0.008 |
| Intron 2 | I2(−47) | D | I | C insertion | 0.267 | 0.208 |
| Intron 2 | I2(−10) | G | T | | 0.108 | 0.017 |
| Intron 3 | I3(−18) | G | A | | 0.000 | 0.008 |
| Intron 4 | I4(217) | A | G | | 0.058 | 0.008 |
| Intron 4 | I4(365) | G | A | | 0.042 | 0.000 |
| Intron 4 | I4(414) | T | C | | 0.100 | 0.008 |
| Intron 4 | I4(467) | A | T | | 0.067 | 0.008 |
| Exon 6 | 517 | C | T | Arg173 Trp | 0.008 | 0.000 |
| Intron 6 | I6(56) | A | G | | 0.108 | 0.100 |
| Intron 6 | I6(−56) | G | C | | 0.217 | 0.242 |
| Intron 8 | I8(154) | A | C | | 0.108 | 0.117 |
| Intron 8 | I8(213) | C | T | | 0.092 | 0.142 |
| Exon 9 | 860 | T | C | Met287 Thr | 0.108 | 0.100 |
| Intron 9 | I9(−50) | T | C | | 0.183 | 0.217 |
| Exon 10 | 917 | C | T | Thr306 Ile | 0.000 | 0.008 |
| Intron 10 | I10(−282) | C | T | | 0.267 | 0.350 |
| Intron 10 | I10(−189) | G | A | | 0.000 | 0.025 |
| Intron 10 | I10(−94) | G | A | | 0.375 | 0.450 |

TABLE 3

ASMT polymorphism frequencies

| | Total | African-American | Caucasian-American |
|---|---|---|---|
| SNPs/Kb | 4.8 | 4.0 | 3.8 |
| SNPs/Kb coding | 2.7 | 1.8 | 1.8 |
| SNPs/Kb non-coding | 5.3 | 4.6 | 4.4 |
| SNPs/Kb UTR | 41.2 | 35.3 | 23.5 |
| SNPs/Kb Intron | 4.7 | 4.1 | 4.4 |
| nonsyn/kb | 0.5 | 0.4 | 0.4 |

Example 3—Linkage disequilibrium and haplotype analysis

Linkage disequilibrium analysis was performed after all of the DNA samples had been genotyped at each of the polymorphic sites. Pairwise combinations of these polymorphisms were tested for linkage disequilibrium using the EH program developed by Terwilliger and Ott, *Handbook of Human Genetic Linkage*, The Johns Hopkins University Press, Baltimore, pp. 188-193 (1994). The output of this program was used to calculate D' values, a method for reporting linkage data that is independent of sample size. All pairwise combinations with a linkage disequilibrium greater than or equal to 1 in at least one population are shown in Table 4.

Twenty-two unequivocal haplotypes were identified by these studies (Table 5). The unequivocal haplotypes included seven haplotypes that were common to both ethnic groups, and fifteen that were ethnic specific (seven haplotypes were specific for African-American subjects; eight haplotypes were specific for Caucasian subjects).

TABLE 4

ASMT linkage disequilibrium analysis

| Polymorphism pair | | D' Value | p value |
|---|---|---|---|
| AA | | | |
| −477 | −339 | 1 | 0.000019 |
| −477 | −114 | 0.7652 | 0 |
| −477 | I6(56) | 1 | 0.000019 |
| −477 | 860 | 1 | 0.000019 |
| −477 | I10(−94) | 1 | 0 |
| −339 | −114 | 1 | 0 |
| −339 | I6(56) | 1 | 0 |
| −339 | 860 | 1 | 0 |
| −339 | I10(94) | 1 | 0.000151 |
| −114 | I2(−10) | 1 | 0 |
| −114 | I4(217) | 1 | 0.000072 |
| −114 | I4(414) | 1 | 0 |
| −114 | I4(467) | 1 | 0.000026 |
| −114 | I6(56) | 1 | 0 |
| −114 | 860 | 1 | 0 |
| −114 | I10(−94) | 1 | 0 |
| I2(−75) | I8(213) | 1 | 0.000907 |
| I2(−47) | I8(213) | 1 | 0.000036 |
| I2(−10) | I4(217) | 1 | 0 |
| I2(−10) | I4(365) | 1 | 0.000007 |
| I2(−10) | I4(414) | 1 | 0 |
| I2(−10) | I4(467) | 1 | 0 |
| I2(−10) | I10(−282) | 1 | 0.000001 |
| I2(−10) | I10(−94) | 1 | 0.000073 |
| I4(217) | I4(365) | 1 | 0 |
| I4(217) | I4(414) | 1 | 0 |
| I4(217) | I4(467) | 1 | 0 |
| I4(217) | I6(−56) | 1 | 0.000028 |
| I4(217) | I9(−50) | 1 | 0.000007 |
| I4(217) | I10(−282) | 1 | 0.000164 |
| I4(365) | I4(414) | 1 | 0.000006 |
| I4(365) | I4(467) | 1 | 0 |
| I4(365) | I6(−56) | 1 | 0.000545 |
| I4(365) | I9(−50) | 1 | 0.0002 |
| I4(414) | I4(467) | 1 | 0 |
| I4(414) | I6(−56) | 1 | 0 |
| I4(414) | I10(−282) | 1 | 0.000001 |
| I4(414) | I10(−94) | 1 | 0.000124 |
| I4(467) | I6(−56) | 1 | 0.000009 |
| I4(467) | I9(−50) | 1 | 0.000002 |
| I4(467) | I10(−282) | 1 | 0.000068 |
| I4(467) | I10(−94) | 1 | 0.000855 |
| I6(56) | 860 | 1 | 0 |
| I6(56) | I10(−94) | 1 | 0.000151 |
| I6(−56) | I8(213) | 1 | 0.000151 |
| I6(−56) | I10(−282) | 1 | 0 |
| I6(−56) | I10(−94) | 1 | 0 |
| I8(213) | I10(−282) | 1 | 0.000008 |
| I8(213) | I10(−94) | 1 | 0.000911 |
| 860 | I10(−94) | 1 | 0.000151 |
| I9(−50) | I10(−94) | 1 | 0 |
| I10(−282) | I10(−94) | 1 | 0 |
| CA | | | |
| −477 | −339 | 0.9276 | 0 |
| −477 | −114 | 1 | 0.000014 |
| −477 | I6(56) | 1 | 0.000082 |
| −477 | 860 | 1 | 0.000082 |
| −477 | I10(−94) | 0.9155 | 0 |

TABLE 4-continued

| ASMT linkage disequilibrium analysis | | | |
|---|---|---|---|
| Polymorphism pair | | D' Value | p value |
| −339 | −114 | 0.7938 | 0.000012 |
| −339 | I6(56) | 0.9773 | 0.000011 |
| −339 | 860 | 0.8773 | 0.000011 |
| −339 | I9(−50) | 0.4721 | 0.000063 |
| −339 | I10(94) | 0.8307 | 0.000003 |
| −114 | I6(56) | 1 | 0 |
| −114 | 860 | 1 | 0 |
| I6(56) | 860 | 0.9065 | 0 |
| I6(−56) | I8(213) | 1 | 0 |

TABLE 4-continued

| ASMT linkage disequilibrium analysis | | | |
|---|---|---|---|
| Polymorphism pair | | D' Value | p value |
| I6(−56) | I10(−282) | 0.9385 | 0 |
| I6(−56) | I10(−94) | 0.9185 | 0 |
| I8(213) | I10(−282) | 1 | 0 |
| I8(213) | I10(−94) | 1 | 0.000042 |
| 860 | I10(−94) | 1 | 0.000195 |
| I9(−50) | I10(−94) | 0.913 | 0 |
| I10(−282) | I10(−94) | 1 | 0 |

TABLE 5

ASMT haplotype analysis

| AA Freq. | CA Freq. | −676 | −477 | −339 | −114 | I2(−75) | I2(−47) | I2(−10) | I3(−18) | I4(217) | I4(365) |
|---|---|---|---|---|---|---|---|---|---|---|---|
| 0.5530 | 0.4365 | WT | WT | WT | WT | WT | WT | WT | WT | WT | WT |
| 0.0661 | 0.0276 | WT | V | V | V | WT | V | WT | WT | WT | WT |
| 0.0652 | 0.0599 | WT | V | WT | WT | WT | V | WT | WT | WT | WT |
| 0.0545 | 0.0622 | WT | WT | WT | WT | WT | WT | WT | WT | WT | WT |
| 0.0339 | 0.0264 | WT | V | V | V | WT | WT | WT | WT | WT | WT |
| 0.0277 | 0.0000 | WT | V | WT | V | WT | V | V | WT | WT | WT |
| 0.0158 | 0.0000 | WT | V | WT | V | WT | V | V | WT | V | V |
| 0.0100 | 0.1667 | WT | V | WT | WT | WT | WT | WT | WT | WT | WT |
| 0.0098 | 0.0000 | WT | V | WT | WT | V | V | WT | WT | WT | WT |
| 0.0092 | 0.0000 | WT | WT | WT | WT | WT | V | WT | WT | WT | WT |
| 0.0091 | 0.0000 | WT | V | WT | V | WT | V | V | WT | V | V |
| 0.0091 | 0.0000 | WT | V | WT | WT | WT | V | WT | WT | WT | WT |
| 0.0085 | 0.0833 | WT | V | WT | V | WT | WT | V | WT | V | V |
| 0.0083 | 0.0000 | WT | WT | WT | V | WT | WT | V | WT | V | V |
| 0.0000 | 0.0667 | WT | V | V | WT | WT | WT | WT | WT | WT | WT |
| 0.0000 | 0.0583 | WT | V | WT | WT | WT | WT | WT | WT | WT | WT |
| 0.0000 | 0.0470 | WT | WT | WT | WT | WT | WT | WT | WT | WT | WT |
| 0.0000 | 0.0127 | WT | V | V | V | WT | V | WT | WT | WT | WT |
| 0.0000 | 0.0097 | WT | V | V | WT | WT | V | WT | WT | WT | WT |
| 0.0000 | 0.0097 | WT | WT | WT | WT | WT | V | WT | WT | WT | WT |
| 0.0000 | 0.0097 | V | WT | WT | WT | WT | WT | WT | WT | WT | WT |
| 0.0000 | 0.0083 | WT | V | V | WT | WT | WT | WT | V | WT | WT |

| AA Freq. | CA Freq. | I4(414) | I4(467) | I6(56) | I6(−56) | I8(154) | I8(213) | 860 | I9(−50) | I10(−282) | I10(−94) |
|---|---|---|---|---|---|---|---|---|---|---|---|
| 0.5530 | 0.4365 | WT | WT | WT | WT | WT | WT | WT | WT | WT | WT |
| 0.0661 | 0.0276 | WT | WT | V | WT | WT | WT | V | WT | WT | V |
| 0.0652 | 0.0599 | WT | WT | WT | V | WT | V | WT | WT | V | V |
| 0.0545 | 0.0622 | WT | WT | WT | WT | V | WT | WT | WT | WT | WT |
| 0.0339 | 0.0264 | WT | WT | V | WT | WT | WT | V | WT | WT | V |
| 0.0277 | 0.0000 | V | WT | WT | V | WT | WT | WT | V | V | V |
| 0.0158 | 0.0000 | V | V | WT | V | V | WT | WT | V | V | V |
| 0.0100 | 0.1667 | WT | WT | WT | WT | WT | WT | WT | V | V | V |
| 0.0098 | 0.0000 | WT | WT | WT | V | WT | V | WT | WT | V | V |
| 0.0092 | 0.0000 | WT | WT | WT | WT | WT | WT | WT | WT | WT | WT |
| 0.0091 | 0.0000 | V | V | WT | V | WT | WT | WT | V | V | V |
| 0.0091 | 0.0000 | WT | WT | WT | WT | WT | WT | WT | V | V | V |
| 0.0085 | 0.0833 | V | V | WT | V | WT | WT | WT | V | V | V |
| 0.0083 | 0.0000 | V | V | WT | V | WT | WT | WT | V | V | V |
| 0.0000 | 0.0667 | WT | WT | WT | WT | WT | WT | WT | V | V | V |
| 0.0000 | 0.0583 | WT | WT | WT | V | WT | V | WT | WT | V | V |
| 0.0000 | 0.0470 | WT | WT | WT | V | WT | WT | WT | V | V | V |
| 0.0000 | 0.0127 | WT | WT | V | WT | V | WT | V | WT | WT | V |
| 0.0000 | 0.0097 | WT | WT | WT | WT | WT | WT | WT | V | V | V |
| 0.0000 | 0.0097 | WT | WT | WT | V | WT | WT | WT | V | V | V |
| 0.0000 | 0.0097 | WT | WT | WT | WT | WT | WT | WT | WT | WT | WT |
| 0.0000 | 0.0083 | WT | WT | WT | WT | WT | WT | WT | V | V | V |

Example 4—Activity of ASMT allozymes

Cell homogenate preparations containing recombinant ASMT allozymes, prepared from six independent COS-1 cell transfections as described in Example 1, were used to assess catalytic activity. The resulting activity was adjusted to a percentage of the WT ASMT enzyme activity, shown as mean ± SEM in Table 6. The activities of Arg173Trp, Met287Thr, and Thr306Ile were 31%, 350%, and 3.2% that of the WT ASMT enzyme, respectively. Western blotting revealed that the protein levels of the three allozymes were 20%, 190%, and 1.1% that of the WT ASMT enzyme, respectively. Thus, the effect of each cSNP on enzyme activity was at least partially accounted for by the effect on the protein level.

Alterations in amino acid sequence can alter enzyme substrate affinity and/or catalytic efficiency. Substrate kinetic studies were conducted to determine whether the Arg173Trp, Met287Thr, and Thr306Ile allozymes differed from the WT ASMT protein in these aspects. A series of sodium arsenite and SAM concentrations were used to estimate apparent $K_m$ values for recombinant wild type ASMT and for the three variant allozymes. These studies revealed a significant difference in apparent $K_m$ values between the WT ASMT protein and the Met287Thr allozyme for sodium arsenite (4.6 μM vs. 11 μM, respectively, $P < 0.05$; Table 6). There was no significant difference in apparent $K_m$ values between the WT protein and the Arg173Trp allozyme, and the Thr306Il3 allozyme was not used in kinetic studies.

TABLE 6

Human ASMT allozyme activity

| Allozyme | Enzyme Activity (% WT) | Immuno-reactive protein (% WT) | Sodium Arsenite Km, μM | SAM Km, μM |
|---|---|---|---|---|
| WT | 100 | 100 | 4.6 ± 0.56 | 12 ± 6.9 |
| Arg173Trp | 31 ± 2.6** | 20 ± 0.5** | 3.1 ± 0.8 | 8.9 ± 1.2 |
| Met287Thr | 350 ± 89* | 190 ± 14* | 11 ± 1.8* | 45 ± 0.9 |
| Thr306Ile | 3.2 ± 2.1** | 1.1 ± 0.6** | ND | ND |

*, P < 0.05; **, P < 0.001; ND, not determined

Example 5—ASMT 5'-UTR VNTR reporter activity

Further examination of the ASMT 5' flanking region revealed the presence of two or more VNTRs in the DNA from each subject. As shown in Table 7, Caucasian American subjects contained two or three VNTRs, while African American subjects contained two, three, or four VNTRs. The majority of subjects contained one two-repeat allele and one three-repeat allele, or were homozygous for the three-repeat allele.

TABLE 7

Human ASMT 5'-UTR VNTR

| Repeat Number | Allele Frequencies CA | AA |
|---|---|---|
| 2 (*V2) | 0.375 | 0.375 |
| 3 (*V3) | 0.625 | 0.558 |
| 4 (*V4) | 0 | 0.067 |

TABLE 7-continued

Human ASMT 5'-UTR VNTR

| Genotype | Genotype Frequencies CA | AA |
|---|---|---|
| *V2/*V2 | 0.183 | 0.100 |
| *V2/*V3 | 0.383 | 0.433 |
| *V2/*V4 | 0 | 0.117 |
| *V3/*V3 | 0.433 | 0.333 |
| *V3/*V4 | 0 | 0.017 |
| *V4/*V4 | 0 | 0 |

Each VNTR had one of two similar but not completely identical nucleotide sequences. The first sequence, designated as subunit A, was 36 nucleotides in length and had the sequence 5'-GTCGCAGGCCGAGGAGACAGTGAGTGCGCGCCCTGA-3' (SEQ ID NO:35) from the 5'-FR and exon 1. The second sequence, designated as subunit B, was 35 nucleotides in length and had the sequence 5'-GTCGCAGGCCGAGGAGACAGTGAGTGCGCGCCCTG-3' (SEQ ID NO:36) from exon 1 and intron 1. The DNA from each subject included at least one VNTR having the sequence of subunit B.

Figure 4A:
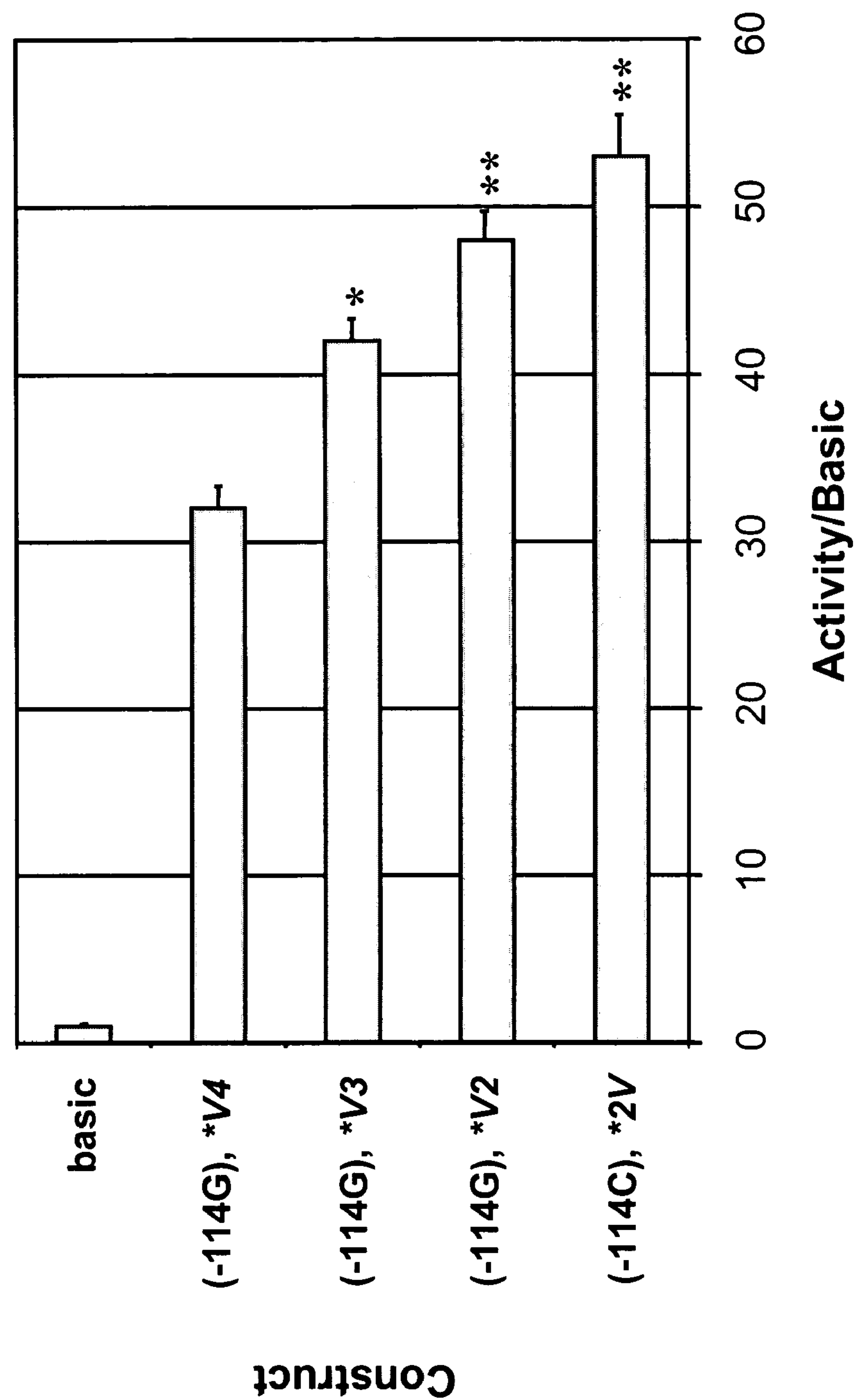
FIG. 4A is a graph showing levels of luciferase activity in extracts from HEK293 cells transfected with the indicated ASMT reporter plasmids.
Figure 4B:
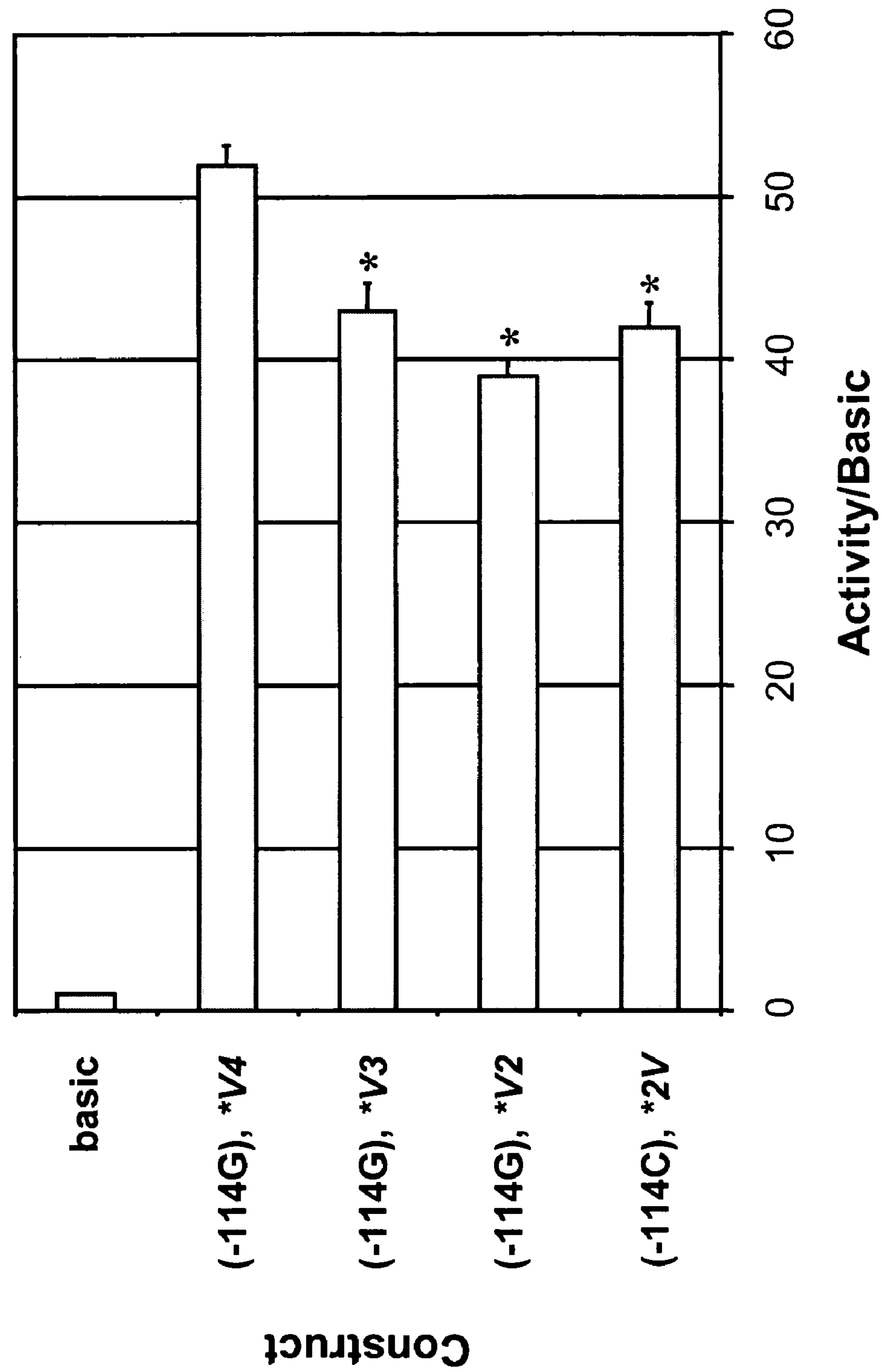
FIG. 4B is a graph showing levels of luciferase activity in extracts from HepG2 cells transfected with the indicated ASMT reporter plasmids.

Reporter constructs containing two, three, or four ASMT VNTRs were transfected into HepG2 and HEK293 cells as described in Example 1. Luciferase activity was measured after 48 hours of culture. The levels of reporter activity were expressed as the percent activity of the basic (i.e., empty) vector control, and are shown in FIGS. 4A and 4B. Construct names refer to repeat numbers, with *V2 containing one copy of subunit A and one copy of subunit B (configured as 5'-AB-3'), *V3 containing two copies of subunit A and one copy of subunit B (configured as 5'-AAB-3'), and *V4 containing three copies of subunit A and one copy of subunit B (configured as 5'-AAAB-3' ). Construct *2V contained two repeats (configured as 5'-AB-3') and had a substitution of cytosine for guanine at nucleotide −114. The variant at −114 was only observed in alleles with two VNTR subunits. The values graphed in FIGS. 4A and 4B represent mean ± SEM (n=4).

In these studies, all of the reporters resulted in luciferase activity that was dramatically increased as compared to that of the vector control. In HepG2 cells (FIG. 4A), a decrease in the number of VNTRs resulted in gradually increased reporter activity. The construct containing four VNTRs had significantly less activity than those containing three or two VNTRs. The combination of two VNTRs with a cytosine at position −114 (reporter *2V) resulted in the greatest level of luciferase activity. The opposite effect was observed in HEK293 cells, where the reporter activity of the construct containing four VNTRs was significantly greater than the activity of the other constructs. Thus, the effect of repeat number may be determined by factors specific to each type of cell.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting essentially of a variant ASMT nucleic acid sequence, wherein said variant ASMT nucleic acid sequence is:

(a) at least fifteen contiguous nucleotides of SEQ ID NO:1, wherein said sequence includes one or more of nucleotide positions 8011, 12327, and 23936 of SEQ ID NO:1, with the proviso that the nucleotide at position 8011 of SEQ ID NO:1 is thymine, the nucleotide at position 12327 of SEQ ID NO:1 is cytosine, or the nucleotide at position 23936 of SEQ ID NO:1 is thymine; or (b) the complement of (a).

2. The isolated nucleic acid molecule of claim 1, wherein said variant ASMT nucleic acid sequence is at least fifteen contiguous nucleotides of SEQ ID NO:1, wherein said sequence includes position 8011 of SEQ ID NO:1, with the proviso that the nucleotide at position 8011 of SEQ ID NO:1 is thymine.

3. The isolated nucleic acid molecule of claim 1, wherein said variant ASMT nucleic acid sequence is at least fifteen contiguous nucleotides of SEQ ID NO:1 wherein said sequence includes position 12327 of SEQ ID NO:1, with the proviso that the nucleotide at position 12327 of SEQ ID NO:1 is cytosine.

4. The isolated nucleic acid molecule of claim 1, wherein said variant ASMT nucleic acid sequence is at least fifteen contiguous nucleotides of SEQ ID NO:1, wherein said sequence includes position 23936 of SEQ ID NO:1, with the proviso that the nucleotide at position 23936 of SEQ ID NO:1 is thymine.

5. A isolated nucleic acid encoding an ASMT polypeptide, wherein said polypeptide consists of an ASMT amino acids sequence variant relative to the amino acid sequences of SEQ ID NO: 5, and wherein said amino acid sequence variant is a tryptophan at residue 173, a threonine at residue 287, or an isoleucine at residue 306.

6. The isolated nucleic acid molecule of claim 1, wherein the isolated nucleic acid molecule is from 15 to 100 nucleotides in length.

7. The isolated nucleic acid molecule of claim 6, wherein the isolated nucleic acid molecule is from 20 to 50 nucleotides in length.

8. A vector comprising the isolated nucleic acid molecule of claim 1.

9. The vector of claim 8, wherein the isolated nucleic acid molecule is from 20 to 50 nucleotides in length.

* * * * *

SEQUENCE LISTING

<160> NUMBER OF SEQ ID NOS: 36

<210> SEQ ID NO 1
<211> LENGTH: 34500
<212> TYPE: DNA
<213> ORGANISM: Homo Sapiens

<400> SEQUENCE: 1

```
aagggtaggg gagaaaattt ctatgtatgt tagtttttta tcttaaaaaa attagctttt     60
gtgaggctgg gcgtggtggc tcacgcctgt aatcccagca ctttgggagg ccgaggcggg    120
cagatcacga ggtctggaga ttgagaccgt cctggctaac acagtgaaac cccgtctcta    180
ctaaaaatac aaaaaattag ctgggcgtgg tggcgggcgc ctgtagtccc agctattcgg    240
gaggtgaggc agtagaatgg catgaacccg ggaggcggag cttgcagtga gctgagatcc    300
tgccactgca ctccagcctg ggtgacagag cgagactctg tctcaaaaaa ataaaaaagc    360
ttttgccaat atttaaaata tgacttgatg tgagagtctt aatttcttct acgcagtata    420
cagatatata gcattcctgt catttagcag ggtgatagt aaaacaaaaa aacaaaaaac    480
cccacaaaac ctgtggtgag gcactgacca atcagaatga ttgatggtca cagtctggtc    540
caaaattagc ccccacacca gacaccatgg aggaaaagtg agagtaactc aatttaagtt    600
gacagtggtt tgttttattg cagtttatct gtgtgtgaat aggtagattt aaggattgtt    660
ggccaggtgt ggtggctcac acctggaatc ccagcacttt taggaggcag aggcaggcgg    720
atcacttgag atcaggagtt cgagacagcc tggccaacat ggtgaaaccc tgtctctact    780
aaaaatacaa attagccagg catggtagtg catgcctgta attccagcta cttgggaggc    840
tgaggcagga gaatcgcttg aaccggggag gcagaggttg cagtgagccg agattgcgcc    900
attgcgctcc agcttgggca acaagagcga aactctgtct caaaaaaaaa aaaaaaaaaa    960
aaggattgtc aaatgattct tgtaagtaaa ccataaatta aagataacaa aacaagcaca   1020
agagaaaaat gatacagccc tttccttgac ctctcactaa tctgcccttt taagataaag   1080
atatcatttt aactatgaga aggtaactgc ttttctaaag gagctcattt tatgaagata   1140
atattttgaa aactaatatt taggagtgtt ttcaccattc tatgattgcc caaaaactaa   1200
gtgatactta taaaaacact aagttttata catatactag ttggaaatat tccaagctgt   1260
agaaatattc caacaaggat tatttccatg ggttaattt gttaaaaata taaaagacac   1320
cacctttcta ttaatttgta acaactaatt gacatcagag aagatgaaaa tttactagct   1380
ggatatcaac cagatttttg tattattggc aactgagatt gaaaaatgaa tgaaagagtc   1440
tacttcatcc atttagatat cctttcactt ggatctccct gtttccttac tgtcctaatg   1500
aatagaaatg atcgttacaa gctgggcatg gtggcttgca cctgtagtcc cagctactgg   1560
ggaggctgag gagggaggat ggcttgaggc cagagttgaa ggatccagag atgattgcgc   1620
agtgacgcta agcttgggcc acagagttga gaccctgtct ctaaaaattt ttttttaatt   1680
taaattataa aaagagaaat gcttgttaca accacaaagg gaaacaagat atacacatat   1740
aattgtggaa gtaaaaataa ataatttaaa aatacttttg ggtgctcgct tcggcagcac   1800
atatagttgg aatgatagag aagatttgca tggcccctgc gcaagatgac atacaaattc   1860
gtgaagtgtt ccatatttaa aaaaacaaaa aatacttttg ggcctggcac tgtggctcat   1920
gcctgtaatc caaacacttt gggaggctga ggcgggcgga ttgcttgaac ccaggagttg   1980
gagaccagcc tggacaacat ggtgaaatcc cgtctctata aaaaaataca aaaattaacc   2040
```

-continued

```
aggtgtggtg gtgcacgcct gtaatccaag gtacttggga ggctgaggcg ggaggatcgc   2100
ttgagccagg aggttgggcc tgggtaacag agaccgtctc aaaaaaattt aaaaattaaa   2160
aaaaaaactt tctgcaagat gaagtgacaa tacctggaaa atacatgtga cttgaccaaa   2220
aattactata ggtgaaaata aatttagcaa agttgctttc ctaaatacaa cccaaaatag   2280
actgggaaca gctacatact gttaatggtt ccctctatgt gacattctag aaaaggcaga   2340
actataggga gggaaaacat ctgtggttgc ccaggagcta ggggtgggaa gagggaattt   2400
actacaaaga ggcacgaaga aacttgtggg ccagagctat tttggtctcc gttttggtga   2460
tgtatatacg tttgccagag ttcacagaac tgcacactga agaaagatgg atttcacgga   2520
atgtgaatta tatctcaaca aacttgactt caaaaaacag atcgagaaaa gatgattcta   2580
ttcccaaaaa gggggagggg ggaagatcat tatataggtg agtgttcatt taaatcagag   2640
tacgagattt atccgtgaaa atcgcagtgg agcgaacaag gggatgctg ataccgacct    2700
cctggttgga aagcctgtag agcagcgcgg atgacagtgg aacagcgggt caggcggtgg   2760
gcgcctgagc gaggggctag agcgggatgg gcgggcggag caagcctgcc agcctgggcg   2820
gggcctcggc acaggagctg gctgcgggag cccgccgtcc tgagtcgcag gccgaggaga   2880
cagtgagtgc gcgccctgag tcgcaggccg aggagacagt gagtgcgcgc cctgagtcgc   2940
aggccgagga gacagtgagt gcgcgccctg ggcgccccgc cccagccccc agccccttcc   3000
ctgggccccc gcaaggcggg aacgcgagcg cctcccccga gctgtgtctc gagacctttg   3060
tcctcccctc accccctcggc ccgctgcctg ccctttactg gccccctccc tcatgcccgt  3120
ccctcagcac cctctccttt caactaactt tcccgctccc gacagtggct gcacttcgtg   3180
acgctgagat acagaaggac gtgcaggtga gagctgtagg gcctggaatg gcccaagtgg   3240
agcctaggct aatggaagtc tggcctggcc cgcaccctgt cccccgggac tcctggagtc   3300
ggggtagggc agggtctagg cttcgacctt tccagggaac tgaggtcggc caagtggagg   3360
tggaggtggt gacggagccc tcgcgctgca gtcacagctc ttctccctct ctacccctca   3420
ctccactgtg ggacgctggg tcagacctac tacgggcagg tgctgaagag atcggcagac   3480
ctccagacca acggctgtgt caccacagcc aggccggtcc ccaagcacat ccgggaagcc   3540
ttgcaaaatg tacacgaaga agtagcccta aggtagagtg ccctgtgctg tccccaggaa   3600
gaccccaaac agcagttttc ccaaaagata atgatgcagg tcactaggga attaacccgt   3660
agccaccaac ccatcagctt gccttgtcta ttgtaaaaat cctaaatctc agcacccatc   3720
atcttactgc tctaagaacc tccgatgagt ctgggcgcgc cagtgagcct gtagtcccaa   3780
gtgcttggga ggctgaggca gaggatcgcg tgagcccaga agttacaggc tgtagtgtgc   3840
gatccgggat gtgaatagcc actgcactcc agcttggtca acatagccag atgcatctct   3900
aaaataaatg cgtactttaa aaaaattgcc taaaaaaaag aacctccagc gtgaacactc   3960
tgtagtccct acccatgctc acagaataca gtcacactca ctggatctgc cattcaagat   4020
atgcgcagtt cagcacccac taatcaacct tggccctttt gacccttccc ttcctcactc   4080
catcagcact gcctgcccag ccggcagtca ccaatttgga aggtcttccc ttttcttttt   4140
ccttcccaac cctgcgcatc cagcaccacg ctgctgtccc acctactgca tggagccttc   4200
tctaatcctt gagcggcctc ttccccaaac tgccacagca ctctgtcact cggtctgtcc   4260
gtaaatcacg ggaagtgttt tctgtgcacg atgttttatc tcgcctctca aatacaccta   4320
cgcggcgggg agcggtggct cacgtccgtc atcccagaac ttgggaggcc aaggcaggta   4380
```

-continued

```
gatcacttga ggtcagaagt tcaagaccga cctggtcaac atagtgaaac cctgtctcta   4440

ctgaaaatac aaaaattagc tgggtgtagt ggggcacgcc tgtagtccca gctacttggg   4500

aggctgaggg aggagaatca cttgaacgtg gaaggcggag gtcgcagtga gcggagattg   4560

tgccactgca ctccagcctg ggcaacagag aaaaactcag tcaaaacaaa acaaaacaaa   4620

aaaaaggccg gggtggtgg cttatgtctg taatcccagc actttgggag gccgaggcgg   4680

gaggatcacg aggccaggag atcgagacca tcctggctat catggtgaaa ccccgtctct   4740

actaaaaata caaaaatatt atccgggtgt ggcggcacgc gcctgtagtt ccggctgctg   4800

gggaggctga ggcaggagaa cggcgtgaac ccgggaggcg gagcttgcag tgagctgagt   4860

tcgagccact gcactccagc ctgggtgaca gggcaagact ccgtctcaaa aaaaaaaaaa   4920

aaaaaaaaaa aaaaaaaaat tagccaggag tggtggcagg cgctcgtagt cctagctact   4980

cgggaggctg aggtaggaga atggtgtcaa cccgggaggc ggagcttgcg gtgagctgag   5040

atcgcgccac tgcactccag cctgggcgac agagcgagac tccgtctcaa acaaaacaaa   5100

acaaaacaaa acaaaacaaa tcaaaacaaa aaacgcctat gggacagaaa ccttacattt   5160

tttcctcaat aactagcgca gtcctgggcc tgaattagaa gctcagctaa tgattaaatg   5220

tatttattca acacattatt ttattttatt tatttatttt tgagacggag tctcactctg   5280

tcccttaggc tggagtgcag tggcgccatc tctgctcact gcaacctctg cctcctgggt   5340

tcaagccatt ctcctgcctc agcctcccga ggagctggga ttacaggtac ctgctaccgt   5400

gcccagctga ttttttggta tttttagtag agacagggtt tcactatgtt ggccaggctg   5460

gtctccaact ccttgcctca agcgatccgc ctgccttgac ctcccaaagt gctgtgatta   5520

taggcgtgag ccaccgcgcc cagcctgaac acattatttt agatggctta tgaagtctta   5580

gtgcctagca catgcccaac aatactgtgg taaagcagat acagtcccag ccttcatggg   5640

tgtccagttc agtggagact aaacatcaga agtatgagtg aatgatgcaa gaaagaagga   5700

aggaaggaag gaacggaggg agggagggag gagggaagta tgtataagat ttagtggttt   5760

catgtcttac agtctccagg gaaaaaatat gtgttttcca tttcccagat attatggctg   5820

tggtctggtg atccctgagc atctagaaaa ctgctggatt ttggatctgg gtagtggaag   5880

tggcagagat tgctatgtac ttagccagct ggttggtgaa aaaggacacg tgactggaat   5940

agacatgacc aaaggccagg tgaggcatga tttggaagac aaggagaaaa agattctcaa   6000

aagcattatt tgaaaaataa agttgttttc ttcgtggctc ttcaaggata atttaagaaa   6060

gcttctagtt agcaatgctc atttgtgcca ctagtgcttc ctgtcttgga aactgataac   6120

ttgaacaatt aggggttctt ctgggcgaac acaagagtcg gaggtttgct ctgatatgaa   6180

tatcgtgacg atagagtgga ctttgatctt tcccttcttg ctgccatcta tcctgaaaga   6240

ttttgttatt gaatgaggag tttattcaag ccaaactgca cgggcagcag ggagtttatg   6300

tcccaggttg tagtatatcc tacgtgtcca caggaatctt gtatgtttat ccaaaataat   6360

ctaggggaag tatattctgt tagtgatagg aaatttttag gaaaaagttg tgtatttttt   6420

tcaaaatgtt atcaaaacta tatttttctt actttaggtg gaagtggctg aaaagtatct   6480

tgactatcac atggaaaaat atggcttcca ggcatctaat gtgactttta ttcatggcta   6540

cattgagaag ttgggagagg ctggaatcaa gaatgagagc catgatattg ttgtgtaggt   6600

ctatattctt actgttatga ctatagccca ttttctttat tattattatt attattattg   6660

agatggactc tcgctctgtc acccaggcca gagtgcagtg gcccaatgtc agctcacgat   6720

aacctctgcc tcccgggttc aactgattct cttgcctcag cctctcaagt agctgggatt   6780
```

-continued

```
ataggcacac gctaccacat ccagctaatt ttttaaatct tcttttagta gagacagggt   6840
ttcaccatgt tggccaggct ggtctcaaac tcctgatctc aggtgatcca cccgcttcca   6900
cctcccaaag tgctgggatt acaggtgtga ggcactgtgc tcagccctca tttccttttg   6960
aacacagaga tgtcactatt actgtttgct gaattgactc tcatttaggg tgttaaacta   7020
aacttagcat ggcttactaa tgggagagag ctggtttgag ctgctggagc tcaccagcag   7080
cagaacacac cagaccaaga gggaacttac ttgaaactta accacaaacc aatgaaccca   7140
aaagaccagc aggaccacta agtttgctcc tacaatacat gctgacctgt atctttcata   7200
atattttcat ggtaaattat aggattctat ttcctttttt ccctcaagtt gttattgtca   7260
aatcatgccc aagtgacagc tgcctttgag gaacatagcc tgtttacgtg aagcataaga   7320
aatgccttgt gccggccagg tgcggtggct cacgcctata atcccagcat tttgggaggc   7380
cgaggcaggt ggatcacgag gtcaggaatt ccagaccagc ttgaacaaca tggcgaaacc   7440
ccgtctctac taaaaataca aaaattagct gggtgtggtg gcacatgcct gtaatcccag   7500
ctatttagga ggctgaggca ggagaatcac ttgaacccgg gaggcggagg ttgcaatgag   7560
ccgagattgc gccattgtac tccagcctgg gcaacaggag tgaaacatcc tctcgggaaa   7620
aaaaaaaaaa gaaagaaatg ccttgtgcag taggcatctg gtctgaggtt tcatcttgtt   7680
acatggtgaa catcaggaca gaaacaagta agaatcatgc ctgatgttat tttctgcaca   7740
ttcaaacttg ctaacaattt attgagattt taagcactct gtctctgatc ttggggaaaa   7800
gcttagttga aggcattaga aagagaggag ggaggcggta agaatggggt agctttgaca   7860
gaacggtggg aaccaccttt agggtctgaa aggatttgca gatctctgag tgttgtgaag   7920
atttgctcga catttcatct gttctctttt agatcaaact gtgttattaa ccttgtgcct   7980
gataaacaac aagtgcttca ggaggcatat cgggtgctga aggtgaggag gagagtgaga   8040
taaattatct ttgaacatca gtaagagctg atgggttaag tcttgtttgt tccccccttga   8100
actaagagct caaactctct taatttatcc attaaatgaa taaggggtgg caaaaggggg   8160
aaggggcagg aataccccgg atatggatta ctttccctct taggttgcaa aaggtagtaa   8220
atccgaggtg acagttgtca ctgaatgtgt taaggtattt gctttcttga ctgtctctcc   8280
tatttgctgc tgtacatgat cctagaagag catctgtgga gctataggaa tctttgcact   8340
gactactaat gattgctttg aatatactct cttctagcat gtacagtgtt tctcagggct   8400
tctgatttct tatctgtcat gatttcagat ctttgggaag ttacagaaga tggaactttt   8460
acattaacta cttgctaaaa ggaaagcttg caggagctcc acagccttca ttgtatcatg   8520
agatgtgtat cttcatgata gtagatgaaa tattcagcca ggtgcggtag ctcacacctg   8580
taatcccagt gctgtgggag gccgaggcgg gcagatcacc tgaggtcagg agtttgagac   8640
cagcttggcc aacatggaga aactctgtct ctactaaaaa tacaaaaatt agctgggtgt   8700
ggtggtgcgt gcctgtaatc ccagctcctc gggaggctga ggtaggagaa tagcttgaac   8760
ccagaagtca gaggttgcag tgagccagga tcgtgccact gcactccagc ctgggagaca   8820
gagcgagact ccatctcaaa aaaaaaaaaa aaaaaaaaag attctagctg ggtgggtggt   8880
acatgcctgt actcccagct acttggatgc tgaggcaaga ggattgcttg agctctggag   8940
tttgtgtgca gcttgggcaa tatagtgtga tcactgcctc taaaaaaatg ttttttttt   9000
tgagatggag tctcactctg ctgtccaggc tgtagtgcag tggcaggatt tcatctcact   9060
gcaacctccg cctcctgggt tcaaacaatt cttttgcctc agcctcccta gtagctggga   9120
```

-continued

```
ctacaggcgt gtgccaccat gcccagctaa tttttgtact tttagtagag acaagatttc   9180
accatattgg tcaggctgat cttgaactcc tgatctcatg atctgcctca gcctcccaaa   9240
gtgctgggat tacaggcatg agccgctgtg cctggccaaa attttttttt aaattgacaa   9300
cagatttttg agatttttgg tttacaaagc tgtcatagaa ctcaaataca aatatctata   9360
tagaaatgat ttaatgattt agtgatgtct ttgttagtat gtcattttac acgccagttc   9420
actatctcca ccaaaaatgt acttataaaa ggtagaaaca ctattataga atctagatct   9480
ccaggtttcc aggtttttga aattagctaa ataaaatgtt aagttcctga tcactcattt   9540
gccttacatt ttaaggataa tattttaaag ataaaatgtg ttgttataaa agtaaataac   9600
aacattacaa aaagttatat tttttaatag aaatggggtc ttgctgtcac ccaggctgga   9660
atgcagtgtc actatctgta cccctctaac tcctgagtta gaggggtcca gatagtgaca   9720
ctcactgtac cctctaactc ctgggctcaa acaatcctct tgagtagcta ggactccagg   9780
cacatgccac catgcccagc tagtttttaa atttctatat gggagagagg gtcttgctgt   9840
gttgccaagg ctagtctcaa actgctctcc tccagcaagc ctcccacttc ggcctcctga   9900
gtcattggga ttagaggcct gagccatcat acctggcaaa gttatactat tcttaagaga   9960
taaaagatta tgaatactga tgatatcctc tgttctacaa tgacctgggg ctgcttttgg  10020
ttcagattgg ctaaaaattt aaatgtaagt aacctgaaaa tctttattta ggagacagac  10080
actcttagaa tgtgatttta ttacctgttg gataagccac tgggaggaaa aaaaaccttg  10140
gcacttgact attgattgta actaaagagg cagctgctat ttgttcacaa agggtcagct  10200
taaacattgc tattgatttt taaatttgat tttgttcccc tattcctttc tttgttatgt  10260
ggggtcaatg taatcattaa tcatcttgtt tggactaata tgcctctgtt tcagcatggt  10320
ggggagttat atttcagtga cgtctatacg agccttgaac tgccagaaga aatcaggaca  10380
cacaaagttt tatggggtag gtgattttgt ttagtttagt attaaggcag atggttgtac  10440
atgtgcagaa ctcctttctg ctaatagcca ggatgaggct atatgagatc acatggggtt  10500
aggccatgag gccaaggttc cattcttcct ctgccattca aaagtgatag ggctttggat  10560
agtttaattc atctctttga gttatcgttt tccaaattgt aaaatgtaaa taataataca  10620
atctgcctta tagggctgtt atgaagatta aatgggataa agaatgggaa aaatactttg  10680
aaaactctag tgtggaaatg aggacaattg ttcccaagct ggtgtcctct tagtcccctt  10740
atgttctcat cattattgtg ttctttattc ctttattatc attttaatag tctggaagtt  10800
gagataaatg catgcttttc atcagtctat gaaatcaaaa gttcttattc ttaaaataat  10860
attaacttta ttcttactat gtaataataa ataggtaccg ttaacaagtt ggaaagtgcc  10920
aaaaaaaaaa aaaaaaaaga aaaaattact aagctggaca cagtggcaca cacctgtaac  10980
cccagatatt tgggaggctg agtcaggagg attgcttgag cctaggagtt caggtacagc  11040
ctgggtgtca tagtaaaacc ctatctctta aaaaaattac ttataatcat ataacccagt  11100
gataacttct tttttttttt tttttttttt tgagatggag tctcgctctg tcacccaggc  11160
tagagtgcag tggcgcaatc ttggctcact gcaacctcca cttcccgggt tcaagtgatt  11220
ctcctgcctc agcctcccaa gtagctggga ttacaggtgc atgccaccat gcccagctaa  11280
tttttgtatt tttagtagag atggggtttc actgtgttgg ccaggctggt ctccaacacc  11340
tgacctcatg atctgcccac ctcggcctcc caaagtgctg ggattacagg catgagccac  11400
cgcgctcggc ctatgattta ttttttatac tactttattc acataacagt gcttttcaga  11460
atgtggcgta ctgcatacat gaatattatg cttgcagctg agtagaacca atccaccagt  11520
```

-continued

```
gagtgtcctg aagaatggtt cctagagacc atcagctagc acacccagtc ttaaccatgg  11580
ctttctagac cttggaggga tgctcaagtt agcttctact gctaggatct atgttttaac  11640
taataccatg tcctaattaa ttatatagaa gaatagttcc cttaatactg tattaagtgt  11700
tggctggtct gtggtttttt gttgttgttt gtttttttagg tgagtgtctg ggtggtgctt  11760
tatactggaa ggaacttgct gtccttgctc aaaaaattgg gttctgccct ccacgtttgg  11820
tcactgccaa tctcattaca attcaaaaca aggaactgga aagagttatc ggtaagatat  11880
gacagacagc agggactatt ataactacag cttgaatgat tgaaatgtgg tgattagtaa  11940
gtaacttctg aaggagtctc attgagggat actttctgtt atctggaaat agctatcttg  12000
cctcctgtac aatggtaacc ccccaaaaat tttgatattt aataaagcac tttgaagtca  12060
ttcagtaaat agagtgaagt gctcagaaag ataactgatg acatgcaagg aagaaaatca  12120
tctttataac gtgtttgctc cttgtctgct gagcaaggca acaactgggg gagtgctgga  12180
gatgaaccgt gaataaattc tatttttagg tgactgtcgt tttgtttctg caacatttcg  12240
cctcttcaaa cactctaaga caggaccaac caagagatgc caagttattt acaatggagg  12300
aattacagga catgaaaaag aactaatgtt tgatgccaat tttacattta aggtaaataa  12360
aacaatttcc atgacttctg gtattctttc tgctcttgcc cttgctccag ctatcttttc  12420
ttgactttgc attgcctccc atttttctgg tgttggtttg tttgtgtgtg tgtttaaatg  12480
tatgtgtgtg tttcaagtgg agtaaaaaag catttttttcc ccaatactta tttatttatt  12540
gacagggtct cgctctgtca cccaggctgg agtgcagtag cacaatcata gttcactgca  12600
gcctgacctc ctgggctcaa gcgatcctcc cacctcaggc ttctgagtag ctaggactac  12660
agactcatca ccacacctgg ctaatatttg tattttttgt agagatgggg ttttgccatg  12720
ttgcccagac tggtcttgaa ctcctgggct caagtgatgt gcccacctca gcctcccaaa  12780
gtgctgggat tacaggcgtg aaccaccgtg cccagccctc aatatttatt ataaaaatgt  12840
ttttggccag gtgcggtggc tcacacctgt aatcctagca ctttgggagg ctgaggcagg  12900
cagattacct gaggtcagga gttcgagacc agcctgacga acatggcgaa aacccatctc  12960
tactaataaa aatacaaaaa ttagccgggc gtggtggtgg gtgcctgtaa tcccaactac  13020
tctggaggct gaggcaggag aattgcatga acccgggagg tggaggttga ggtgagctga  13080
gatcatgcca ttgcactcca gcctgggcaa cagagtgaga ctccatctca aaaaaaaaaa  13140
aaaaaaaaga agtttttgaa tacagaaaag ttaatagtac aatgaatacc cacataggca  13200
ttacctatat ttcagcaatt gagaacattt ttccatgttt gtgtgtttat atgtgtatat  13260
atatatatat atttatttgc tgagccattg aaaataagtt gcagatatta tgacatttta  13320
cccttaaata tttcagcatg cgtcccatag gaatgtaata tccctctgca taatcacaat  13380
accattacac acctaagaaa actttttaca agaagcctca ttcagacatt ggattaatag  13440
ggctatagag aagtaggatg gaaaagagta ggagtatgta caatagtatt tcaattgttt  13500
aattgtgtca aggaattaag aaattttaat gttggatgat ggcactaatt ggcattttta  13560
ctgccctgtg catagtaaga tttgttttct caaaatggaa aagttcaggc tttggaatca  13620
gatacctggg ttcaaattct ggctctatta ttattgtttt ttattttttt ttctgaatgt  13680
cactagacaa acttttattg aagcataaat tgtggtacag aaatacattt taactgattt  13740
aagtccaaca ccagtgaaag gagagattat ggcaccaaaa ctttcccttt cctatcatac  13800
catgatttag attatgatgc aatctacatt tctcttttct aggctttgtc ccatacaaat  13860
```

-continued

```
ttgggcagtt tttcaacatt agaatttcaa cattagaatt cttaattcta ttaggaaaaa  13920
aagcaacaaa aaaaccagac ctcaagtcaa caaatctatt ggatattgtt tatgaacgaa  13980
gtccacgtta agcattggtc ctcaaaacag agctcctcaa aatattaggt gctgtgctca  14040
ttacagaatc aaactgatca cactgattga aaacttcctc aatgaaattt tcaatcaaca  14100
acatgcttca aataaaagtc aaacagtgtt ccaaccactt gacttcaaac caagtagatt  14160
ttaggtttag aaacactaaa aaaaggtgtt tcatttataa atacagaagg aacaaaaaca  14220
tcactgcatc aatccagaaa ttatcaaaat atttagagga caagaaatat aaaatttagt  14280
caactttgct gctttctcag ttccttaaaa tcccagagta tctgcaaata tagctaaaaa  14340
gtaccaactc ttgaaagcct atattactag tcatttccca ttgagtattt tggaatttta  14400
tttatgttct acttatttat tcatgtattc tgctttatga tgtttatctg aataatctgg  14460
acaaattctc attctgggca gtcattcgtt tcatcctatg aatgccatgg tgagggaaac  14520
agtgtagtta gaggaacaga tgaagtcaga acactcacat gcatcacggt cacagaactt  14580
taagtcacaa gacagaaaag aaatcgattc tgctttggat caaagtttat agaacactac  14640
ttaatggaaa ctagtggaaa tggctgctaa aggaaaagtt aaggtgaatg atccaagctg  14700
acttgattac tgaatccaga acaaaattat gctaaatctc tctggtaatt aactaaataa  14760
aaatcatttt atactattat ttagtaagtt agtaaaggcg tgctactcat tagatgctaa  14820
tctcatttac tgaggaacac agaattgtat atgttttctg gctctattat ttattacttg  14880
ggtaaacttg aacaagtcac caaaattcgt tgggttacag tttgttctac tgtaaaagca  14940
gggataataa tacttacttt gcagaatttc tataaggatt agcaataatg tagcaaaaca  15000
ctgggtacat actgcaagtt cagtgaaaag aagatactgt cattatttgt tccaaaagtg  15060
gaagaactta ctattaatat ttcatttttc tgatttattt atttatctat tttagagaca  15120
aagtctctct ctgtcaccca tgctggagtg tagtggcaca gtcatagctc actgtaacct  15180
caaactcctg ggctcaagcg attctcccat ctcagcctcc caagtagctg ggactacagg  15240
catgtgtcac catgcctggc taattttttta tttttatttt tttgttggtg agacaggttt  15300
ttttttttt tcttttttga gaccaagtct cgctctgtca ctcaggctgg agtgcagtgg  15360
cccgatctcg gctcactgca agctccacct cccgggttca cgccattctc ctgccttagc  15420
ctcccaagta gctgggacta caggtgcccg ccaccacacc cggctaattt tttgtatttt  15480
tagtagagtt gggatttcac cgtgttagcc aggatggtct caatctcctg gcctcgtgat  15540
ccacccgcct cggcctccca aagtgctggg attacaggcg tgagccacca ctcccggcca  15600
agacaggttc ttatattgcc caggctggtc ttgaactcct ggcctcaagc aattctccca  15660
cctcagcctc ccaaagttgc aagcatgtgt cactgtgcct ggcttcttct gatttttttg  15720
gtctaaatag catctccaga tttctttttt ttttttaatt taaaaaatgt atttatttct  15780
ttatttagac acagggtctt gctatgttgc ccacactggg gtacactggc tattcacagg  15840
tgtaagcata gcccactata gtcttgaact cctggcctca agggatcctt ccacctcagc  15900
cttccaagtc tgggactaca tctggctaag catcttcaaa tttcttattt atttatttat  15960
ttatttttga gatggagtct tgctctgttg cctaggctgg agtgcagtga ctcaatctca  16020
gctcactgca acctctgcct cctgggttca agccgattct cctgccttag cctctcgagt  16080
agcagggatt acaggcgtgt gccaccacac ccagctaatt tttatatttt tattagagac  16140
agggtttcac catgttggcc aggctggtct cgaactcctg acctcaggta atctacccgc  16200
ctcggcctcc caaagtgctg ggattacagg cgtgagccac tgtgcccggc tgcatcttca  16260
```

-continued

```
aatttcttaa atactccttg gtatagtgga gcccttaatg cttttcacta atgcactgct  16320
ccttgatgtg ctgcctattc cagtagatac acagaatcag agtggtaagg gcctttgaaa  16380
ccattgattt gttctagtgg ctttcaaaaa ccatttttaa tacaattatt ttttaagcaa  16440
aatgttttat atatatatat atatggtttt tttttttttg agatggagtc ttgctctgtt  16500
gcccaggcta gagtgcagtg gtgcaatctc ggctcactgc aacctcagcc tccctggttc  16560
aagtgatttt cctgcctcag cctccccagt agcttggact acaggtgggt gccaacgcac  16620
ctggctaatt tttgcatttt tagtagagac agggtttcac catgttggcc aggctggtct  16680
taaactcctg acctcaggtg atctgcccac ctcggcctcc caaagtacta ggattataga  16740
tgtgagccac tgtgcccagc cagaaatgca ctttaaaaac caccagtcct tgcctgggca  16800
tggtggctca cacctgtaat cccagcactt tgggaggctg aggcgggtgg attacctgag  16860
gtcaggagtt cgagaccagc ctgatcaaca tgatgaaacc ctgtctctac taaaaataca  16920
aaaattagcc gggcgtggtg gcgtgtgcct gttatcccag ctactcgaga ggctaaggca  16980
ggagaatcgg cttgaaccca ggaggcagag gttgcagtga gctgagattg agtcactgca  17040
ctccagcctg ggcaacagag caagacttca tctcaaaaac aaacaaacaa agaaaaaacc  17100
cccaatagtc caaagcccta attttccccc cattatttat ttttttaatg ggcaaatttt  17160
aaaaattgta tatatattta tggtgtacaa tgggatgttt tgacatatgt atacattatg  17220
gaatgactaa atcaagataa ttaaaatgca ttacctcaca tactcaccat ttatttgtga  17280
tgagatcaaa gtctactctt ttagcaattt tcttttttct tttcttttct ttctttattt  17340
cttttttttt tttttttgag gcagaatctt gctctgtcgc ccaggctgga gtgcagtggc  17400
acaatctcgg ctcactgcaa cctccacctc tcaggttcaa gcgattatcc tgcctcagcc  17460
ttccaagtag ctgggactat aggtgtgtgc taccacaccc agctaatttt ttgtattttt  17520
agtagagatg gagtttcacc atgttggcca ggctggtctt gaactcctga cctcaggtga  17580
tccccctgct tcagcctccc aaagtgctgg gattacaggc gcgaggtgcc cagcctttta  17640
gcaatttcca atacattgtt attaactata gtcaccatgt tgtataatag atctctttaa  17700
cttattcctg ataactgaaa ttttgtatcc tttaaccaac atctatcctg ttccacccct  17760
gccctcccac cccctacccc cagcccctgg taagagcctc tactcttcac ctctatgagt  17820
tcaacttttt gaaattccac atataatcta gcgaggttat gcagtatttg tttttcagtg  17880
cctgcagata tgacattttt gggttcaact ttttgtttgt ttttgagatg gaatctcact  17940
cttgtcgccc aggctggagt gcagtggcgt gatcttggct cactgcaatc tccgcctcct  18000
gggttcaagc cattctcctg tctcagcctc ctgagtagca gggattacag gcgcctgcca  18060
ccgtgcccag ctaatttttg tatttttagt agagacgggg tttcactatg ttggccaggc  18120
tggtctctaa ctcctgacct cagacgatct gcctgcattg gcctccaaaa ctgctgggat  18180
tacaggcatg agacactgcg accggccaaa cattttttta atgcataata gatgtacata  18240
ctttcagggc acatctgata atttaatata ttcatataat ttgtacagat caagtcaatg  18300
taactggtat atccatcgcc ttaaacattt gtcttttctt tattctagga acccatttga  18360
attattcttt tctagctatt ttgaaatata caatagatta ttgtgaacta tagtcaccct  18420
actgatccat cgaacactag gtcttatttc ttcttattaa actggatttt gtactcatta  18480
atcaagctct cttcatcctc cccactctac ctggcgtctg gtaaccacca atctactctc  18540
tattatcatg aggtccactt ttttagctcc cacatatcag cgagaacatg taatattcgt  18600
```

-continued

```
cttttttgagg ttggcttatt tctcttaaca taatgacctg cagttccatg catgttgctg  18660
caggtgacag gatttccttc ttttatttta ttttatttta tttttttgag acagagtctt  18720
actctgtctc ccaggttgga gtgcagtggc gtgatcttgg ctcactgaaa cctccggctg  18780
ccaggttcaa gtaattctcc tgcctcagcc tcctgagtag ctgggactac aggcgcgtgc  18840
caccacaccc aactaatttt tttttttttt tttttttttt tttttttttt tttttttttt  18900
tttttttga gacggagtct cgctctgtcg cccaggctgg agtgcagtgg cgggatctcg  18960
gctcactgca agctccgcct cccgggttca cgccattctc ctgcctcagc ctcccaagta  19020
gctgggacta caggcgcccg ccactacgcc cggctaattt tttgtatttt tagtagagac  19080
ggggtttcac cgttttagcc gggatggtct cgatctcctg acctcgtgat ccgcccgcct  19140
cggcctccca aagtgctggg attacaggcg tgagccaccg cgcccggccc actaattttt  19200
gtatttttag tagagatggg gtttcacatg ttggcaaggc tggtctcgaa ctcctgacct  19260
caggtgatcc gcctgcctcg gcctcccaaa gtgctgggat tacaggcttg ggccaccgca  19320
ccaggccagg atttccttct ttttcaagtc tgaatagtat tccagtgtgt acatatacta  19380
ctacgttttc tttatccgtt catctgtttg agtcttcttt ttttcttagt ttagctaaag  19440
atttatttta ttttttcaaa aaactaattt ttcattttgt tgatcttctg tattttttta  19500
gtctcaattt catttatttc tgctgtgatg ttctttcttt ccttctacta attttgagtt  19560
tgatttgttc ttgcttttat agttccctca tgggcattac taggttgttt atttgaagtc  19620
tgttccttct ttccttcatt ccttccttcc tccctccctc cctccctccc ttcttccttc  19680
cttccattct ttcttttttt tttgagaggg aatctcgctc tgttgcccag gttggagtgc  19740
agtggcgcga tctcagctca ctgcaacctc cacctcccgg gttcaagcaa ttctcctgtc  19800
tcagcctccc aagtagctgg gattacaggc atgcaccacc acgcctggct aatttttttg  19860
tatttttagt agagacgggg tttcaccata ttggccaggc tggtcttgaa ctcctgactc  19920
tgcccgcctc agcctcccaa agttctggga ttacaggtgt tagccattgt gcccggccct  19980
tctttccttt cttcttcttt ctttctcagg gtctcactct gtcacctgga ctggagtgca  20040
gtggtgcaat catggctcac agcagctttg acctcctggg ctcaggcaat cctcctaccc  20100
cagcatccca agtagctggg actaaggcta ccatgcctgg ctgatttttg tattttctgt  20160
agagacaggc tttcaccatg ttgcccagtc tgctcttgaa ctcctgggct caagcaatcc  20220
acctgccttg gcctcccaaa gtgctgagat cttatttgaa atctttcaac tttttttgata  20280
taggcattac ttgaaatctt tctacttttt tgatataggc atttattgct ataaactttc  20340
ctcttagtgc tgcttctgct gtatcccata gatttttgca tgttgtattt ccattttcat  20400
ctgtttcaag atattttaaa tttttctcct aatttcttca tggacccatt ggctattcag  20460
gagcatgttg tttaatttcc atgtgtttgt gtattttcca aggttcttgt tattgatttc  20520
taattttatt ccatagtggt gagaaagata cttgttatga tgtctacttt tctgaatttg  20580
ttaagacttg ttttgtggcc taagatatag tctatgctgg agaatgttcc atgtgctatt  20640
gagcagaatg tctattctgc agcagttgag taaaatgctc tgtgaatgtc agctaggcct  20700
atttgagcta gtatatagtt taatgtttct ttattatttt ctgtctggat gatctgtttt  20760
actgagagtg aggtgtggtg ttagagtccc ctactactat tgcattacag tatatctctt  20820
cttttagatc tattaatgtt tgctttatat actttggagc tccaatgttg agtgcaaaga  20880
tacttatatc ttcttgctga attgacccct ttatcattat atagtaacct tctttgcctc  20940
tttgacagcc ttgattcaca gtctgtttta tctgatgtaa gtatagctac tcctgttctt  21000
```

```
ttttggtttc cagttgcttg gaatgtcttt tttccacccc ttaacttcca gtatttttat  21060
aagtaaagta ggtttcttgt aggcagcata taatttggtc ccatttttgt atccattcag  21120
ccactctatt cctttttttt gggggggggtt cccaagtttt attcaagaac tcataccaaa  21180
tattccagat aaataaattt ttatcttcac cttcctcctc ttctttttcc aggttaatct  21240
ggaattaacg tcattcataa taactctttt tgctgttagc aactacacac aacaaatcac  21300
atagattatt cttcaaatat tttttggtga gatatttcaa atacctttttg gaaaaaggta  21360
cctcagaagt cacagtgatc ttgctgttgc tcctttcgat ggttataatg ctccaccaag  21420
attcccagct tttccattca ctttaatcct ctcttgcaaa aactgctcaa aattggcagc  21480
atctatgatt ccattttcta caaggtgggt acagtcaaga gtgaacatca taacctgctt  21540
ctttttttgc ctctctttgc cacaagcttt ttcacagcac tatgcctctt aattggagaa  21600
ttgagtccat ttacatttag tgttattatt gatacataaa gacttaacat ttttttaaat  21660
tgatacataa ttgatgtagc tattttgggg cgttcatgtg ataatttaat acattcatat  21720
aatttgtaaa gattaaatta gtgtaattgg gatacctatc accttcaata tttgtctttt  21780
cttttctttt tttttctgtg agatggagtt ttgctttttt tgcccaggct ggagtgcaat  21840
ggcgcaatct cggctcactg caacctccac ctcccgggtt caagcaattc tcctgcctca  21900
gcctcccgag tagctgggat tacaggcatg caccaccatg ctcagctaat tttgtatttt  21960
tagtagagac ggggttttac catgttggtc aggctggtct cgaactcctg acctcaggtg  22020
atccactcgc cctggcctac caaagtgctg ggattatagg catgagccac cacacctggc  22080
cctgtctttt ctttatgttg gaaacattca aattattctc ttctagctat tttgaaatat  22140
acaatatatt attgtaaact agtcacttta ctgatatatc aaacactagg tcttatttct  22200
ttcatcaaac cctatatata tatatatata tatatatata tatttttttt ttttttttg  22260
agacggagtc tcgctctgtc tcgctctgtc gcccaggcta gagtgcagtg gcacaatctc  22320
ggcccactgc aagctccgcc tcccgggttc atgccattct cctgcctcag cgccccgagt  22380
agctgggact acaggtgcct gccaccatgc ccggctaatt ttttgtattt ttagtagaga  22440
cggggtttta ccatgttagc caggatggtc tcaatctcct gaccttgtga tccacccacc  22500
tcggcctccc aaagtgctgg gattacaggc ttgagccacc gtgcccggcc aaaccctata  22560
tttataacca ttaatcaact tctctttatc tccccccattc tgtacccttt ctggcctttg  22620
gtaactatca atatactctc tatcttaatg agttccactt tttttagcttt ccacatatca  22680
gtgagaacat atgatatttg tctttctgtg tttgccttat ttctcttaac atgacctgca  22740
gttccatgca tcttgctgca aatgacagga tttccttctg ttttaaaatc tgaatagtat  22800
tccattgtgt atatatgcca cgttttcctc atccattcat ccattgctgg atgcttaggt  22860
tgattccata tcttggttat tgtgattaat gctgcagtca acattaggag tgcagatatt  22920
tccctgacat actgatttca tttcattccc ttcccttccc ctgcctgtct gcctgccttc  22980
cttccttcct tccttccttc cttcctttct tccttccttc cttcccttcc tccctccacc  23040
ccccccgccc ctttcagatg gaatctggct ctgtcgccca ggctggagtg cagtggcgca  23100
atctcagctc actacaacct ccgcctcctg ggttcaagca attcttctgc ctcagcctcc  23160
cgagtagctg ggattacggg catgtgccgc catacccagc taattttttt gtatttttag  23220
tagaggcagg gttttaccat attggccagg ctggtctcga actcctgacc tcatgatcca  23280
cctgcctcag cctcccaaag tgctgggatt acataggtgt gagccaccgt acacagccag  23340
```

-continued

```
tttcattttc ttttcttttt tttttttttt tgagacggag tctcgctctg ttgcccaggc  23400
tggagtgctg gagtgcagtg gcacgatctc ggctcactgc aagctccacc tcccgggttc  23460
acaccattct cctgcctcag cctcccaagt agctgggaca acaggcgcct gccactatgt  23520
ccggctaatt ttttgtattt ttttagtaga gatggggttt cactgtgtta gccaggatgg  23580
tctcgatctc ctgaccttgt gatcggccca cctcggcctc ccagagtgct gggattacag  23640
gtgtgagcca ccgcgcctgg cccattttct ttagatatat acccaagtag ggggattgct  23700
gggtcatata gtagttctat ttttaatttt ttgaggaatc tccatactgt ttcccataat  23760
ggctgtacta atttaaattc ccaccaacag tgtgtaagga ttagtgctgg tgaggatgtg  23820
gagaaaacga tacttctggg cattttttct tctattgaga ctaaagttgc aactcttagt  23880
attttttttt atactaccct ttaggaaggt gaaattgttg aagtggatga agaaacagca  23940
gctatcttga agaattcaag atttgctcaa gattttctga tcagaccaat tggagagaag  24000
ttgccaacat ctggaggctg ttctgctttg gagttaaagg ttagtttggc tttcactacc  24060
tgagagaact attttattta tttatttttg agatggagtc tctctctgtc acccagactg  24120
gagtgcagtg gtgtgatctt ggctcactgc aacctccgcc tcctgggttc aagcaattct  24180
ccctgcctca gcctcccgat tagctaagat tacaggcacc caccaccacg cccggctaat  24240
ttttgtgttt tttagtagag atggggtttc gccatgttgg ccaggctggt cttgaactcc  24300
tgacctcagg taacccacct gcctcagtct cccaaagtgc tgggattaca ggcgtgagcc  24360
actgtgcccg gccagtatgc atggtctctt gaggcgcact tctcttgctg gtcaaatgtt  24420
gttagacggt tatataccag ttaaacgcca ccattttgcc tcttaatgtg catgcttgag  24480
cccacttgcc caactcccga gatcttatcg ggaagctgct gatcaccagt ttcaggtgtt  24540
tctgtttatt gggagacttc ctttccctgg tactgtctgt gactaattat gattttcgag  24600
agacagttaa caaccacctg atcatcacct aatgatcgcc tgacattcct ggtggagtcg  24660
gcgcggggag ccctctcctg ccctgctcac gcctgactag ctattatacc tgctttaaca  24720
agttctccaa aattcagaga cctttcgtga gtattctgat tttataataa aatagttatt  24780
tgcataagtt tagtaagagt cttttctctc aaaacaggac aattggagac acttggttat  24840
tttaccaaag ctttgactgg aataacattt gtaggtaaag ttccagcaaa gccaacttga  24900
aaagagccta tctggccaaa ctcttgctgg acttcatgca aatgatcagg caaagtttaa  24960
taagcctaaa atttattttg cacataaatt ggccttacta taatttgtct ttagtataaa  25020
aggaggagct gggtgcagaa gttcacactc ataatcccag cactttggga ggctgagaca  25080
ggcagatcac ttgaggccag gagtttgaca ccagcctggg taacatgttg aaaccctgtc  25140
tctaccaaaa atacaaaaaa attatctggg tatggtggtg catgctggta gttccagtta  25200
ctcaagaggc tgagatggga ggattgcttg agcccaggga ggtggagggc aatgagccaa  25260
gactgcacca ctgcactcca gcctgggcaa cagagtgaga ctctgtctca aaaaaaaaaa  25320
aaaaaaaaaa aaaaagaaag aaggctagag agagaaatgg tttcaaagga aaactataac  25380
acttgttact agatttccag cctggacttt tgtttttgag tgcatattga atcattaatt  25440
atttcttggc tacaataacc ctctaaagat aaaccaggtt ataatttttc ttcatgtttt  25500
tagtttgtgc cctaagtgga ataggttcct tattctgttc tgacacacga atactctttt  25560
gactgtcata ttattaatgt tatttatagc tccttgtttt acttccaaag aaaccagaat  25620
catgatattc taaggttaga gaatcccccg tttggaatcc cactggtcct aatctgcttt  25680
tcactgcaaa ttccgtgctg ctaaaattat ataagcactc ttctctaggc ccagggacct  25740
```

```
atcacacaaa aggtaggtgt gtgagactgt aagggccagt tttgagagaa ttatttcaga  25800
ctctccaaat caaaaatggg cacacagatg cataaacagc tggtaaaata agggactctg  25860
cctcctgggt tattatgtgt gtggcacctt ttcatccatc ccaatcataa agaatttcct  25920
gcttctcgta gaatgaaaag aaaattatta ctgagaggat ataaaggtac ctcatgtcaa  25980
agcctcctag gtttaatact ctgagttatg agatttatgc agataacata tatatttttt  26040
aaaattttag aacaggccag gcacagtggc tcaagcctgt aatcctagca ctttgggagg  26100
ccaaggtggg cagattgcct gagctcagga gttcaagacc agcctgggca acatggtgac  26160
accccatctc tactaaaata caaaaaataa attagatggg catggtggcg tgcgcctgta  26220
gtcccagcta cttgggaggc tgaggcagga gaattgcttg agcccgggag gcggaggttg  26280
caatgagacg agattgagat ggcgccactg cactccagcc tggcaacaga gtgagactct  26340
gtctcaaaat aaataaataa ataaataaat aaataaataa ataaataaat aattttagaa  26400
caaattactg aaagaccaca aaaaaaaaaa ctgtagcaca acggaagtct ctaaattcct  26460
tagcttaaaa ggttttaaca gtgcttatgt tttgtatagc taattgctgt aagtctgtaa  26520
ctaaaaccaa gattacagta gcacaatgca tagaagttaa agataagtca attttttaac  26580
ctcacctttg gctttttgtt tgttggcttt tatattaaga aattttaagg gtttattaat  26640
gcctatccac atccattccc atctggccta gaactttctt ttttttggtg ggggaggggg  26700
acggagtctt cctctgtcac ccaggctggg gtgcagtggc gtgatctcat ctcactgcaa  26760
cctccgcctc acaggttcaa gtgattctcc tgcctcagcc tcctgagtag ctgtaattac  26820
aggcatgtgc caccatgcct ggctaatttt tttttctttt tttttttttt ttccgagatg  26880
gagtcttgct ctgttgccca ggctggagtg cagtggtgcg acctcggctc actgcaacct  26940
ctgcctccca agttcaagcg attcttctgc ctcagcctcc agagtagatg ggactacagg  27000
tgcgtgccac catgcctggc taatttttat tttatttttt tagtagagat ggggtttcat  27060
catattggcc aggctggtct cgaactcctt acctcatgat ccacccacct tggcctccca  27120
aagtgctggg attataggca tgagccactg tgcccagccc taattcgtat ttttagtaga  27180
gacagggttt caccatgttg gtcaggctgg tctcaaactg ctgatcttag gtgaccaacc  27240
tgtctcggcc tcccaaagtg ctgagattac aggggtgaac caccatgcct ggtctggcct  27300
agaactttca aattcgctat gtgtcttttg gctctaagcc ccttgaccat aggggtccca  27360
ccaaggcaca agatggaccc agggaaggca gctgtgccac cccagcaaca cagtgagata  27420
aaataaaagt ttggtgacca ttgatgttgc ctctgacaaa tctaggccag aatgcggaga  27480
aagtaaatca aaaataaaat tctaggccgg gcgcggtggc tcacacctgt aatcccagca  27540
ctttgggagg ccgaggcggg tggatcacaa ggtcaggagt tcgagaccag cctggccaac  27600
atagtgaaac cccgtctcta ctaaaaataa aaaatcagcc aggcgtgggg gcaggcacct  27660
gtagtcccag ctacttggga ggctgaggca ggagaattcc ttgaacctgg gaggtggagg  27720
ttgcagtgag ccgagatcat gccactgcac tctaacctgg gcgacagagc gagactccat  27780
ctcaaaaaat aaaaaaaaat aaaaaaataa aaaaataaaa taaaattata aaccctcaac  27840
catctgaacg gacccctcct gtcgggcaaa ggcattgcaa agttatccta aaaaactagt  27900
tcaggtcacg aagggaagga gaagtttgga catgcctcat tattccctcc tccctttgg   27960
aattcagaca ctgctgacca gcattaccat taaaacagat cttaagactg atagaacaga  28020
ctctttaaat ctggtaagaa acatttacaa tctattctct ctgtagcctg ctgcctagag  28080
```

-continued

```
gcttcatctg catgataaaa ccttggtctc cacaatctct tatcataacc tagacactcc  28140
cttctattga tcccaggtct ttggattata actcaaccaa ttgccaatca caaaatcttt  28200
gaatctgcct gtgacctgga aatccccact tccagttgtc ccacgtttct ggtctgaacc  28260
aatgtacata ttatatgtat tgattgatgt cttatgtctc tctaaaatgt ataaaaccaa  28320
gttatagggt gaccactttg ggcacatgtt tgcagatctc ctgagggctg tgtcacaggc  28380
cattggtcac ttatttggct cagaataaat ctttttaagt attttagagt ttgacccttt  28440
ttgttgacaa tgtttaacat cctacagtta tgacacccta atttgaattt atacagctta  28500
acttcaataa catactaaaa ttctgctcct ttaaagcttg ttctcaacta ttttagttct  28560
tttttttttt tttccattga cagagtttca ctctatcacc caggctggag tgcagtggca  28620
cgatcttggc tcactgcagc ctctgcctcc tgggttcaag tgattctcct gccccagcct  28680
cacaagtagc tgggattaca ggtgcgccag ccaccatgcc tggctaattt tttgtatttt  28740
tagtagaggc ggggtctcat catgttggcc agcctggtct cgaactcctg acatcagatg  28800
atccaccagc ctcggcctcc caaagtgctg ggattacagg tgtgaactac cacgcccggg  28860
tctttctagt tcttgatatc acaaaattat gtctttattc attttgtgcc cccaaaacgt  28920
aaactaataa ttattttaaa tgcattggtc tcttaaatca tgtggaaaac aaaaagtaga  28980
gttacaaacc attgttacaa taatactagc tttgccgggt gtggtggctt acgccaccag  29040
gtgatccacc cacctaggtt gcccagcctg ggcaacaaga gcacaactcc atctcaaaaa  29100
aacaaaaaca aataaacaaa aaaccccaat aataccagct tttttttttt tttgagacag  29160
agcttcgctc ttgttgccca ggctagagtg caatggtgcg gtcttggctc accgcaacct  29220
ccgcctcctg ggttcaagcg gttctcctgc ctcagcttcc caagtagctg ggattacagg  29280
tgcgcaccat cacagccggc taatttttgt atttttagta gagacggggt tttaccatgt  29340
tggtcaagct ggtctcaaac tcctgacctc aggtaatcca cctgccttgg cctcccaaag  29400
tgctgggatt acaggcatga gccaccgtgc ccggccaatc ccagcacttt gggaggctga  29460
ggctggcaga ccacttgagg tcaggaggtc aagaccagcc tggccaacat gctgaaaccg  29520
tgtctgtact aaaaatacaa aaattagctg ggcacggtgg caaatgccta taatcccagt  29580
tacttggggg gctgaggcag gaggatcgtt ttgagcccgg gatgtggagg ctgtagtgag  29640
ccgtgatcac aacactgtac cccagcctgg gcgacagagc aagaccctgc ctcaaaaaaa  29700
aaaaaaaaaa agcacaaagc tttttgagaa atcactttca aaaatggtac atttgtagtt  29760
ggggaaggtt aatcgaacct aaaatataag aatcctggac cccaaaacct ggagccagta  29820
ttaccagcat gaatctaacc caagctcagt atacaagcca cctgtagagc taaagagtga  29880
tttactaggc cgggcacggt ggcttacgcc tgtaatccca gcactttggg agccgaggcg  29940
ggtggatcac gaggtcagga gttcaagacc agcctggcca agatggtgaa accccgtctc  30000
tactaaaaat acaaaaaaaa ttagccgggc gtggtggcat gcgcctgtaa tcccagctac  30060
tccagaggct gaggcagaga attgcttaaa cctggagggg cggaggttgc agtgagccga  30120
gatcgcgcca ctgcactcca gctggggtga cagagtgaga ctccatctca aaaaaaaaaa  30180
aaaagagtga tttactttct ttgctttatt aaattcttca gcactctgct attctgactc  30240
ttctgttgtt cgaagaaggt gatactttgg aaagtagaca gatttggctt ttgagtattc  30300
aatccattaa acatttcaaa aatatgtcac tgatattttg aaactcctga gagttcattg  30360
ataaggaaag ctgctggtga gaatcaatat ttattttaaa aggcttttat cattctaatt  30420
cttctaaaac ctggtttcct aaatactgat tataaaagct atcagaaggc gtggtggctc  30480
```

-continued

```
acgcctgtaa tcccagcact ttggggaggc cgaggcgggt ggatcacgag gtcaggagat  30540
cgagaccatc ctggctaaca cggtgaaacc ccgtctctac taaaaataca aaaaattagc  30600
cgggcgtggt ggcgggtgcc tgtagtccca gctactcggg aggctgaggc aggagaatgg  30660
cgtgaacccg ggaggcggag cttgcagtga gcagagatca tgccactgca ctccagcctg  30720
ggcgacagag tgaggctccg tctcaagaaa aaaaaaaaat gctatcagaa gataatggtt  30780
acaagtaaag agggtctttc ctcgagctac agtattttca gtgtactctg gctttttttt  30840
tttcctttga gacagagtct cgctctgtca cccaggctgg agtgcagtgg cacgatcttg  30900
gcttactcct ccgcctcctg ggttcaaaca attctcctgc ctcagcttcc cgagtagctg  30960
ggactacagg cacacgccac cacgcccggc tcattttttg tattttaata gagacggggt  31020
ttcaccgggt tgcccaggct ggtggtgaac tcctgagctc aggcaatccg cccgcctcgg  31080
cctcccaaag tgctgggatg acaggtgtga gccactgtgc ccagccactc tggctatttt  31140
ttttaaaaaa ggagttaaat gagtttgctt ctgcagatga ccattttctt tctgcgtagc  31200
tgtccttgtt ctccctccca gtgtgcgtgc aacacatgta caggaggttc ttgaccttag  31260
atataaattg taaaattcca catatttgaa ctggtttatc ccaacataag gtctcctttc  31320
tgctttattt cagcctgcag atgtgccaat gtctttaggt cagtttcaag tttttgaaat  31380
gggaataagt gacactgaag gaagatttta ataaatgaaa cagttgtgtg acctaggaat  31440
ataaccttgt gctcttaggg aaggacattc ttatcttttt tttttttttc ttaacggaag  31500
acctttatga taaacgctgg agtacagaca gtacacgcag ctggcatgca gggtattgca  31560
tatacttaac atcttgagag tccttctgct ttttcttcat cttcttttta atcctgatat  31620
gcaaaatgta ttttgccatt aaaacaattg tactattaaa acactgcagc atctggctgg  31680
gcgtggtggc tcacacctgt aatcccagca ttttgggagg ctgaggcggg tggatcactt  31740
gaggtcagga gttcaacagc agcctgtcta acatggtgaa accccctctc tactaaaaat  31800
acaaaaatta gctgggtgtg gtggcgggtg cctgtaatcc cagctttttg gaagactgag  31860
gcaggaggat cacctgggag gcagaggttg cagtgagcca agatcgtgcc actgcactcc  31920
agcctcggcg acaaagggag actccctctc aaaaacaaaa aaacaacaaa acactgcagc  31980
atctgaaatg atgcaaacag gattagggct atggactgtc ttaatagtaa tggtagtaat  32040
agcattaaca accatagcag taatatagag gaattaactt ttattgaata gttaatatgt  32100
ttaaggcacc ctgtcattta gtcctcacaa tcacccctat tatcttcatt tgacagatgg  32160
agagactgag gctctgaaag attcatttac aaatccaaag tcatacagct agaaagtggt  32220
gaatttgcac ccacatctga ttctggagct ggcactctaa accagtgtgc tgctccatct  32280
ctccatagtt gtacttctca tagaatcaca ggatgttggt gcaggaaagg actgcttata  32340
tctgggtacc ccacctttca tttccttcaa gtcttgagat ctttttgaac tagaagcatg  32400
catttagaag tgatattgat atcaccatct cctgttggta gatagatcat tgagtggaaa  32460
gaagagggtt caagggattc tcccacctca gcctcatagt agccaccacg cccaactaat  32520
ttttatattt tcagtagaga cggggtttca tcatgttggc caggctggtc tcgaactcct  32580
gacctcaggt gatccactgc cttggcctcc cagagtgctg ggattactcc cagagtacat  32640
gagccaccgc accaggccag ggcaaaccct ttcaagcagg agttccagta tactgagaga  32700
tggaaatgca attgatgtga agtcctagca gtagcaacca gcagagctgg ccttcttcca  32760
ggcttggaga tcctctgcca gatgctcatc ttaccagatg caggcagacc tcttcatttc  32820
```

-continued

```
agaaaggtag acactgaggg acagagagac caaggccagc aggaagtcag tcactttagt  32880

aaagggtcca ccagtctatc agtttcatga atgtagagtc tgtgcctgcc ttgtacaccc  32940

ctctatttgc agtgaccaga ataagtagta ggactgtaaa tttatgttat aatgaattca  33000

ttaccattat ttaaagtggc atgttcatgc tttttttttt ttttttgaga tggagtctcg  33060

ctctgtcacc caggttggag tgcagtggtg tgatctcagc tcactgcaac ctccacctcc  33120

taggttcaag tgattctctt gcctcagcct cccgagtagc tgagactaca gacgtgccac  33180

cacacccagc taatttttttg tatttttagt agagatggga ttttgccata ttgcccaggc  33240

ttgtctcaaa ctcctggcct caggtgatcc attggcctcg gcctctcaaa gtgctgggat  33300

tacaggcgtg agccaccgtg cccagaccct gtgctcttga tttcctatct ttgtacttgg  33360

cttttctctg gccccactgg tactattgtt agaggtatct catttggagg tgaaaggagg  33420

ggaaataaat acagcagtct tgtcttttaa ataaatacag cagtcttatg ttactctact  33480

ctgagatctg tctggccatt gttggcaatt tcatctgagc atcagcaatt gctagtgaca  33540

gccctacatc tgggactcac tttcctgttt ggtataaatg tttctggaga ttagaataag  33600

ggaagagaag tcgttttagc atttccgtat ctcagttcca aagaggttta aaaggcacgt  33660

gcaaatgaca accccacaaa acaaaatcaa ctgagcaaaa atcaatgctc tgcccaagag  33720

ggaccatctt taagaagctt taagtgaagt ttaccttgaa agttgtaatt agaagcttca  33780

ggaagcaagt gcctttatgg cagaatgact gatgttactc ccaggatctc atggaattgt  33840

aaaattttat ctctgttctg tgtaagtcaa cctaaatcaa acagaaatat tagtgtttgg  33900

gtacatcaaa acacctttaa cttgtccttt cattttggtt tgccttttga caggatataa  33960

tcacagatcc atttaagctt gcagaagagt ctgacagtat gaagtccaga tgtgtccctg  34020

atgctgctgg aggctgctgt ggcacaaaga aaagctgcta aatctatagc caaccagggg  34080

accacagtag tgggcaagag tgatctgcat gttttttaac ctgcttttcc ccatagcaca  34140

gaccataaga aacaacaaat ggggccgggc acagtggctc atgcctataa tcccagcact  34200

ttgggaggcc gaggcaggca gatcacctga ggtcaggagt ttgataccag cctggccaac  34260

atggtgaaat cctgtctcta ccaaaaatac aaaaaaaatt agctgggcat ggtggtgcac  34320

acctatagtc tcagctactc gggaggctga ggcaggagaa ttgcttgaac ccaggaagta  34380

gaggctgcag tgagtaagca tcacgccact gtactccagc ctgggcaaca gagcaagact  34440

ctgtctcaaa agcaaaaaaa aaaaaaaaaa aagaaagaaa gaaaaagaaa acaacaaatg  34500
```

<210> SEQ ID NO 2
<211> LENGTH: 34500
<212> TYPE: DNA
<213> ORGANISM: Homo Sapiens

<400> SEQUENCE: 2

```
ttcccatccc ctcttttaaa gatacataca atcaaaaaat agaatttttt taatcgaaaa     60

cactccgacc cgcaccaccg agtgcggaca ttagggtcgt gaaaccctcc ggctccgccc    120

gtctagtgct ccagacctct aactctggca ggaccgattg tgtcactttg gggcagagat    180

gatttttatg ttttttaatc gacccgcacc accgcccgcg gacatcaggg tcgataagcc    240

ctccactccg tcatcttacc gtacttgggc cctccgcctc gaacgtcact cgactctagg    300

acggtgacgt gaggtcggac ccactgtctc gctctgagac agagtttttt tattttttcg    360

aaaacggtta taaattttat actgaactac actctcagaa ttaaagaaga tgcgtcatat    420

gtctatatat cgtaaggaca gtaaatcgtc cccactatca ttttgttttt ttgtttttttg    480
```

-continued

```
gggtgttttg gacaccactc cgtgactggt tagtcttact aactaccagt gtcagaccag    540
gttttaatcg gggtgtggt  ctgtggtacc tccttttcac tctcattgag ttaaattcaa    600
ctgtcaccaa acaaaataac gtcaaataga cacacactta tccatctaaa ttcctaacaa    660
ccggtccaca ccaccgagtg tggaccttag ggtcgtgaaa atcctccgtc tccgtccgcc    720
tagtgaactc tagtcctcaa gctctgtcgg accggttgta ccactttggg acagagatga    780
tttttatgtt taatcggtcc gtaccatcac gtacggacat taaggtcgat gaaccctccg    840
actccgtcct cttagcgaac ttggccccctc cgtctccaac gtcactcggc tctaacgcgg    900
taacgcgagg tcgaacccgt tgttctcgct ttgagacaga gttttttttt tttttttttt    960
ttcctaacag tttactaaga acattcattt ggtatttaat ttctattgtt ttgttcgtgt   1020
tctcttttta ctatgtcggg aaaggaactg gagagtgatt agacgggaaa attctatttc   1080
tatagtaaaa ttgatactct tccattgacg aaaagatttc ctcgagtaaa atacttctat   1140
tataaaactt ttgattataa atcctcacaa aagtggtaag atactaacgg gtttttgatt   1200
cactatgaat atttttgtga ttcaaaatat gtatatgatc aacctttata aggttcgaca   1260
tctttataag gttgttccta ataaaggtac cccaattaaa caatttttat attttctgtg   1320
gtggaaagat aattaaacat tgttgattaa ctgtagtctc ttctactttt aaatgatcga   1380
cctatagttg gtctaaaaac ataataaccg ttgactctaa ctttttactt actttctcag   1440
atgaagtagg taaatctata ggaaagtgaa cctagaggga caaaggaatg acaggattac   1500
ttatctttac tagcaatgtt cgacccgtac caccgaacgt ggacatcagg gtcgatgacc   1560
cctccgactc ctccctccta ccgaactccg gtctcaactt cctaggtctc tactaacgcg   1620
tcactgcgat tcgaacccgg tgtctcaact ctgggacaga gatttttaaa aaaaaattaa   1680
atttaatatt tttctcttta cgaacaatgt tggtgtttcc ctttgttcta tatgtgtata   1740
ttaacacctt catttttatt tattaaattt ttatgaaaac ccacgagcga agccgtcgtg   1800
tatatcaacc ttactatctc ttctaaacgt accggggacg cgttctactg tatgtttaag   1860
cacttcacaa ggtataaatt tttttgtttt ttatgaaaac ccggaccgtg acaccgagta   1920
cggacattag gtttgtgaaa ccctccgact ccgcccgcct aacgaacttg ggtcctcaac   1980
ctctggtcgg acctgttgta ccactttagg gcagagatat ttttttatgt ttttaattgg   2040
tccacaccac cacgtgcgga cattaggttc catgaaccct ccgactccgc cctcctagcg   2100
aactcggtcc tccaacccgg acccattgtc tctggcagag tttttttaaa tttttaattt   2160
tttttttgaa agacgttcta cttcactgtt atggaccttt tatgtacact gaactggttt   2220
ttaatgatat ccacttttat ttaaatcgtt tcaacgaaag gatttatgtt gggttttatc   2280
tgacccttgt cgatgtatga caattaccaa gggagataca ctgtaagatc ttttccgtct   2340
tgatatccct cccttttgta gacaccaacg ggtcctcgat ccccaccctt ctcccttaaa   2400
tgatgtttct ccgtgcttct ttgaacaccc ggtctcgata aaaccagagg caaaaccact   2460
acatatatgc aaacggtctc aagtgtcttg acgtgtgact tctttctacc taaagtgcct   2520
tacacttaat atagagttgt ttgaactgaa gttttttgtc tagctctttt ctactaagat   2580
aagggttttt ccccctcccc ccttctagta atatatccac tcacaagtaa atttagtctc   2640
atgctctaaa taggcacttt tagcgtcacc tcgcttgttc cccctacgac tatggctgga   2700
ggaccaacct ttcggacatc tcgtcgcgcc tactgtcacc ttgtcgccca gtccgccacc   2760
cgcggactcg ctccccgatc tcgccctacc cgcccgcctc gttcggacgg tcggacccgc   2820
```

-continued

```
cccggagccg tgtcctcgac cgacgccctc gggcggcagg actcagcgtc cggctcctct   2880
gtcactcacg cgcgggactc agcgtccggc tcctctgtca ctcacgcgcg ggactcagcg   2940
tccggctcct ctgtcactca cgcgcgggac ccgcggggcg gggtcggggg tcggggaagg   3000
gacccggggg cgttccgccc ttgcgctcgc ggaggggggct cgacacagag ctctggaaac   3060
aggaggggag tggggagccg ggcgacggac gggaaatgac cgggggaggg agtacgggca   3120
gggagtcgtg ggagaggaaa gttgattgaa agggcgaggg ctgtcaccga cgtgaagcac   3180
tgcgactcta tgtcttcctg cacgtccact ctcgacatcc cggaccttac cgggttcacc   3240
tcggatccga ttaccttcag accggaccgg gcgtgggaca gggggccctg aggacctcag   3300
ccccatcccg tcccagatcc gaagctggaa aggtcccttg actccagccg gttcacctcc   3360
acctccacca ctgcctcggg agcgcgacgt cagtgtcgag aagagggaga gatggggagt   3420
gaggtgacac cctgcgaccc agtctggatg atgcccgtcc acgacttctc tagccgtctg   3480
gaggtctggt tgccgacaca gtggtgtcgg tccggccagg ggttcgtgta ggcccttcgg   3540
aacgttttac atgtgcttct tcatcgggat tccatctcac gggacacgac aggggtcctt   3600
ctggggtttg tcgtcaaaag ggttttctat tactacgtcc agtgatccct taattgggca   3660
tcggtggttg ggtagtcgaa cggaacagat aacattttta ggatttagag tcgtgggtag   3720
tagaatgacg agattcttgg aggctactca gacccgcgcg gtcactcgga catcagggtt   3780
cacgaaccct ccgactccgt ctcctagcgc actcgggtct tcaatgtccg acatcacacg   3840
ctaggcccta cacttatcgg tgacgtgagg tcgaaccagt tgtatcggtc tacgtagaga   3900
ttttatttac gcatgaaatt tttttaacgg atttttttttc ttggaggtcg cacttgtgag   3960
acatcaggga tgggtacgag tgtcttatgt cagtgtgagt gacctagacg gtaagttcta   4020
tacgcgtcaa gtcgtgggtg attagttgga accgggaaaa ctgggaaggg aaggagtgag   4080
gtagtcgtga cggacgggtc ggccgtcagt ggttaaacct tccagaaggg aaaagaaaaa   4140
ggaagggttg ggacgcgtag gtcgtggtgc gacgacaggg tggatgacgt acctcggaag   4200
agattaggaa ctcgccggag aaggggtttg acggtgtcgt gagacagtga gccagacagg   4260
catttagtgc ccttcacaaa agacacgtgc tacaaaatag agcggagagt ttatgtggat   4320
gcgccgcccc tcgccaccga gtgcaggcag tagggtcttg aaccctccgg ttccgtccat   4380
ctagtgaact ccagtcttca agttctggct ggaccagttg tatcactttg ggacagagat   4440
gacttttatg tttttaatcg acccacatca ccccgtgcgg acatcagggt cgatgaaccc   4500
tccgactccc tcctcttagt gaacttgcac cttccgcctc cagcgtcact cgcctctaac   4560
acggtgacgt gaggtcggac ccgttgtctc tttttgagtc agttttgttt tgttttgttt   4620
tttttccggc ccccaccacc gaatacagac attagggtcg tgaaaccctc cggctccgcc   4680
ctcctagtgc tccggtcctc tagctctggt aggaccgata gtaccacttt ggggcagaga   4740
tgatttttat gtttttataa taggcccaca ccgccgtgcg cggacatcaa ggccgacgac   4800
ccctccgact ccgtcctctt gccgcacttg ggccctccgc ctcgaacgtc actcgactca   4860
agctcggtga cgtgaggtcg gacccactgt cccgttctga ggcagagttt tttttttttt   4920
tttttttttt ttttttttta atcggtcctc accaccgtcc gcgagcatca ggatcgatga   4980
gccctccgac tccatcctct taccacagtt gggccctccg cctcgaacgc cactcgactc   5040
tagcgcggtg acgtgaggtc ggacccgctg tctcgctctg aggcagagtt tgttttgttt   5100
tgttttgttt tgttttgttt agttttgttt tttgcggata ccctgtcttt ggaatgtaaa   5160
aaaggagtta ttgatcgcgt caggacccgg acttaatctt cgagtcgatt actaatttac   5220
```

-continued

```
ataaataagt tgtgtaataa aataaaataa ataaataaaa actctgcctc agagtgagac   5280
agggaatccg acctcacgtc accgcggtag agacgagtga cgttggagac ggaggaccca   5340
agttcggtaa gaggacggag tcggagggct cctcgaccct aatgtccatg gacgatggca   5400
cgggtcgact aaaaaaccat aaaaatcatc tctgtcccaa agtgatacaa ccggtccgac   5460
cagaggttga ggaacggagt tcgctaggcg gacggaactg gagggtttca cgacactaat   5520
atccgcactc ggtggcgcgg gtcggacttg tgtaataaaa tctaccgaat acttcagaat   5580
cacggatcgt gtacgggttg ttatgacacc atttcgtcta tgtcagggtc ggaagtaccc   5640
acaggtcaag tcacctctga tttgtagtct tcatactcac ttactacgtt ctttcttcct   5700
tccttccttc cttgcctccc tccctccctc ctcccttcat acatattcta aatcaccaaa   5760
gtacagaatg tcagaggtcc ctttttttata cacaaaaggt aaagggtcta taataccgac   5820
accagaccac tagggactcg tagatctttt gacgacctaa aacctagacc catcaccttc   5880
accgtctcta acgatacatg aatcggtcga ccaaccactt tttcctgtgc actgacctta   5940
tctgtactgg tttccggtcc actccgtact aaaccttctg ttcctctttt tctaagagtt   6000
ttcgtaataa actttttatt tcaacaaaag aagcaccgag aagttcctat taaattcttt   6060
cgaagatcaa tcgttacgag taaacacggt gatcacgaag gacagaacct ttgactattg   6120
aacttgttaa tccccaagaa gacccgcttg tgttctcagc ctccaaacga gactatactt   6180
atagcactgc tatctcacct gaaactagaa agggaagaac gacggtagat aggactttct   6240
aaaacaataa cttactcctc aaataagttc ggtttgacgt gcccgtcgtc cctcaaatac   6300
agggtccaac atcatatagg atgcacaggt gtccttagaa catacaaata ggttttatta   6360
gatccccttc atataagaca atcactatcc tttaaaaatc ctttttcaac acataaaaaa   6420
agttttacaa tagttttgat ataaaaagaa tgaaatccac cttcaccgac ttttcataga   6480
actgatagtg tacctttttta taccgaaggt ccgtagatta cactgaaaat aagtaccgat   6540
gtaactcttc aaccctctcc gaccttagtt cttactctcg gtactataac aacacatcca   6600
gatataagaa tgacaatact gatatcgggt aaaagaaata ataataataa taataataac   6660
tctacctgag agcgagacag tgggtccggt ctcacgtcac cgggttacag tcgagtgcta   6720
ttggagacgg agggcccaag ttgactaaga gaacggagtc ggagagttca tcgaccctaa   6780
tatccgtgtg cgatggtgta ggtcgattaa aaaatttaga agaaaatcat ctctgtccca   6840
aagtggtaca accggtccga ccagagtttg aggactagag tccactaggt gggcgaaggt   6900
ggagggtttc acgaccctaa tgtccacact ccgtgacacg agtcgggagt aaaggaaaac   6960
ttgtgtctct acagtgataa tgacaaacga cttaactgag agtaaatccc acaatttgat   7020
ttgaatcgta ccgaatgatt accctctctc gaccaaactc gacgacctcg agtggtcgtc   7080
gtcttgtgtg gtctggttct cccttgaatg aactttgaat tggtgtttgg ttacttgggt   7140
tttctggtcg tcctggtgat tcaaacgagg atgttatgta cgactggaca tagaaagtat   7200
tataaaagta ccatttaata tcctaagata aaggaaaaaa gggagttcaa caataacagt   7260
ttagtacggg ttcactgtcg acggaaactc cttgtatcgg acaaatgcac ttcgtattct   7320
ttacggaaca cggccggtcc acgccaccga gtgcggatat tagggtcgta aaaccctccg   7380
gctccgtcca cctagtgctc cagtccttaa ggtctggtcg aacttgttgt accgctttgg   7440
ggcagagatg atttttatgt ttttaatcga cccacaccac cgtgtacgga cattagggtc   7500
gataaatcct ccgactccgt cctcttagtg aacttgggcc ctccgcctcc aacgttactc   7560
```

-continued

```
ggctctaacg cggtaacatg aggtcggacc cgttgtcctc actttgtagg agagcccttt   7620
tttttttttt ctttctttac ggaacacgtc atccgtagac cagactccaa agtagaacaa   7680
tgtaccactt gtagtcctgt ctttgttcat tcttagtacg gactacaata aaagacgtgt   7740
aagtttgaac gattgttaaa taactctaaa attcgtgaga cagagactag aaccccttt t   7800
cgaatcaact tccgtaatct ttctctcctc cctccgccat tcttacccca tcgaaactgt   7860
cttgccaccc ttggtggaaa tcccagactt tcctaaacgt ctagagactc acaacacttc   7920
taaacgagct gtaaagtaga caagagaaaa tctagtttga cacaataatt ggaacacgga   7980
ctatttgttg ttcacgaagt cctccgtata gcccacgact tccactcctc ctctcactct   8040
atttaataga aacttgtagt cattctcgac tacccaattc agaacaaaca agggggaact   8100
tgattctcga gtttgagaga attaaatagg taatttactt attccccacc gttttccccc   8160
ttccccgtcc ttatggggcc tatacctaat gaaagggaga atccaacgtt ttccatcatt   8220
taggctccac tgtcaacagt gacttacaca attccataaa cgaaagaact gacagagagg   8280
ataaacgacg acatgtacta ggatcttctc gtagacacct cgatatcctt agaaacgtga   8340
ctgatgatta ctaacgaaac ttatatgaga gaagatcgta catgtcacaa agagtcccga   8400
agactaaaga atagacagta ctaaagtcta gaaacccttc aatgtcttct accttgaaaa   8460
tgtaattgat gaacgatttt cctttcgaac gtcctcgagg tgtcggaagt aacatagtac   8520
tctacacata gaagtactat catctacttt ataagtcggt ccacgccatc gagtgtggac   8580
attagggtca cgacaccctc cggctccgcc cgtctagtgg actccagtcc tcaaactctg   8640
gtcgaaccgg ttgtacctct ttgagacaga gatgattttt atgtttttaa tcgacccaca   8700
ccaccacgca cggacattag ggtcgaggag ccctccgact ccatcctctt atcgaacttg   8760
ggtcttcagt ctccaacgtc actcggtcct agcacggtga cgtgaggtcg gaccctctgt   8820
ctcgctctga ggtagagttt tttttttttt tttttttttc taagatcgac ccacccacca   8880
tgtacggaca tgagggtcga tgaacctacg actccgttct cctaacgaac tcgagacctc   8940
aaacacacgt cgaacccgtt atatcacact agtgacggag attttttttac aaaaaaaaaa   9000
actctacctc agagtgagac gacaggtccg acatcacgtc accgtcctaa agtagagtga   9060
cgttggaggc ggaggaccca agtttgttaa gaaaacggag tcggagggat catcgaccct   9120
gatgtccgca cacggtggta cgggtcgatt aaaaacatga aaatcatctc tgttctaaag   9180
tggtataacc agtccgacta gaacttgagg actagagtac tagacggagt cggagggttt   9240
cacgacccta atgtccgtac tcggcgacac ggaccggttt taaaaaaaaa tttaactgtt   9300
gtctaaaaac tctaaaaacc aaatgtttcg acagtatctt gagtttatgt ttatagatat   9360
atctttacta aattactaaa tcactacaga aacaatcata cagtaaaatg tgcggtcaag   9420
tgatagaggt ggtttttaca tgaatatttt ccatctttgt gataatatct tagatctaga   9480
ggtccaaagg tccaaaaact ttaatcgatt tattttacaa ttcaaggact agtgagtaaa   9540
cggaatgtaa aattcctatt ataaaatttc tattttacac aacaatattt tcatttattg   9600
ttgtaatgtt tttcaatata aaaaattatc tttaccccag aacgacagtg ggtccgacct   9660
tacgtcacag tgatagacat ggggagattg aggactcaat ctccccaggt ctatcactgt   9720
gagtgacatg ggagattgag gacccgagtt tgttaggaga actcatcgat cctgaggtcc   9780
gtgtacggtg gtacgggtcg atcaaaaatt taaagatata ccctctctcc cagaacgaca   9840
caacggttcc gatcagagtt tgacgagagg aggtcgttcg gagggtgaag ccggaggact   9900
cagtaaccct aatctccgga ctcggtagta tggaccgttt caatatgata agaattctct   9960
```

```
attttctaat acttatgact actataggag acaagatgtt actggacccc gacgaaaacc  10020
aagtctaacc gatttttaaa tttacattca ttggactttt agaaataaat cctctgtctg  10080
tgagaatctt acactaaaat aatggacaac ctattcggtg accctccttt tttttggaac  10140
cgtgaactga taactaacat tgatttctcc gtcgacgata aacaagtgtt tcccagtcga  10200
atttgtaacg ataactaaaa atttaaacta aaacaagggg ataaggaaag aaacaataca  10260
ccccagttac attagtaatt agtagaacaa acctgattat acggagacaa agtcgtacca  10320
cccctcaata taaagtcact gcagatatgc tcggaacttg acggtcttct ttagtcctgt  10380
gtgtttcaaa ataccccatc cactaaaaca aatcaaatca taattccgtc taccaacatg  10440
tacacgtctt gaggaaagac gattatcggt cctactccga tatactctag tgtaccccaa  10500
tccggtactc cggttccaag gtaagaagga gacggtaagt tttcactatc ccgaaaccta  10560
tcaaattaag tagagaaact caatagcaaa aggtttaaca ttttacattt attattatgt  10620
tagacggaat atcccgacaa tacttctaat ttaccctatt tcttaccctt tttatgaaac  10680
ttttgagatc acacctttac tcctgttaac aagggttcga ccacaggaga atcaggggaa  10740
tacaagagta gtaataacac aagaaataag gaaataatag taaaattatc agaccttcaa  10800
ctctatttac gtacgaaaag tagtcagata ctttagtttt caagaataag aattttatta  10860
taattgaaat aagaatgata cattattatt tatccatggc aattgttcaa cctttcacgg  10920
tttttttttt ttttttttct tttttaatga ttcgacctgt gtcaccgtgt gtggacattg  10980
gggtctataa accctccgac tcagtcctcc taacgaactc ggatcctcaa gtccatgtcg  11040
gacccacagt atcattttgg gatagagaat ttttttaatg aatattagta tattgggtca  11100
ctattgaaga aaaaaaaaaa aaaaaaaaaa actctacctc agagcgagac agtgggtccg  11160
atctcacgtc accgcgttag aaccgagtga cgttggaggt gaagggccca agttcactaa  11220
gaggacggag tcggagggtt catcgaccct aatgtccacg tacggtggta cgggtcgatt  11280
aaaaacataa aaatcatctc taccccaaag tgacacaacc ggtccgacca gaggttgtgg  11340
actggagtac tagacgggtg gagccggagg gtttcacgac cctaatgtcc gtactcggtg  11400
gcgcgagccg gatactaaat aaaaaatatg atgaaataag tgtattgtca cgaaaagtct  11460
tacaccgcat gacgtatgta cttataatac gaacgtcgac tcatcttggt taggtggtca  11520
ctcacaggac ttcttaccaa ggatctctgg tagtcgatcg tgtgggtcag aattggtacc  11580
gaaagatctg gaacctccct acgagttcaa tcgaagatga cgatcctaga tacaaaattg  11640
attatggtac aggattaatt aatatatctt cttatcaagg gaattatgac ataattcaca  11700
accgaccaga caccaaaaaa caacaacaaa caaaaaatcc actcacagac ccaccacgaa  11760
atatgacctt ccttgaacga caggaacgag ttttttaacc caagacggga ggtgcaaacc  11820
agtgacggtt agagtaatgt taagttttgt tccttgacct ttctcaatag ccattctata  11880
ctgtctgtcg tccctgataa tattgatgtc gaacttacta actttacacc actaatcatt  11940
cattgaagac ttcctcagag taactcccta tgaaagacaa tagaccttta tcgatagaac  12000
ggaggacatg ttaccattgg ggggtttttta aaactataaa ttatttcgtg aaacttcagt  12060
aagtcattta tctcacttca cgagtctttc tattgactac tgtacgttcc ttcttttagt  12120
agaaatattg cacaaacgag gaacagacga ctcgttccgt tgttgacccc ctcacgacct  12180
ctacttggca cttatttaag ataaaaatcc actgacagca aaacaaagac gttgtaaagc  12240
ggagaagttt gtgagattct gtcctggttg gttctctacg gttcaataaa tgttacctcc  12300
```

-continued

```
ttaatgtcct gtactttttc ttgattacaa actacggtta aaatgtaaat tccatttatt  12360
ttgttaaagg tactgaagac cataagaaag acgagaacgg gaacgaggtc gatagaaaag  12420
aactgaaacg taacggaggg taaaaagacc acaaccaaac aaacacacac acaaatttac  12480
atacacacac aaagttcacc tcatttttttc gtaaaaaagg ggttatgaat aaataaataa  12540
ctgtcccaga gcgagacagt gggtccgacc tcacgtcatc gtgttagtat caagtgacgt  12600
cggactggag gacccgagtt cgctaggagg gtggagtccg aagactcatc gatcctgatg  12660
tctgagtagt ggtgtggacc gattataaac ataaaaaaca tctctacccc aaaacggtac  12720
aacgggtctg accagaactt gaggacccga gttcactaca cgggtggagt cggagggttt  12780
cacgacccta atgtccgcac ttggtggcac gggtcgggag ttataaataa tatttttaca  12840
aaaaccggtc cacgccaccg agtgtggaca ttaggatcgt gaaaccctcc gactccgtcc  12900
gtctaatgga ctccagtcct caagctctgg tcggactgct tgtaccgctt ttgggtagag  12960
atgattattt ttatgttttt aatcggcccg caccaccacc cacggacatt agggttgatg  13020
agacctccga ctccgtcctc ttaacgtact tgggccctcc acctccaact ccactcgact  13080
ctagtacggt aacgtgaggt cggacccgtt gtctcactct gaggtagagt tttttttttt  13140
tttttttct tcaaaaactt atgtcttttc aattatcatg ttacttatgg gtgtatccgt  13200
aatggatata aagtcgttaa ctcttgtaaa aaggtacaaa cacacaaata tacacatata  13260
tatatatata taaataaacg actcggtaac ttttattcaa cgtctataat actgtaaaat  13320
gggaatttat aaagtcgtac gcagggtatc cttacattat agggagacgt attagtgtta  13380
tggtaatgtg tggattcttt tgaaaaatgt tcttcggagt aagtctgtaa cctaattatc  13440
ccgatatctc ttcatcctac cttttctcat cctcatacat gttatcataa agttaacaaa  13500
ttaacacagt tccttaattc tttaaaatta caacctacta ccgtgattaa ccgtaaaaat  13560
gacgggacac gtatcattct aaacaaaaga gttttacctt ttcaagtccg aaaccttagt  13620
ctatggaccc aagtttaaga ccgagataat aataacaaaa aataaaaaaa aagacttaca  13680
gtgatctgtt tgaaaataac ttcgtattta acaccatgtc tttatgtaaa attgactaaa  13740
ttcaggttgt ggtcactttc ctctctaata ccgtggtttt gaaagggaaa ggatagtatg  13800
gtactaaatc taatactacg ttagatgtaa agagaaaaga tccgaaacag ggtatgttta  13860
aacccgtcaa aaagttgtaa tcttaaagtt gtaatcttaa gaattaagat aatccttttt  13920
ttcgttgttt ttttggtctg gagttcagtt gtttagataa cctataacaa atacttgctt  13980
caggtgcaat tcgtaaccag gagttttgtc tcgaggagtt ttataatcca cgacacgagt  14040
aatgtcttag tttgactagt gtgactaact tttgaaggag ttactttaaa agttagttgt  14100
tgtacgaagt ttattttcag tttgtcacaa ggttggtgaa ctgaagtttg gttcatctaa  14160
aatccaaatc tttgtgattt ttttccacaa agtaaatatt tatgtcttcc ttgtttttgt  14220
agtgacgtag ttaggtcttt aatagtttta taaatctcct gttctttata ttttaaatca  14280
gttgaaacga cgaaagagtc aaggaatttt agggtctcat agacgtttat atcgattttt  14340
catggttgag aactttcgga tataatgatc agtaaagggt aactcataaa accttaaaat  14400
aaatacaaga tgaataaata agtacataag acgaaatact acaaatagac ttattagacc  14460
tgtttaagag taagacccgt cagtaagcaa agtaggatac ttacggtacc actccctttg  14520
tcacatcaat ctccttgtct acttcagtct tgtgagtgta cgtagtgcca gtgtcttgaa  14580
attcagtgtt ctgtcttttc tttagctaag acgaaaccta gtttcaaata tcttgtgatg  14640
aattaccttt gatcaccttt accgacgatt tccttttcaa ttccacttac taggttcgac  14700
```

```
tgaactaatg acttaggtct tgttttaata cgatttagag agaccattaa ttgatttatt  14760
tttagtaaaa tatgataata aatcattcaa tcatttccgc acgatgagta atctacgatt  14820
agagtaaatg actccttgtg tcttaacata tacaaaagac cgagataata aataatgaac  14880
ccatttgaac ttgttcagtg gttttaagca acccaatgtc aaacaagatg acattttcgt  14940
ccctattatt atgaatgaaa cgtcttaaag atattcctaa tcgttattac atcgttttgt  15000
gacccatgta tgacgttcaa gtcacttttc ttctatgaca gtaataaaca aggttttcac  15060
cttcttgaat gataattata aagtaaaaag actaaataaa taaatagata aaatctctgt  15120
ttcagagaga gacagtgggt acgacctcac atcaccgtgt cagtatcgag tgacattgga  15180
gtttgaggac ccgagttcgc taagagggta gagtcggagg gttcatcgac cctgatgtcc  15240
gtacacagtg gtacggaccg attaaaaaat aaaaataaaa aaacaaccac tctgtccaaa  15300
aaaaaaaaaa agaaaaaact ctggttcaga gcgagacagt gagtccgacc tcacgtcacc  15360
gggctagagc cgagtgacgt tcgaggtgga gggcccaagt gcggtaagag gacggaatcg  15420
gagggttcat cgaccctgat gtccacgggc ggtggtgtgg gccgattaaa aaacataaaa  15480
atcatctcaa ccctaaagtg gcacaatcgg tcctaccaga gttagaggac cggagcacta  15540
ggtgggcgga gccggagggt ttcacgaccc taatgtccgc actcggtggt gagggccggt  15600
tctgtccaag aatataacgg gtccgaccag aacttgagga ccggagttcg ttaagagggt  15660
ggagtcggag ggtttcaacg ttcgtacaca gtgacacgga ccgaagaaga ctaaaaaaac  15720
cagatttatc gtagaggtct aaagaaaaaa aaaaaattaa attttttaca taaataaaga  15780
aataaatctg tgtcccagaa cgatacaacg ggtgtgaccc catgtgaccg ataagtgtcc  15840
acattcgtat cgggtgatat cagaacttga ggaccggagt tccctaggaa ggtggagtcg  15900
gaaggttcag accctgatgt agaccgattc gtagaagttt aaagaataaa taaataaata  15960
aataaaaact ctacctcaga acgagacaac ggatccgacc tcacgtcact gagttagagt  16020
cgagtgacgt tggagacgga ggacccaagt tcggctaaga ggacggaatc ggagagctca  16080
tcgtccctaa tgtccgcaca cggtggtgtg ggtcgattaa aaatataaaa ataatctctg  16140
tcccaaagtg gtacaaccgg tccgaccaga gcttgaggac tggagtccat tagatgggcg  16200
gagccggagg gtttcacgac cctaatgtcc gcactcggtg acacgggccg acgtagaagt  16260
ttaaagaatt tatgaggaac catatcacct cgggaattac gaaaagtgat tacgtgacga  16320
ggaactacac gacggataag gtcatctatg tgtcttagtc tcaccattcc cggaaacttt  16380
ggtaactaaa caagatcacc gaaagttttt ggtaaaaatt atgttaataa aaaattcgtt  16440
ttacaaaata tatatatata tataccaaaa aaaaaaaaac tctacctcag aacgagacaa  16500
cgggtccgat ctcacgtcac cacgttagag ccgagtgacg ttggagtcgg agggaccaag  16560
ttcactaaaa ggacggagtc ggaggggtca tcgaacctga tgtccaccca cggttgcgtg  16620
gaccgattaa aaacgtaaaa atcatctctg tcccaaagtg gtacaaccgg tccgaccaga  16680
atttgaggac tggagtccac tagacgggtg gagccggagg gtttcatgat cctaatatct  16740
acactcggtg acacgggtcg gtctttacgt gaaatttttg gtggtcagga acggacccgt  16800
accaccgagt gtggacatta gggtcgtgaa accctccgac tccgcccacc taatggactc  16860
cagtcctcaa gctctggtcg gactagttgt actactttgg gacagagatg atttttatgt  16920
ttttaatcgg cccgcaccac cgcacacgga caatagggtc gatgagctct ccgattccgt  16980
cctcttagcc gaacttgggt cctccgtctc caacgtcact cgactctaac tcagtgacgt  17040
```

-continued gaggtcggac ccgttgtctc gttctgaagt agagtttttg tttgtttgtt tctttttgg 17100 gggttatcag gtttcgggat taaaaggggg gtaataaata aaaaaattac ccgtttaaaa 17160
tttttaacat atatataaat accacatgtt accctacaaa actgtataca tatgtaatac 17220
cttactgatt tagttctatt aattttacgt aatggagtgt atgagtggta aataaacact 17280
actctagttt cagatgagaa aatcgttaaa agaaaaaaga aaagaaaaga aagaaataaa 17340
gaaaaaaaaa aaaaaaactc cgtcttagaa cgagacagcg ggtccgacct cacgtcaccg 17400
tgttagagcc gagtgacgtt ggaggtggag agtccaagtt cgctaatagg acggagtcgg 17460
aaggttcatc gaccctgata tccacacacg atggtgtggg tcgattaaaa aacataaaaa 17520
tcatctctac ctcaaagtgg tacaaccggt ccgaccagaa cttgaggact ggagtccact 17580
agggggacga agtcggaggg tttcacgacc ctaatgtccg cgctccacgg gtcggaaaat 17640
cgttaaaggt tatgtaacaa taattgatat cagtggtaca acatattatc tagagaaatt 17700
gaataaggac tattgacttt aaaacatagg aaattggttg tagataggac aaggtgggga 17760
cgggagggtg ggggatgggg gtcggggacc attctcggag atgagaagtg gagatactca 17820
agttgaaaaa ctttaaggtg tatattagat cgctccaata cgtcataaac aaaaagtcac 17880
ggacgtctat actgtaaaaa cccaagttga aaaacaaaca aaaactctac cttagagtga 17940
gaacagcggg tccgacctca cgtcaccgca ctagaaccga gtgacgttag aggcggagga 18000
cccaagttcg gtaagaggac agagtcggag gactcatcgt ccctaatgtc cgcggacggt 18060
ggcacgggtc gattaaaaac ataaaaatca tctctgcccc aaagtgatac aaccggtccg 18120
accagagatt gaggactgga gtctgctaga cggacgtaac cggaggtttt gacgacccta 18180
atgtccgtac tctgtgacgc tggccggttt gtaaaaaaat tacgtattat ctacatgtat 18240
gaaagtcccg tgtagactat taaattatat aagtatatta aacatgtcta gttcagttac 18300
attgaccata taggtagcgg aatttgtaaa cagaaaagaa ataagatcct tgggtaaact 18360
taataagaaa agatcgataa aactttatat gttatctaat aacacttgat atcagtggga 18420
tgactaggta gcttgtgatc cagaataaag aagaataatt tgacctaaaa catgagtaat 18480
tagttcgaga gaagtaggag gggtgagatg gaccgcagac cattggtggt tagatgagag 18540
ataatagtac tccaggtgaa aaaatcgagg gtgtatagtc gctcttgtac attataagca 18600
gaaaaactcc aaccgaataa agagaattgt attactggac gtcaaggtac gtacaacgac 18660
gtccactgtc ctaaaggaag aaaataaaat aaaataaaat aaaaaaactc tgtctcagaa 18720
tgagacagag ggtccaacct cacgtcaccg cactagaacc gagtgacttt ggaggccgac 18780
ggtccaagtt cattaagagg acggagtcgg aggactcatc gaccctgatg tccgcgcacg 18840
gtggtgtggg ttgattaaaa aaaaaaaaaa aaaaaaaaaa aaaaaaaaaa aaaaaaaaaa 18900
aaaaaaaact ctgcctcaga gcgagacagc gggtccgacc tcacgtcacc gccctagagc 18960
cgagtgacgt tcgaggcgga gggcccaagt gcggtaagag gacggagtcg gagggttcat 19020
cgaccctgat gtccgcgggc ggtgatgcgg gccgattaaa aaacataaaa atcatctctg 19080
ccccaaagtg gcaaaatcgg ccctaccaga gctagaggac tggagcacta ggcgggcgga 19140
gccggagggt ttcacgaccc taatgtccgc actcggtggc gcgggccggg tgattaaaaa 19200
cataaaaatc atctctaccc caaagtgtac aaccgttccg accagagctt gaggactgga 19260
gtccactagg cggacggagc cggagggttt cacgacccta atgtccgaac ccggtggcgt 19320
ggtccggtcc taaaggaaga aaaagttcag acttatcata aggtcacaca tgtatatgat 19380
gatgcaaaag aaataggcaa gtagacaaac tcagaagaaa aaaagaatca aatcgatttc 19440

-continued

```
taaataaaat aaaaaagttt tttgattaaa aagtaaaaca actagaagac ataaaaaaat  19500
cagagttaaa gtaaataaag acgacactac aagaaagaaa ggaagatgat taaaactcaa  19560
actaaacaag aacgaaaata tcaagggagt acccgtaatg atccaacaaa taaacttcag  19620
acaaggaaga aaggaagtaa ggaaggaagg agggagggag ggagggaggg aagaaggaag  19680
gaaggtaaga aagaaaaaaa aaactctccc ttagagcgag acaacgggtc caacctcacg  19740
tcaccgcgct agagtcgagt gacgttggag gtggagggcc caagttcgtt aagaggacag  19800
agtcggaggg ttcatcgacc ctaatgtccg tacgtggtgg tgcggaccga ttaaaaaaac  19860
ataaaaatca tctctgcccc aaagtggtat aaccggtccg accagaactt gaggactgag  19920
acgggcggag tcggagggtt tcaagaccct aatgtccaca atcggtaaca cgggccggga  19980
agaaaggaaa gaagaagaaa gaaagagtcc cagagtgaga cagtggacct gacctcacgt  20040
caccacgtta gtaccgagtg tcgtcgaaac tggaggaccc gagtccgtta ggaggatggg  20100
gtcgtagggt tcatcgaccc tgattccgat ggtacggacc gactaaaaac ataaaagaca  20160
tctctgtccg aaagtggtac aacgggtcag acgagaactt gaggacccga gttcgttagg  20220
tggacggaac cggagggttt cacgactcta gaataaactt tagaaagttg aaaaaactat  20280
atccgtaatg aactttagaa agatgaaaaa actatatccg taaataacga tatttgaaag  20340
gagaatcacg acgaagacga catagggtat ctaaaaacgt acaacataaa ggtaaaagta  20400
gacaaagttc tataaaattt aaaaagagga ttaaagaagt acctgggtaa ccgataagtc  20460
ctcgtacaac aaattaaagg tacacaaaca cataaaaggt tccaagaaca ataactaaag  20520
attaaaataa ggtatcacca ctctttctat gaacaatact acagatgaaa agacttaaac  20580
aattctgaac aaaacaccgg attctatatc agatacgacc tcttacaagg tacacgataa  20640
ctcgtcttac agataagacg tcgtcaactc attttacgag acacttacag tcgatccgga  20700
taaactcgat catatatcaa attacaaaga aataataaaa gacagaccta ctagacaaaa  20760
tgactctcac tccacaccac aatctcaggg gatgatgata acgtaatgtc atatagagaa  20820
gaaaatctag ataattacaa acgaaatata tgaaacctcg aggttacaac tcacgtttct  20880
atgaatatag aagaacgact taactgggga aatagtaata tatcattgga agaaacggag  20940
aaactgtcgg aactaagtgt cagacaaaat agactacatt catatcgatg aggacaagaa  21000
aaaaccaaag gtcaacgaac cttacagaaa aaaggtgggg aattgaaggt cataaaaata  21060
ttcatttcat ccaaagaaca tccgtcgtat attaaaccag ggtaaaaaca taggtaagtc  21120
ggtgagataa ggaaaaaaaa cccccccaa gggttcaaaa taagttcttg agtatggttt  21180
ataaggtcta tttatttaaa aatagaagtg gaaggaggag aagaaaaagg tccaattaga  21240
ccttaattgc agtaagtatt attgagaaaa acgacaatcg ttgatgtgtg ttgtttagtg  21300
tatctaataa gaagtttata aaaaaccact ctataaagtt tatggaaaac ctttttccat  21360
ggagtcttca gtgtcactag aacgacaacg aggaaagcta ccaatattac gaggtggttc  21420
taagggtcga aaaggtaagt gaaattagga gagaacgttt ttgacgagtt ttaaccgtcg  21480
tagatactaa ggtaaaagat gttccaccca tgtcagttct cacttgtagt attggacgaa  21540
gaaaaaaacg gagagaaacg gtgttcgaaa aagtgtcgtg atacggagaa ttaacctctt  21600
aactcaggta aatgtaaatc acaataataa ctatgtattt ctgaattgta aaaaaattta  21660
actatgtatt aactacatcg ataaaacccc gcaagtacac tattaaatta tgtaagtata  21720
ttaaacattt ctaatttaat cacattaacc ctatggatag tggaagttat aaacagaaaa  21780
```

-continued

```
gaaaagaaaa aaaaagacac tctacctcaa aacgaaaaaa acgggtccga cctcacgtta  21840
ccgcgttaga gccgagtgac gttggaggtg gagggcccaa gttcgttaag aggacggagt  21900
cggagggctc atcgacccta atgtccgtac gtggtggtac gagtcgatta aaacataaaa  21960
atcatctctg ccccaaaatg gtacaaccag tccgaccaga gcttgaggac tggagtccac  22020
taggtgagcg ggaccggatg gtttcacgac cctaatatcc gtactcggtg gtgtggaccg  22080
ggacagaaaa gaaatacaac ctttgtaagt ttaataagag aagatcgata aaactttata  22140
tgttatataa taacatttga tcagtgaaat gactatatag tttgtgatcc agaataaaga  22200
aagtagtttg ggatatatat atatatatat atatatatat ataaaaaaaa aaaaaaaaac  22260
tctgcctcag agcgagacag agcgagacag cgggtccgat ctcacgtcac cgtgttagag  22320
ccgggtgacg ttcgaggcgg agggcccaag tacggtaaga ggacggagtc gcggggctca  22380
tcgaccctga tgtccacgga cggtggtacg ggccgattaa aaaacataaa aatcatctct  22440
gccccaaaat ggtacaatcg gtcctaccag agttagagga ctggaacact aggtgggtgg  22500
agccggaggg tttcacgacc ctaatgtccg aactcggtgg cacgggccgg tttgggatat  22560
aaatattggt aattagttga agagaaatag aggggggtaag acatgggaaa gaccggaaac  22620
cattgatagt tatatgagag atagaattac tcaaggtgaa aaaaatcgaa ggtgtatagt  22680
cactcttgta tactataaac agaaagacac aaacggaata aagagaattg tactggacgt  22740
caaggtacgt agaacgacgt ttactgtcct aaaggaagac aaaattttag acttatcata  22800
aggtaacaca tatatacggt gcaaaaggag taggtaagta ggtaacgacc tacgaatcca  22860
actaaggtat agaaccaata acactaatta cgacgtcagt tgtaatcctc acgtctataa  22920
agggactgta tgactaaagt aaagtaaggg aagggaaggg gacggacaga cggacggaag  22980
gaaggaagga aggaaggaag gaaggaaaga aggaaggaag gaagggaagg agggaggtgg  23040
gggggcggg gaaagtctac cttagaccga gacagcgggt ccgacctcac gtcaccgcgt  23100
tagagtcgag tgatgttgga ggcggaggac ccaagttcgt taagaagacg gagtcggagg  23160
gctcatcgac cctaatgccc gtacacggcg gtatgggtcg attaaaaaaa cataaaaatc  23220
atctccgtcc caaaatggta taaccggtcc gaccagagct tgaggactgg agtactaggt  23280
ggacggagtc ggagggtttc acgaccctaa tgtatccaca ctcggtggca tgtgtcggtc  23340
aaagtaaaag aaaagaaaaa aaaaaaaaaa actctgcctc agagcgagac aacgggtccg  23400
acctcacgac ctcacgtcac cgtgctagag ccgagtgacg ttcgaggtgg agggcccaag  23460
tgtggtaaga ggacggagtc ggagggttca tcgaccctgt tgtccgcgga cggtgataca  23520
ggccgattaa aaaacataaa aaaatcatct ctaccccaaa gtgacacaat cggtcctacc  23580
agagctagag gactggaaca ctagccgggt ggagccggag ggtctcacga ccctaatgtc  23640
cacactcggt ggcgcggacc gggtaaaaga aatctatata tgggttcatc cccctaacga  23700
cccagtatat catcaagata aaaattaaaa aactccttag aggtatgaca aagggtatta  23760
ccgacatgat taaatttaag ggtggttgtc acacattcct aatcacgacc actcctacac  23820
ctcttttgct atgaagaccc gtaaaaaaga agataactct gatttcaacg ttgagaatca  23880
taaaaaaaaa tatgatggga aatccttcca ctttaacaac ttcacctact tctttgtcgt  23940
cgatagaact tcttaagttc taaacgagtt ctaaaagact agtctggtta acctctcttc  24000
aacggttgta gacctccgac aagacgaaac ctcaatttcc aatcaaaccg aaagtgatgg  24060
actctcttga taaaataaat aaataaaaac tctacctcag agagagacag tgggtctgac  24120
ctcacgtcac cacactagaa ccgagtgacg ttggaggcgg aggacccaag ttcgttaaga  24180
```

-continued

```
gggacggagt cggagggcta atcgattcta atgtccgtgg gtggtggtgc gggccgatta  24240
aaaacacaaa aaatcatctc taccccaaag cggtacaacc ggtccgacca gaacttgagg  24300
actggagtcc attgggtgga cggagtcaga gggtttcacg accctaatgt ccgcactcgg  24360
tgacacgggc cggtcatacg taccagagaa ctccgcgtga agagaacgac cagtttacaa  24420
caatctgcca atatatggtc aatttgcggt ggtaaaacgg agaattacac gtacgaactc  24480
gggtgaacgg gttgagggct ctagaatagc ccttcgacga ctagtggtca aagtccacaa  24540
agacaaataa ccctctgaag gaaagggacc atgacagaca ctgattaata ctaaaagctc  24600
tctgtcaatt gttggtggac tagtagtgga ttactagcgg actgtaagga ccacctcagc  24660
cgcgcccctc gggagaggac gggacgagtg cggactgatc gataatatgg acgaaattgt  24720
tcaagaggtt ttaagtctct ggaaagcact cataagacta aaatattatt ttatcaataa  24780
acgtattcaa atcattctca gaaaagagag ttttgtcctg ttaacctctg tgaaccaata  24840
aaatggtttc gaaactgacc ttattgtaaa catccatttc aaggtcgttt cggttgaact  24900
tttctcggat agaccggttt gagaacgacc tgaagtacgt ttactagtcc gtttcaaatt  24960
attcggattt taaataaaac gtgtatttaa ccggaatgat attaaacaga aatcatattt  25020
tcctcctcga cccacgtctt caagtgtgag tattagggtc gtgaaaccct ccgactctgt  25080
ccgtctagtg aactccggtc ctcaaactgt ggtcggaccc attgtacaac tttgggacag  25140
agatggtttt tatgtttttt taatagaccc ataccaccac gtacgaccat caaggtcaat  25200
gagttctccg actctaccct cctaacgaac tcgggtccct ccacctcccg ttactcggtt  25260
ctgacgtggt gacgtgaggt cggacccgtt gtctcactct gagacagagt ttttttttt  25320
ttttttttt tttttctttc ttccgatctc tctctttacc aaagtttcct tttgatattg  25380
tgaacaatga tctaaaggtc ggacctgaaa acaaaaactc acgtataact tagtaattaa  25440
taaagaaccg atgttattgg gagatttcta tttggtccaa tattaaaaag aagtacaaaa  25500
atcaaacacg ggattcacct tatccaagga ataagacaag actgtgtgct tatgagaaaa  25560
ctgacagtat aataattaca ataaatatcg aggaacaaaa tgaaggtttc tttggtctta  25620
gtactataag attccaatct cttagggggc aaaccttagg gtgaccagga ttagacgaaa  25680
agtgacgttt aaggcacgac gattttaata tattcgtgag aagagatccg ggtccctgga  25740
tagtgtgttt tccatccaca cactctgaca ttcccggtca aaactctctt aataaagtct  25800
gagaggttta gtttttaccc gtgtgtctac gtatttgtcg accattttat tccctgagac  25860
ggaggaccca ataatacaca caccgtggaa aagtaggtag ggttagtatt tcttaaagga  25920
cgaagagcat cttacttttc ttttaataat gactctccta tatttccatg gagtacagtt  25980
tcggaggatc caaattatga gactcaatac tctaaatacg tctattgtat atataaaaaa  26040
ttttaaaatc ttgtccggtc cgtgtcaccg agttcggaca ttaggatcgt gaaaccctcc  26100
ggttccaccc gtctaacgga ctcgagtcct caagttctgg tcggacccgt tgtaccactg  26160
tggggtagag atgattttat gttttttatt taatctaccc gtaccaccgc acgcggacat  26220
cagggtcgat gaaccctccg actccgtcct cttaacgaac tcgggccctc cgcctccaac  26280
gttactctgc tctaactcta ccgcggtgac gtgaggtcgg accgttgtct cactctgaga  26340
cagagtttta tttatttatt tatttattta tttatttatt tatttattta ttaaaatctt  26400
gtttaatgac tttctggtgt ttttttttt gacatcgtgt tgccttcaga gatttaagga  26460
atcgaatttt ccaaaattgt cacgaataca aaacatatcg attaacgaca ttcagacatt  26520
```

-continued

```
gattttggtt ctaatgtcat cgtgttacgt atcttcaatt tctattcagt taaaaaattg  26580
gagtggaaac cgaaaaacaa acaaccgaaa atataattct ttaaaattcc caaataatta  26640
cggataggtg taggtaaggg tagaccggat cttgaaagaa aaaaaaccac cccctccccc  26700
tgcctcagaa ggagacagtg ggtccgaccc cacgtcaccg cactagagta gagtgacgtt  26760
ggaggcggag tgtccaagtt cactaagagg acggagtcgg aggactcatc gacattaatg  26820
tccgtacacg gtggtacgga ccgattaaaa aaaaagaaaa aaaaaaaaaa aaggctctac  26880
ctcagaacga gacaacgggt ccgacctcac gtcaccacgc tggagccgag tgacgttgga  26940
gacggagggt tcaagttcgc taagaagacg gagtcggagg tctcatctac cctgatgtcc  27000
acgcacggtg gtacggaccg attaaaaata aaataaaaaa atcatctcta ccccaaagta  27060
gtataaccgg tccgaccaga gcttgaggaa tggagtacta ggtgggtgga accggagggt  27120
ttcacgaccc taatatccgt actcggtgac acgggtcggg attaagcata aaaatcatct  27180
ctgtcccaaa gtggtacaac cagtccgacc agagtttgac gactagaatc cactggttgg  27240
acagagccgg agggtttcac gactctaatg tccccacttg gtggtacgga ccagaccgga  27300
tcttgaaagt ttaagcgata cacagaaaac cgagattcgg ggaactggta tccccagggt  27360
ggttccgtgt tctacctggg tcccttccgt cgacacggtg gggtcgttgt gtcactctat  27420
tttattttca aaccactggt aactacaacg gagactgttt agatccggtc ttacgcctct  27480
ttcatttagt ttttatttta agatccggcc cgcgccaccg agtgtggaca ttagggtcgt  27540
gaaaccctcc ggctccgccc acctagtgtt ccagtcctca agctctggtc ggaccggttg  27600
tatcactttg gggcagagat gatttttatt ttttagtcgg tccgcacccc cgtccgtgga  27660
catcagggtc gatgaaccct ccgactccgt cctcttaagg aacttggacc ctccacctcc  27720
aacgtcactc ggctctagta cggtgacgtg agattggacc cgctgtctcg ctctgaggta  27780
gagtttttta ttttttttta ttttttttatt tttttatttt attttaatat ttgggagttg  27840
gtagacttgc ctggggagga cagcccgttt ccgtaacgtt tcaataggat tttttgatca  27900
agtccagtgc ttcccttcct cttcaaacct gtacggagta ataagggagg agggaaaacc  27960
ttaagtctgt gacgactggt cgtaatggta attttgtcta gaattctgac tatcttgtct  28020
gagaaattta gaccattctt tgtaaatgtt agataagaga gacatcggac gacggatctc  28080
cgaagtagac gtactatttt ggaaccagag gtgttagaga atagtattgg atctgtgagg  28140
gaagataact agggtccaga aacctaatat tgagttggtt aacggttagt gttttagaaa  28200
cttagacgga cactggacct ttaggggtga aggtcaacag ggtgcaaaga ccagacttgg  28260
ttacatgtat aatatacata actaactaca gaatacagag agattttaca tattttggtt  28320
caatatccca ctggtgaaac ccgtgtacaa acgtctagag gactcccgac acagtgtccg  28380
gtaaccagtg aataaaccga gtcttattta gaaaaattca taaaatctca aactgggaaa  28440
aacaactgtt acaaattgta ggatgtcaat actgtgggat taaacttaaa tatgtcgaat  28500
tgaagttatt gtatgatttt aagacgagga aatttcgaac aagagttgat aaaatcaaga  28560
aaaaaaaaaa aaaggtaact gtctcaaagt gagatagtgg gtccgacctc acgtcaccgt  28620
gctagaaccg agtgacgtcg gagacggagg acccaagttc actaagagga cggggtcgga  28680
gtgttcatcg accctaatgt ccacgcggtc ggtggtacgg accgattaaa aaacataaaa  28740
atcatctccg ccccagagta gtacaaccgg tcggaccaga gcttgaggac tgtagtctac  28800
taggtggtcg gagccggagg gtttcacgac cctaatgtcc acacttgatg gtgcgggccc  28860
agaaagatca agaactatag tgttttaata cagaaataag taaaacacgg gggttttgca  28920
```

-continued

```
tttgattatt aataaaattt acgtaaccag agaatttagt acaccttttg tttttcatct  28980
caatgtttgg taacaatgtt attatgatcg aaacggccca caccaccgaa tgcggtggtc  29040
cactaggtgg gtggatccaa cgggtcggac ccgttgttct cgtgttgagg tagagttttt  29100
ttgtttttgt ttatttgttt tttggggtta ttatggtcga aaaaaaaaaa aaactctgtc  29160
tcgaagcgag aacaacgggt ccgatctcac gttaccacgc cagaaccgag tggcgttgga  29220
ggcggaggac ccaagttcgc caagaggacg gagtcgaagg gttcatcgac cctaatgtcc  29280
acgcgtggta gtgtcggccg attaaaaaca taaaaatcat ctctgcccca aaatggtaca  29340
accagttcga ccagagtttg aggactggag tccattaggt ggacggaacc ggagggtttc  29400
acgaccctaa tgtccgtact cggtggcacg ggccggttag ggtcgtgaaa ccctccgact  29460
ccgaccgtct ggtgaactcc agtcctccag ttctggtcgg accggttgta cgactttggc  29520
acagacatga tttttatgtt tttaatcgac ccgtgccacc gtttacggat attagggtca  29580
atgaaccccc cgactccgtc ctcctagcaa aactcgggcc ctacacctcc gacatcactc  29640
ggcactagtg ttgtgacatg ggtcggaccc cgctgtctcg ttctgggacg gagttttttt  29700
tttttttttt tcgtgtttcg aaaaactctt tagtgaaagt ttttaccatg taaacatcaa  29760
ccccttccaa ttagcttgga ttttatattc ttaggacctg ggttttgga cctcggtcat  29820
aatggtcgta cttagattgg gttcgagtca tatgttcggt ggacatctcg atttctcact  29880
aaatgatccg gcccgtgcca ccgaatgcgg acattagggt cgtgaaaccc tcggctccgc  29940
ccacctagtg ctccagtcct caagttctgg tcggaccggt tctaccactt tggggcagag  30000
atgattttta tgtttttttt aatcggcccg caccaccgta cgcggacatt agggtcgatg  30060
aggtctccga ctccgtctct taacgaattt ggacctcccc gcctccaacg tcactcggct  30120
ctagcgcggt gacgtgaggt cgaccccact gtctcactct gaggtagagt tttttttttt  30180
ttttctcact aaatgaaaga aacgaaataa tttaagaagt cgtgagacga taagactgag  30240
aagacaacaa gcttcttcca ctatgaaacc tttcatctgt ctaaaccgaa aactcataag  30300
ttaggtaatt tgtaaagttt ttatacagtg actataaaac tttgaggact ctcaagtaac  30360
tattcctttc gacgaccact cttagttata aataaaattt tccgaaaata gtaagattaa  30420
gaagattttg gaccaaagga tttatgacta atattttcga tagtcttccg caccaccgag  30480
tgcggacatt agggtcgtga aacccctccg gctccgccca cctagtgctc cagtcctcta  30540
gctctggtag gaccgattgt gccactttgg ggcagagatg atttttatgt tttttaatcg  30600
gcccgcacca ccgcccacgg acatcagggt cgatgagccc tccgactccg tcctcttacc  30660
gcacttgggc cctccgcctc gaacgtcact cgtctctagt acggtgacgt gaggtcggac  30720
ccgctgtctc actccgaggc agagttcttt ttttttttta cgatagtctt ctattaccaa  30780
tgttcatttc tcccagaaag gagctcgatg tcataaaagt cacatgagac cgaaaaaaaa  30840
aaaggaaact ctgtctcaga gcgagacagt gggtccgacc tcacgtcacc gtgctagaac  30900
cgaatgagga ggcggaggac ccaagtttgt taagaggacg gagtcgaagg gctcatcgac  30960
cctgatgtcc gtgtgcggtg gtgcgggccg agtaaaaaac ataaaattat ctctgcccca  31020
aagtggccca acgggtccga ccaccacttg aggactcgag tccgttaggc gggcggagcc  31080
ggagggtttc acgaccctac tgtccacact cggtgacacg ggtcggtgag accgataaaa  31140
aaaatttttt cctcaattta ctcaaacgaa gacgtctact ggtaaaagaa agacgcatcg  31200
acaggaacaa gagggagggt cacacgcacg ttgtgtacat gtcctccaag aactggaatc  31260
```

-continued

```
tatatttaac attttaaggt gtataaactt gaccaaatag ggttgtattc cagaggaaag 31320
acgaaataaa gtcggacgtc tacacggtta cagaaatcca gtcaaagttc aaaaacttta 31380
cccttattca ctgtgacttc cttctaaaat tatttacttt gtcaacacac tggatcctta 31440
tattggaaca cgagaatccc ttcctgtaag aatagaaaaa aaaaaaaaag aattgccttc 31500
tggaaatact atttgcgacc tcatgtctgt catgtgcgtc gaccgtacgt cccataacgt 31560
atatgaattg tagaactctc aggaagacga aaaagaagta gaagaaaaat taggactata 31620
cgttttacat aaaacggtaa ttttgttaac atgataattt tgtgacgtcg tagaccgacc 31680
cgcaccaccg agtgtggaca ttagggtcgt aaaaccctcc gactccgccc acctagtgaa 31740
ctccagtcct caagttgtcg tcggacagat tgtaccactt tgggggagag atgattttta 31800
tgtttttaat cgacccacac caccgcccac ggacattagg gtcgaaaaac cttctgactc 31860
cgtcctccta gtggaccctc cgtctccaac gtcactcggt tctagcacgg tgacgtgagg 31920
tcggagccgc tgtttccctc tgagggagag tttttgtttt tttgttgttt tgtgacgtcg 31980
tagactttac tacgtttgtc ctaatcccga tacctgacag aattatcatt accatcatta 32040
tcgtaattgt tggtatcgtc attatatctc cttaattgaa aataacttat caattataca 32100
aattccgtgg gacagtaaat caggagtgtt agtggggata atagaagtaa actgtctacc 32160
tctctgactc cgagactttc taagtaaatg tttaggtttc agtatgtcga tctttcacca 32220
cttaaacgtg ggtgtagact aagacctcga ccgtgagatt tggtcacacg acgaggtaga 32280
gaggtatcaa catgaagagt atcttagtgt cctacaacca cgtcctttcc tgacgaatat 32340
agacccatgg ggtggaaagt aaaggaagtt cagaactcta gaaaaacttg atcttcgtac 32400
gtaaatcttc actataacta tagtggtaga ggacaaccat ctatctagta actcaccttt 32460
cttctcccaa gttccctaag agggtggagt cggagtatca tcggtggtgc gggttgatta 32520
aaaatataaa agtcatctct gccccaaagt agtacaaccg gtccgaccag agcttgagga 32580
ctggagtcca ctaggtgacg gaaccggagg gtctcacgac cctaatgagg gtctcatgta 32640
ctcggtggcg tggtccggtc ccgtttggga aagttcgtcc tcaaggtcat atgactctct 32700
acctttacgt taactacact tcaggatcgt catcgttggt cgtctcgacc ggaagaaggt 32760
ccgaacctct aggagacggt ctacgagtag aatggtctac gtccgtctgg agaagtaaag 32820
tctttccatc tgtgactccc tgtctctctg gttccggtcg tccttcagtc agtgaaatca 32880
tttcccaggt ggtcagatag tcaaagtact tacatctcag acacggacgg aacatgtggg 32940
gagataaacg tcactggtct tattcatcat cctgacattt aaatacaata ttacttaagt 33000
aatggtaata aatttcaccg tacaagtacg aaaaaaaaaa aaaaaactct acctcagagc 33060
gagacagtgg gtccaacctc acgtcaccac actagagtcg agtgacgttg gaggtggagg 33120
atccaagttc actaagagaa cggagtcgga gggctcatcg actctgatgt ctgcacggtg 33180
gtgtgggtcg attaaaaaac ataaaaatca tctctaccct aaaacggtat aacgggtccg 33240
aacagagttt gaggaccgga gtccactagg taaccggagc cggagagttt cacgacccta 33300
atgtccgcac tcggtggcac gggtctggga cacgagaact aaaggataga aacatgaacc 33360
gaaaagagac cggggtgacc atgataacaa tctccataga gtaaacctcc actttcctcc 33420
cctttattta tgtcgtcaga acagaaaatt tatttatgtc gtcagaatac aatgagatga 33480
gactctagac agaccggtaa caaccgttaa agtagactcg tagtcgttaa cgatcactgt 33540
cgggatgtag accctgagtg aaaggacaaa ccatatttac aaagacctct aatcttattc 33600
ccttctcttc agcaaaatcg taaaggcata gagtcaaggt ttctccaaat tttccgtgca 33660
```

```
cgtttactgt tggggtgttt tgttttagtt gactcgtttt tagttacgag acgggttctc  33720

cctggtagaa attcttcgaa attcacttca aatggaactt tcaacattaa tcttcgaagt  33780

ccttcgttca cggaaatacc gtcttactga ctacaatgag ggtcctagag taccttaaca  33840

ttttaaaata gagacaagac acattcagtt ggatttagtt tgtctttata atcacaaacc  33900

catgtagttt tgtggaaatt gaacaggaaa gtaaaaccaa acggaaaact gtcctatatt  33960

agtgtctagg taaattcgaa cgtcttctca gactgtcata cttcaggtct acacagggac  34020

tacgacgacc tccgacgaca ccgtgtttct tttcgacgat ttagatatcg gttggtcccc  34080

tggtgtcatc acccgttctc actagacgta caaaaaattg gacgaaaagg ggtatcgtgt  34140

ctggtattct ttgttgttta ccccggcccg tgtcaccgag tacggatatt agggtcgtga  34200

aaccctccgg ctccgtccgt ctagtggact ccagtcctca aactatggtc ggaccggttg  34260

taccacttta ggacagagat ggtttttatg ttttttttaa tcgacccgta ccaccacgtg  34320

tggatatcag agtcgatgag ccctccgact ccgtcctctt aacgaacttg ggtccttcat  34380

ctccgacgtc actcattcgt agtgcggtga catgaggtcg gacccgttgt ctcgttctga  34440

gacagagttt tcgttttttt tttttttttt ttctttcttt ctttttcttt tgttgtttac  34500
```

<210> SEQ ID NO 3
<211> LENGTH: 1735
<212> TYPE: DNA
<213> ORGANISM: Homo Sapiens

<400> SEQUENCE: 3

```
gagacagtga gtgcgcgccc tgagtcgcag gccgaggaga cagtgagtgc gcgccctgag     60

tcgcaggccg aggagacatg gctgcacttc gtgacgctga gatacagaag gacgtgcaga    120

cctactacgg gcaggtgctg aagagatcgg cagacctcca gaccaacggc tgtgtcacca    180

cagccaggcc ggtccccaag cacatccggg aagccttgca aaatgtacac gaagaagtag    240

ccctaagata ttatggctgt ggtctggtga tccctgagca tctagaaaac tgctggattt    300

tggatctggg tagtggaagt ggcagagatt gctatgtact tagccagctg gttggtgaaa    360

aaggacacgt gactggaata gacatgacca aaggccaggt ggaagtggct gaaaagtatc    420

ttgactatca catggaaaaa tatggcttcc aggcatctaa tgtgactttt ttccatggca    480

acattgagaa gttggcagag gctggaatca agaatgagag ccatgatatt gttgtatcaa    540

actgtgttat taaccttgtg cctgataaac aacaagtgct tcaggaggca tatcgggtgc    600

tgaagcatgg tggggagtta tatttcagtg acgtctatac gagccttgaa ctgccagaag    660

aaatcaggac acacaaagtt ttatggggtg agtgtctggg tggtgcttta tactggaagg    720

aacttgctgt ccttgctcaa aaaattgggt tctgccctcc acgtttggtc actgccaatc    780

tcattacaat tcaaaacaag gaactggaaa gagttatcgg tgactgtcgt tttgtttctg    840

caacatttcg cctcttcaaa cactctaaga caggaccaac caagagatgc caagttattt    900

acaatggagg aattacagga catgaaaaag aactaatgtt tgatgccaat tttacattta    960

aggaaggtga aattgttgaa gtggatgaag aaacagcagc tatcttgaag aattcaagat   1020

ttgctcaaga ttttctgatc agaccaattg gagagaagtt gccaacatct ggaggctgtt   1080

ctgctttgga gttaaaggat ataatcacag atccatttaa gcttgcagaa gagtctgaca   1140

gtatgaagtc cagatgtgtc cctgatgctg ctggaggctg ctgtggcaca aagaaaagct   1200

gctaaatcta tagccaacca ggggaccaca gtagtgggca agagtgatct gcatgttttt   1260
```

-continued

```
taacctgctt ttccccatag cacagaccat aagaaacaac aaatgagcca ctgcgcccgg   1320

ccataaatga attattttta agaggcattg attaaagatt cacagcaaat cactagttaa   1380

gcagattttt tttctatttc ctacttcaaa gttctggtgc cacatagtgg tcagaaatgg   1440

aacagagaag ctgtcttaag ccttgttcaa gaagcaggaa aggcatcaga agaagtaaca   1500

gttggcagag ggtctcagga aaaacatctt ccttctgatc ttttgcatag caccttttgg   1560

aattttcatc atgtttgctt attaaacaaa gctcctactg ccatcatact aatcatgcaa   1620

aaagattgcc aaatcatgtt tggtaggagg acttttgagg tagcttttga acaaatgttt   1680

ttttcttttt tcttttttt tgcaataaag aaaacaaatt aatcataaaa aaaaa         1735
```

<210> SEQ ID NO 4
<211> LENGTH: 1735
<212> TYPE: DNA
<213> ORGANISM: Homo Sapiens

<400> SEQUENCE: 4

```
ctctgtcact cacgcgcggg actcagcgtc cggctcctct gtcactcacg cgcgggactc     60

agcgtccggc tcctctgtac cgacgtgaag cactgcgact ctatgtcttc ctgcacgtct    120

ggatgatgcc cgtccacgac ttctctagcc gtctggaggt ctggttgccg acacagtggt    180

gtcggtccgg ccaggggttc gtgtaggccc ttcggaacgt tttacatgtg cttcttcatc    240

gggattctat aataccgaca ccagaccact agggactcgt agatcttttg acgacctaaa    300

acctagaccc atcaccttca ccgtctctaa cgatacatga atcggtcgac caaccacttt    360

ttcctgtgca ctgaccttat ctgtactggt ttccggtcca ccttcaccga cttttcatag    420

aactgatagt gtaccttttt ataccgaagg tccgtagatt acactgaaaa aaggtaccgt    480

tgtaactctt caaccgtctc cgaccttagt tcttactctc ggtactataa caacatagtt    540

tgacacaata attggaacac ggactatttg ttgttcacga agtcctccgt atagcccacg    600

acttcgtacc acccctcaat ataaagtcac tgcagatatg ctcggaactt gacggtcttc    660

tttagtcctg tgtgtttcaa aataccccac tcacagaccc accacgaaat atgaccttcc    720

ttgaacgaca ggaacgagtt ttttaaccca agacgggagg tgcaaaccag tgacggttag    780

agtaatgtta agttttgttc cttgaccttt ctcaatagcc actgacagca aaacaaagac    840

gttgtaaagc ggagaagttt gtgagattct gtcctggttg gttctctacg gttcaataaa    900

tgttacctcc ttaatgtcct gtactttttc ttgattacaa actacggtta aaatgtaaat    960

tccttccact ttaacaactt cacctacttc tttgtcgtcg atagaacttc ttaagttcta   1020

aacgagttct aaaagactag tctggttaac ctctcttcaa cggttgtaga cctccgacaa   1080

gacgaaacct caatttccta tattagtgtc taggtaaatt cgaacgtctt ctcagactgt   1140

catacttcag gtctacacag ggactacgac gacctccgac gacaccgtgt ttcttttcga   1200

cgatttagat atcggttggt cccctggtgt catcacccgt tctcactaga cgtacaaaaa   1260

attggacgaa aaggggtatc gtgtctggta ttctttgttg tttactcggt gacgcgggcc   1320

ggtatttact taataaaaat tctccgtaac taatttctaa gtgtcgttta gtgatcaatt   1380

cgtctaaaaa aaagataaag gatgaagttt caagaccacg gtgtatcacc agtctttacc   1440

ttgtctcttc gacagaattc ggaacaagtt cttcgtcctt tccgtagtct tcttcattgt   1500

caaccgtctc ccagagtcct tttgtagaa ggaagactag aaaacgtatc gtggaaaacc   1560

ttaaaagtag tacaaacgaa taatttgttt cgaggatgac ggtagtatga ttagtacgtt   1620

tttctaacgg tttagtacaa accatcctcc tgaaaactcc atcgaaaact tgtttacaaa   1680
```

```
aaaagaaaaa agaaaaaaaa acgttatttc ttttgtttaa ttagtatttt ttttt       1735


<210> SEQ ID NO 5
<211> LENGTH: 375
<212> TYPE: PRT
<213> ORGANISM: Homo Sapiens

<400> SEQUENCE: 5

Met Ala Ala Leu Arg Asp Ala Glu Ile Gln Lys Asp Val Gln Thr Tyr
 1               5                  10                  15

Tyr Gly Gln Val Leu Lys Arg Ser Ala Asp Leu Gln Thr Asn Gly Cys
            20                  25                  30

Val Thr Thr Ala Arg Pro Val Pro Lys His Ile Arg Glu Ala Leu Gln
        35                  40                  45

Asn Val His Glu Glu Val Ala Leu Arg Tyr Tyr Gly Cys Gly Leu Val
    50                  55                  60

Ile Pro Glu His Leu Glu Asn Cys Trp Ile Leu Asp Leu Gly Ser Gly
65                  70                  75                  80

Ser Gly Arg Asp Cys Tyr Val Leu Ser Gln Leu Val Gly Glu Lys Gly
                85                  90                  95

His Val Thr Gly Ile Asp Met Thr Lys Gly Gln Val Glu Val Ala Glu
            100                 105                 110

Lys Tyr Leu Asp Tyr His Met Glu Lys Tyr Gly Phe Gln Ala Ser Asn
        115                 120                 125

Val Thr Phe Ile His Gly Tyr Ile Glu Lys Leu Gly Glu Ala Gly Ile
    130                 135                 140

Lys Asn Glu Ser His Asp Ile Val Val Ser Asn Cys Val Ile Asn Leu
145                 150                 155                 160

Val Pro Asp Lys Gln Gln Val Leu Gln Glu Ala Tyr Arg Val Leu Lys
                165                 170                 175

His Gly Gly Glu Leu Tyr Phe Ser Asp Val Tyr Thr Ser Leu Glu Leu
            180                 185                 190

Pro Glu Glu Ile Arg Thr His Lys Val Leu Trp Gly Glu Cys Leu Gly
        195                 200                 205

Gly Ala Leu Tyr Trp Lys Glu Leu Ala Val Leu Ala Gln Lys Ile Gly
    210                 215                 220

Phe Cys Pro Pro Arg Leu Val Thr Ala Asn Leu Ile Thr Ile Gln Asn
225                 230                 235                 240

Lys Glu Leu Glu Arg Val Ile Gly Asp Cys Arg Phe Val Ser Ala Thr
                245                 250                 255

Phe Arg Leu Phe Lys His Ser Lys Thr Gly Pro Thr Lys Arg Cys Gln
            260                 265                 270

Val Ile Tyr Asn Gly Gly Ile Thr Gly His Glu Lys Glu Leu Met Phe
        275                 280                 285

Asp Ala Asn Phe Thr Phe Lys Glu Gly Glu Ile Val Glu Val Asp Glu
    290                 295                 300

Glu Thr Ala Ala Ile Leu Lys Asn Ser Arg Phe Ala Gln Asp Phe Leu
305                 310                 315                 320

Ile Arg Pro Ile Gly Glu Lys Leu Pro Thr Ser Gly Gly Cys Ser Ala
                325                 330                 335

Leu Glu Leu Lys Asp Ile Ile Thr Asp Pro Phe Lys Leu Ala Glu Glu
            340                 345                 350

Ser Asp Ser Met Lys Ser Arg Cys Val Pro Asp Ala Ala Gly Gly Cys
        355                 360                 365
```

```
Cys Gly Thr Lys Lys Ser Cys
    370                 375


<210> SEQ ID NO 6
<211> LENGTH: 40
<212> TYPE: DNA
<213> ORGANISM: Homo Sapiens

<400> SEQUENCE: 6

gtcctgagtc gcaggccgag gagacagtga gtgcgcgccc                            40


<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7

tgtaaaacga cggccagt                                                    18


<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8

caggaaacag ctatgacc                                                    18


<210> SEQ ID NO 9
<211> LENGTH: 41
<212> TYPE: DNA
<213> ORGANISM: Artificial Sequence
<220> FEATURE:
<223> OTHER INFORMATION: Primer

<400> SEQUENCE: 9

tgtaaaacga cggccagttc tgcaagatga agtgacaata c                          41


<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10

caggaaacag ctatgacctt gttcgctcca ctgcgatt                              38


<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11

tgtaaaacga cggccagtac gagatttatc cgtgaaaatc gca                        43


<210> SEQ ID NO 12
<211> LENGTH: 41
<212> TYPE: DNA
<213> ORGANISM: Artificial Sequence
```

<220> FEATURE:
<223> OTHER INFORMATION: Primer

<400> SEQUENCE: 12
caggaaacag ctatgaccgg aggcgctcgc gttcccgcct t 41

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
tgtaaaacga cggccagtag ctgtgtctcg agacctttgt 40

<210> SEQ ID NO 14
<211> LENGTH: 47
<212> TYPE: DNA
<213> ORGANISM: Artificial Sequence
<220> FEATURE:
<223> OTHER INFORMATION: Primer

<400> SEQUENCE: 14
caggaaacag ctatgaccgt taattcccta gtgacctgca tcattat 47

<210> SEQ ID NO 15
<211> LENGTH: 47
<212> TYPE: DNA
<213> ORGANISM: Artificial Sequence
<220> FEATURE:
<223> OTHER INFORMATION: Primer

<400> SEQUENCE: 15
tgtaaaacga cggccagttt attttagatg gcttatgaag tcttagt 47

<210> SEQ ID NO 16
<211> LENGTH: 44
<212> TYPE: DNA
<213> ORGANISM: Artificial Sequence
<220> FEATURE:
<223> OTHER INFORMATION: Primer

<400> SEQUENCE: 16
caggaaacag ctatgaccta attgttcaag ttatcagttt ccaa 44

<210> SEQ ID NO 17
<211> LENGTH: 43
<212> TYPE: DNA
<213> ORGANISM: Artificial Sequence
<220> FEATURE:
<223> OTHER INFORMATION: Primer

<400> SEQUENCE: 17
tgtaaaacga cggccagtag cttctagtta gcaatgctca ttt 43

<210> SEQ ID NO 18
<211> LENGTH: 46
<212> TYPE: DNA
<213> ORGANISM: Artificial Sequence
<220> FEATURE:
<223> OTHER INFORMATION: Primer

<400> SEQUENCE: 18
caggaaacag ctatgaccgc tatagtcata acagtaagaa tataga 46

<210> SEQ ID NO 19
<211> LENGTH: 50
<212> TYPE: DNA
<213> ORGANISM: Artificial Sequence
<220> FEATURE:
<223> OTHER INFORMATION: Primer

<400> SEQUENCE: 19
tgtaaaacga cggccagttg cctgatgtta ttttctgcac attcaaactt 50

<210> SEQ ID NO 20
<211> LENGTH: 47
<212> TYPE: DNA
<213> ORGANISM: Artificial Sequence
<220> FEATURE:
<223> OTHER INFORMATION: Primer

<400> SEQUENCE: 20
caggaaacag ctatgaccat tcagtgacaa ctgtcaccac ggattta 47

<210> SEQ ID NO 21
<211> LENGTH: 44
<212> TYPE: DNA
<213> ORGANISM: Artificial Sequence
<220> FEATURE:
<223> OTHER INFORMATION: Primer

<400> SEQUENCE: 21
tgtaaaacga cggccagtcc ttggcacttg actattgatt gtaa 44

<210> SEQ ID NO 22
<211> LENGTH: 44
<212> TYPE: DNA
<213> ORGANISM: Artificial Sequence
<220> FEATURE:
<223> OTHER INFORMATION: Primer

<400> SEQUENCE: 22
caggaaacag ctatgaccat cctggctatt agcagaaagg agtt 44

<210> SEQ ID NO 23
<211> LENGTH: 45
<212> TYPE: DNA
<213> ORGANISM: Artificial Sequence
<220> FEATURE:
<223> OTHER INFORMATION: Primer

<400> SEQUENCE: 23
tgtaaaacga cggccagtgt ggcgtactgc atacatgaat attat 45

<210> SEQ ID NO 24
<211> LENGTH: 44
<212> TYPE: DNA
<213> ORGANISM: Artificial Sequence
<220> FEATURE:
<223> OTHER INFORMATION: Primer

<400> SEQUENCE: 24
caggaaacag ctatgacccc agataacaga aagtatccct caat 44

<210> SEQ ID NO 25
<211> LENGTH: 43
<212> TYPE: DNA
<213> ORGANISM: Artificial Sequence
<220> FEATURE:
<223> OTHER INFORMATION: Primer

<400> SEQUENCE: 25
tgtaaaacga cggccagttg acagacagca gggactatta taa 43

<210> SEQ ID NO 26
<211> LENGTH: 46
<212> TYPE: DNA
<213> ORGANISM: Artificial Sequence
<220> FEATURE:
<223> OTHER INFORMATION: Primer

<400> SEQUENCE: 26
caggaaacag ctatgaccag aaaaatggga ggcaatgcaa agtcaa 46

<210> SEQ ID NO 27
<211> LENGTH: 42
<212> TYPE: DNA
<213> ORGANISM: Artificial Sequence
<220> FEATURE:
<223> OTHER INFORMATION: Primer

<400> SEQUENCE: 27
tgtaaaacga cggccagtca gtgtgtaagg attagtgctg gt 42

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
caggaaacag ctatgaccgt ctgggtgaca gagagagact cca 43

<210> SEQ ID NO 29
<211> LENGTH: 44
<212> TYPE: DNA
<213> ORGANISM: Artificial Sequence
<220> FEATURE:
<223> OTHER INFORMATION: Primer

<400> SEQUENCE: 29
tgtaaaacga cggccagtga gaagtcgttt tagcatttcc gtat 44

<210> SEQ ID NO 30
<211> LENGTH: 47
<212> TYPE: DNA
<213> ORGANISM: Artificial Sequence
<220> FEATURE:
<223> OTHER INFORMATION: Primer

<400> SEQUENCE: 30
caggaaacag ctatgaccca tttgttgttt cttatggtct gtgctat 47

<210> SEQ ID NO 31
<211> LENGTH: 25
<212> TYPE: PRT
<213> ORGANISM: Homo Sapiens

<400> SEQUENCE: 31

```
Arg Asp Ala Glu Ile Gln Lys Asp Val Gln Thr Tyr Tyr Gly Gln Val
 1               5                  10                  15

Leu Lys Arg Ser Ala Asp Leu Gln Cys
            20                  25
```

-continued

```
<210> SEQ ID NO 32
<211> LENGTH: 20
<212> TYPE: PRT
<213> ORGANISM: Homo Sapiens

<400> SEQUENCE: 32

Asp Ile Ile Thr Asp Pro Phe Lys Leu Ala Glu Glu Ser Asp Ser Met
 1               5                  10                  15

Lys Ser Arg Cys
            20


<210> SEQ ID NO 33
<211> LENGTH: 37
<212> TYPE: DNA
<213> ORGANISM: Artificial Sequence
<220> FEATURE:
<223> OTHER INFORMATION: Primer

<400> SEQUENCE: 33

aagaagggta ccacgagatt tatccgtgaa aatcgca                             37


<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34

aagaagctcg agagggaagg ggctgggggc t                                   31


<210> SEQ ID NO 35
<211> LENGTH: 36
<212> TYPE: DNA
<213> ORGANISM: Homo Sapiens

<400> SEQUENCE: 35

gtcgcaggcc gaggagacag tgagtgcgcg ccctga                              36


<210> SEQ ID NO 36
<211> LENGTH: 35
<212> TYPE: DNA
<213> ORGANISM: Homo Sapiens

<400> SEQUENCE: 36

gtcgcaggcc gaggagacag tgagtgcgcg ccctg                               35
```